(12) United States Patent
Howell et al.

(10) Patent No.: US 6,749,588 B1
(45) Date of Patent: Jun. 15, 2004

(54) CATHETER AND INTRODUCER NEEDLE ASSEMBLY WITH NEEDLE SHIELD

(75) Inventors: Glade H. Howell, Sandy, UT (US); Weston F. Harding, Lehi, UT (US); Christopher N. Cindrich, South Jordan, UT (US); Timothy J. Erskine, Sandy, UT (US)

(73) Assignee: Becton Dickinson and Company, Franklin Lakes, NJ (US)

( * ) Notice: Subject to any disclaimer, the term of this patent is extended or adjusted under 35 U.S.C. 154(b) by 173 days.

(21) Appl. No.: 09/717,148

(22) Filed: Nov. 21, 2000

Related U.S. Application Data

(63) Continuation-in-part of application No. 09/590,600, filed on Jun. 9, 2000, now abandoned, which is a continuation-in-part of application No. 09/312,335, filed on May 14, 1999, now Pat. No. 6,379,333, which is a continuation-in-part of application No. 09/057,718, filed on Apr. 9, 1998, now Pat. No. 6,004,294, application No. 09/717,148, which is a continuation-in-part of application No. 09/499,331, filed on Feb. 4, 2000, now abandoned, which is a continuation-in-part of application No. 09/312,335, filed on May 14, 1999, now Pat. No. 6,379,333, which is a continuation-in-part of application No. 09/057,718, filed on Apr. 9, 1998, now Pat. No. 6,004,294, application No. 09/717,148, which is a continuation-in-part of application No. 09/406,026, filed on Sep. 24, 1999, now abandoned.

(51) Int. Cl.7 .......................... A61M 5/178; A61M 5/00
(52) U.S. Cl. ......................... 604/164.08; 604/164.12; 604/110
(58) Field of Search ............... 604/164.01, 164.07, 604/164.08, 164.12, 110, 162, 166.01, 158, 198, 263

(56) References Cited

U.S. PATENT DOCUMENTS

| | | | |
|---|---|---|---|
| 4,755,170 A | 7/1988 | Golden | 604/52 |
| 4,810,248 A | 3/1989 | Masters et al. | 604/192 |
| 4,816,024 A | 3/1989 | Sitar et al. | 604/192 |
| 4,832,696 A | 5/1989 | Luther et al. | 604/164 |
| 4,834,718 A | 5/1989 | McDonald | 604/195 |
| 4,846,811 A | 7/1989 | Vanderhoof | 604/263 |
| 4,917,669 A | 4/1990 | Bonaldo | 604/164 |
| 4,929,241 A | 5/1990 | Kulli | 604/263 |
| 4,944,725 A | 7/1990 | McDonald | 604/164 |
| 4,964,854 A | 10/1990 | Luther | 604/166 |
| 4,978,344 A | 12/1990 | Dombrowski et al. | 604/198 |
| 4,994,041 A | 2/1991 | Dombrowski et al. | 604/164 |
| 5,049,136 A | 9/1991 | Johnson | 604/198 |
| 5,051,109 A | 9/1991 | Simon | 604/263 |
| 5,053,017 A | 10/1991 | Chamuel | 604/192 |
| 5,085,648 A | 2/1992 | Purdy et al. | 604/198 |
| 5,135,504 A | 8/1992 | McLees | 604/164 |
| 5,147,327 A | 9/1992 | Johnson | 604/198 |
| 5,176,655 A | 1/1993 | McCormick et al. | 604/198 |
| 5,186,712 A | 2/1993 | Kelso et al. | 604/165 |

(List continued on next page.)

FOREIGN PATENT DOCUMENTS

| | | |
|---|---|---|
| EP | 0 747 083 A2 | 12/1996 |
| EP | 0 747 085 A2 | 12/1996 |

(List continued on next page.)

Primary Examiner—Michael J. Hayes
(74) Attorney, Agent, or Firm—James J. Murtha

(57) ABSTRACT

A catheter and introducer needle assembly with a needle shield is provided. The needle shield includes a means for preventing unwanted distal movement of the needle once the needle has been withdrawn into the needle shield. The needle shield also includes a means for connecting the needle shield to the catheter hub until the sharp distal tip of the introducer needle has been withdrawn into the needle shield. Thus, when the distal end of the introducer needle extends from the distal portion of the needle shield, the needle shield is connected to the catheter hub and when the sharp distal end of the introducer needle is withdrawn into the needle shield, the needle shield is disconnected from the catheter hub.

20 Claims, 75 Drawing Sheets

U.S. PATENT DOCUMENTS

| | | | | |
|---|---|---|---|---|
| 5,215,525 A | 6/1993 | Sturman | ................... | 604/164 |
| 5,215,528 A | 6/1993 | Purdy et al. | ................ | 604/164 |
| RE34,416 E | 10/1993 | Lemieux | ................... | 604/164 |
| 5,279,591 A | 1/1994 | Simon | ....................... | 604/263 |
| 5,300,045 A | 4/1994 | Plassche, Jr. | .............. | 604/263 |
| 5,312,359 A | 5/1994 | Wallace | ..................... | 604/164 |
| 5,322,517 A | 6/1994 | Sircom et al. | ............. | 604/198 |
| 5,328,482 A | 7/1994 | Sircom et al. | ............. | 604/164 |
| 5,395,347 A | 3/1995 | Blecher et al. | ............ | 604/198 |
| 5,409,461 A | 4/1995 | Steinman | ................... | 604/110 |
| 5,458,658 A | 10/1995 | Sircom | ..................... | 604/192 |
| 5,558,651 A | 9/1996 | Crawford et al. | .......... | 604/263 |
| 5,562,633 A | 10/1996 | Wozencroft | ................ | 604/171 |
| 5,573,510 A | 11/1996 | Isaacson | .................... | 604/158 |
| 5,584,809 A | 12/1996 | Gaba | ......................... | 604/110 |
| 5,584,818 A | 12/1996 | Morrison | ................... | 604/197 |
| 5,599,310 A | 2/1997 | Bogert | ...................... | 604/164 |
| 5,601,536 A | 2/1997 | Crawford et al. | .......... | 604/263 |
| 5,611,781 A | 3/1997 | Sircom et al. | ............. | 604/164 |
| 5,613,952 A | 3/1997 | Pressly, Sr. et al. | ....... | 604/110 |
| 5,662,610 A | 9/1997 | Sircom | ..................... | 604/110 |
| 5,676,658 A | 10/1997 | Erskine | .................... | 604/263 |
| 5,695,474 A | 12/1997 | Daugherty | .................. | 604/162 |
| 5,697,907 A | 12/1997 | Gaba | ......................... | 604/110 |
| 5,704,919 A | 1/1998 | Kraus et al. | ................ | 604/192 |
| 5,713,876 A | 2/1998 | Bogert et al. | ............... | 604/243 |
| 5,718,688 A | 2/1998 | Wozencroft | ................ | 604/164 |
| 5,833,670 A | 11/1998 | Dillon et al. | ............... | 604/263 |
| 5,853,393 A | 12/1998 | Bogert | ...................... | 604/165 |
| 5,865,806 A | 2/1999 | Howell | ...................... | 604/164 |
| 5,879,337 A | 3/1999 | Kuracina et al. | .......... | 604/192 |
| 5,882,337 A | 3/1999 | Bogert et al. | ............... | 604/110 |
| 5,911,705 A | 6/1999 | Howell | ...................... | 604/110 |
| 5,935,109 A | 8/1999 | Donnan | ..................... | 604/164 |
| 5,951,515 A | 9/1999 | Osterlind | ................... | 604/110 |
| 6,001,080 A | 12/1999 | Kuracina et al. | .......... | 604/171 |
| 6,004,294 A | 12/1999 | Brimhall et al. | ........... | 604/164 |
| 6,012,213 A | 1/2000 | Chang et al. | ................. | 29/447 |
| 6,117,108 A | 9/2000 | Woehr et al. | ............... | 604/110 |

FOREIGN PATENT DOCUMENTS

| | | | | |
|---|---|---|---|---|
| EP | 0 750 916 A2 | 1/1997 | ......... | A61M/25/06 |
| GB | 2 343 118 A | 5/2000 | | |
| WO | WO 98/19725 | 5/1998 | ............ | A61M/5/32 |
| WO | WO 98./57689 | 12/1998 | | |
| WO | WO 99/08742 | 2/1999 | ......... | A61M/25/06 |
| WO | WO 00/06226 | 2/2000 | ......... | A61M/5/178 |
| WO | WO 02/045786 A3 | 6/2002 | | |

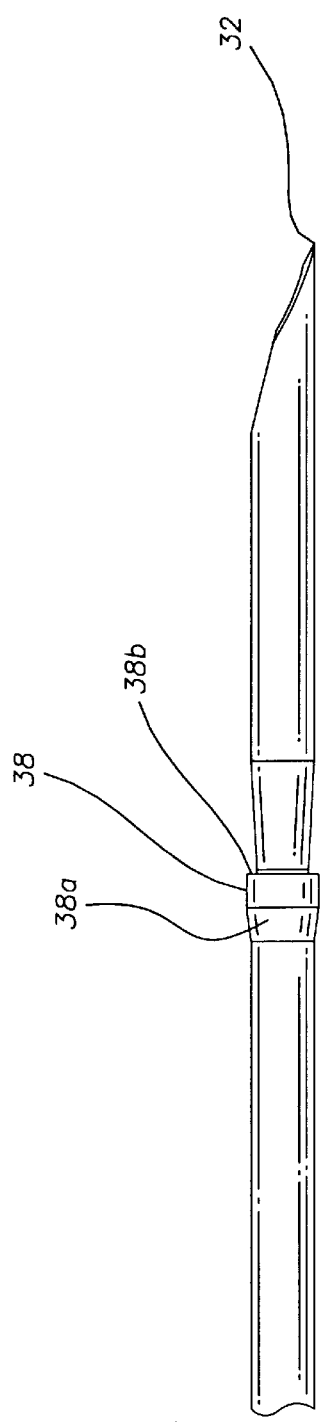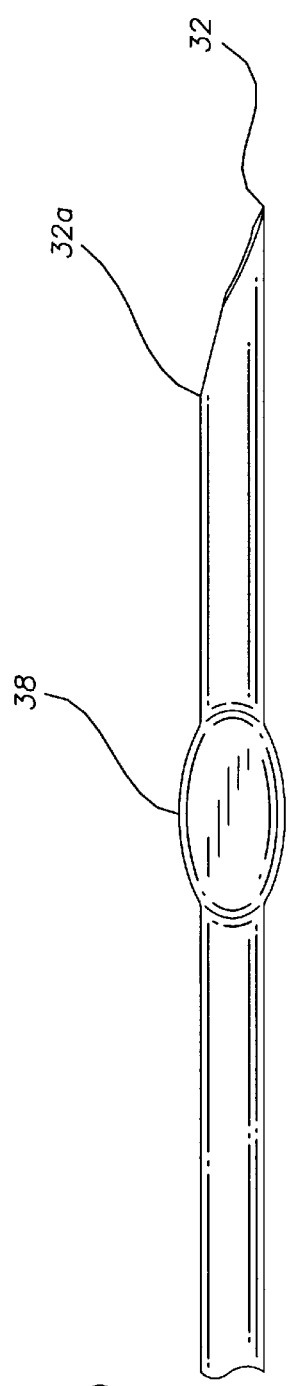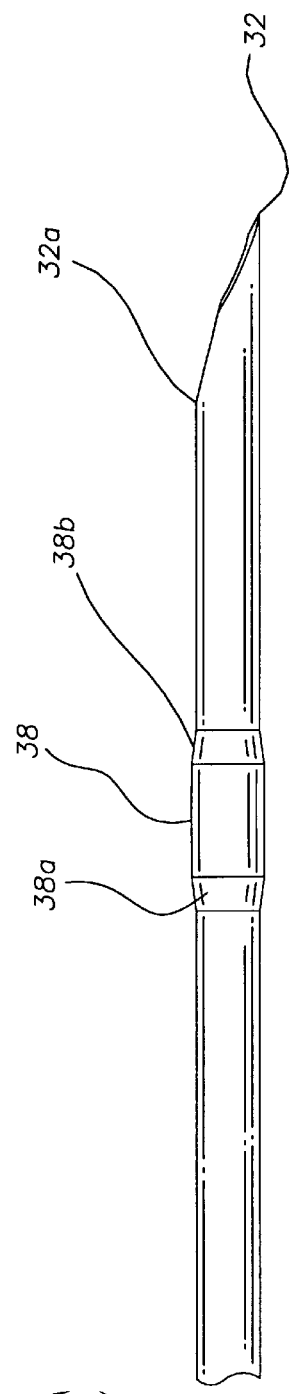

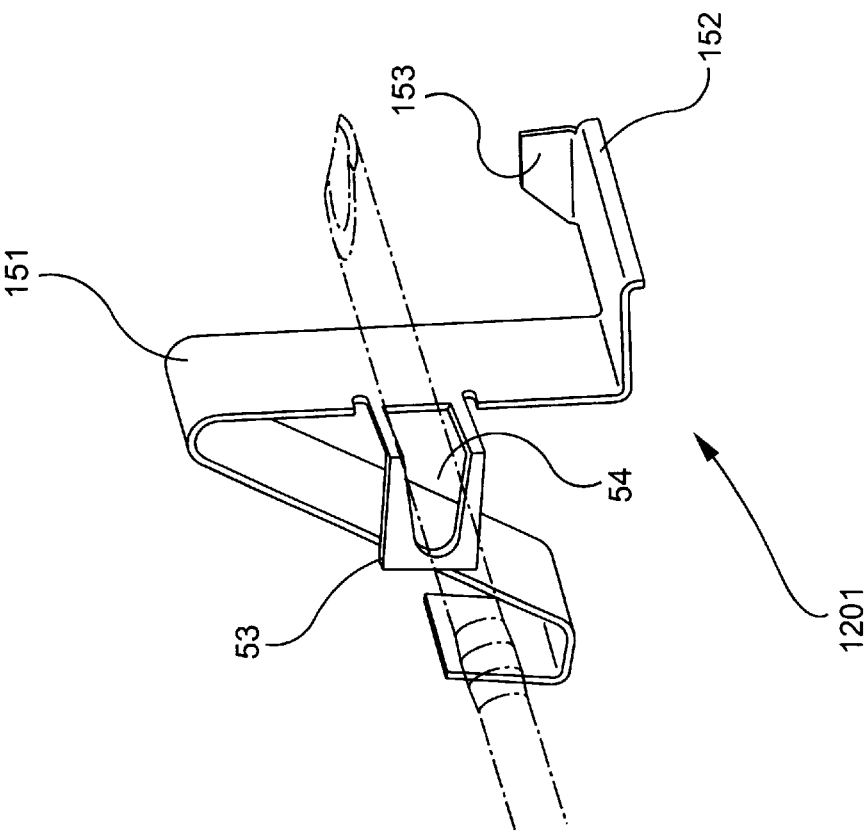
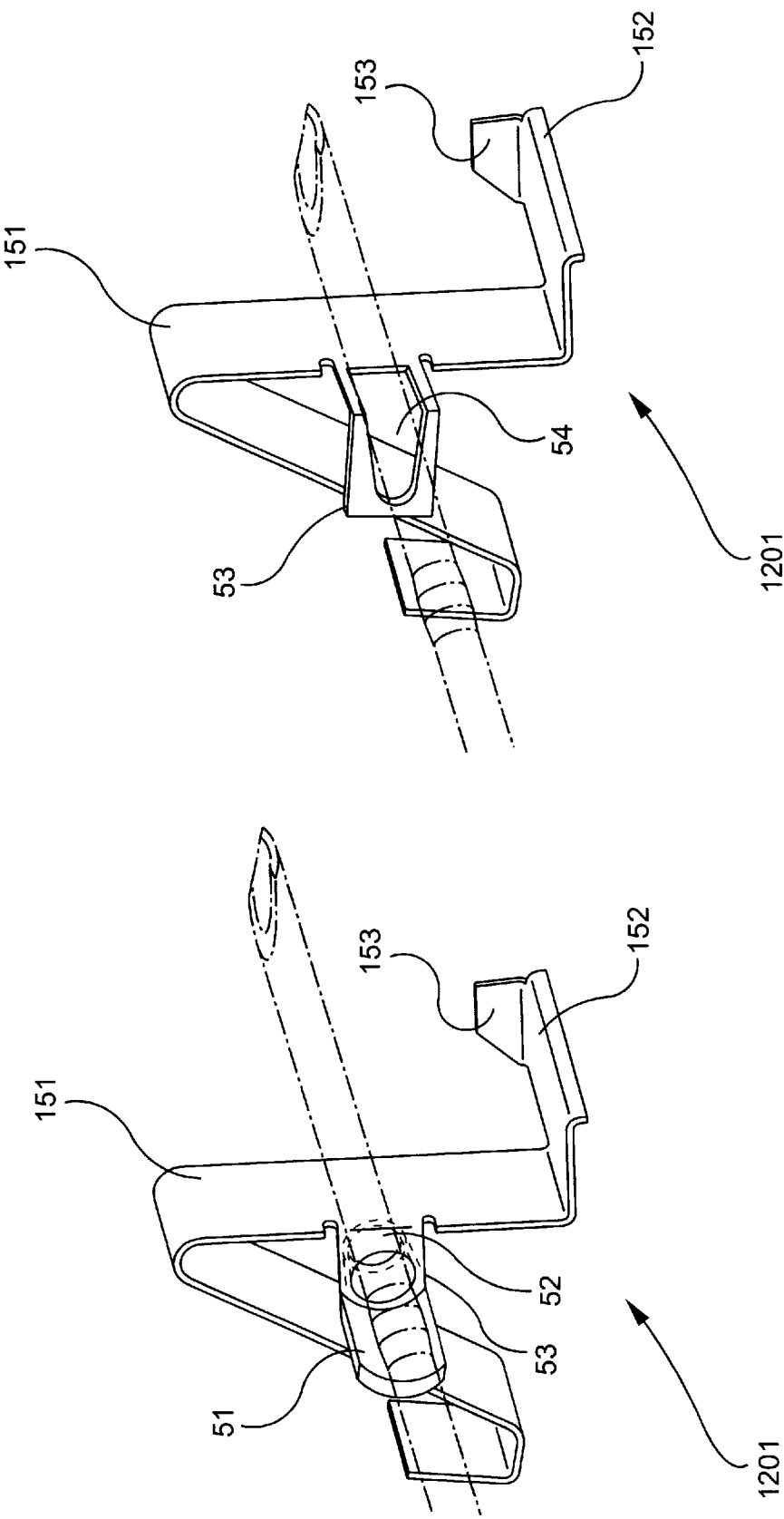

CATHETER AND INTRODUCER NEEDLE ASSEMBLY WITH NEEDLE SHIELD

This application is a continuation-in-part of application Ser. No. 09/590,600 filed Jun. 9, 2000, now abandoned, which is a continuation-in-part of application Ser. No. 09/312,335 filed May 14, 1999, now U.S. Pat. No. 6,379,333, which is a continuation-in-part of application Ser. No. 09/057,718 filed Apr. 9, 1998, now U.S. Pat. No. 6,004,294. This application is also a continuation-in-part of application Ser. No. 09/499,331 filed Feb. 4, 2000, now abandoned, which is a continuation-in-part of application Ser. No. 09/312,335 filed May 14, 1999, now U.S. Pat. No. 6,379,333, which is a continuation-in-part of application Ser. No. 09/057,718 filed Apr. 9, 1998, now U.S. Pat. No. 6,004,294. This application is also a continuation-in-part of application Ser. No. 09/406,026 filed Sep. 24, 1999, now abandoned.

BACKGROUND OF THE INVENTION

The subject invention relates to a catheter and introducer needle assembly that includes a needle shield that will safely shield the sharp distal tip of the introducer needle after the needle has been used to insert the catheter into a patient. In addition, this invention includes a mechanism to connect the needle shield to the catheter until the sharp distal tip of the introducer needle is covered by the needle shield.

Catheters, particularly intravascular (IV) catheters, are used for infusing fluid, such as normal saline solution, various medicaments and total parenteral nutrition, into a patient, withdrawing blood from a patient or monitoring various parameters of the patient's vascular system. Peripheral IV catheters tend to be relatively short, and typically are on the order of about two inches or less in length. The most common type of IV catheter is an over-the-needle peripheral IV catheter. As its name implies, an over-the-needle catheter is mounted over an introducer needle having a sharp distal tip. At least the distal portion of the catheter tightly engages the outer surface of the needle to prevent peelback of the catheter and thus facilitates insertion of the catheter into the blood vessel. The catheter and the introducer needle are assembled so that the distal tip of the introducer needle extends beyond the distal tip of the catheter with the bevel of the needle facing up away from the patient's skin.

The catheter and introducer needle assembly is inserted at a shallow angle through the patient's skin into a blood vessel. There are many techniques for inserting such a catheter and introducer needle assembly into a patient. In one insertion technique, the introducer needle and catheter are inserted completely into the blood vessel together. In another technique, the introducer needle is partially withdrawn into the catheter after the initial insertion into the blood vessel. The catheter is then threaded over the needle and inserted completely into the blood vessel.

In order to verify proper placement of the catheter in the blood vessel, the clinician confirms that there is flashback of blood in a flashback chamber. The flashback chamber is typically formed as part of the needle hub. Once proper placement of the catheter into the blood vessel is confirmed, the clinician applies pressure to the blood vessel by pressing down on the patient's skin over the blood vessel distal of the introducer needle and the catheter. This finger pressure occludes or at least minimizes further blood flow through the introducer needle and the catheter. The clinician then withdraws the introducer needle, leaving the catheter in place, and attaches an appropriate device to the catheter. Such a device can include a fluid delivery device, a PRN, a deadender cap or a blood pressure monitoring probe. Once the introducer needle is withdrawn from the catheter, the introducer needle is a "blood contaminated sharp" and must be properly handled.

In recent years, there has been great concern over the contamination of clinicians with a patient's blood and a recognition that "blood contaminated sharps" must be disposed to avoid an accidental needle stick. This concern has arisen because of the advent of currently incurable and fatal diseases, such as Acquired Immunosuppressive Deficiency Syndrome ("AIDS"), which can be transmitted by the exchange of body fluids from an infected person to another person. Thus, contact with the body fluid of an AIDS infected person must be avoided. As noted above, if an introducer needle has been used to place a catheter in a blood vessel of an AIDS infected person, the introducer needle, via its sharp distal tip, is a vehicle for the transmission of the disease. Although clinicians are aware of the need to properly handle "blood contaminated sharps", unfortunately in certain medical environments, such as emergency situations or as a result of inattention or neglect, needlesticks with a contaminated introducer needle still occur.

As a result of the problem of accidental needlesticks by "blood contaminated sharps", various needle shields have been developed. Generally, such needle shields work for their intended purpose but could be improved. For example, some needle shields are bulky, difficult to use, require special features or techniques to be operative, or may leave the sharp distal tip exposed after use until the clinician manually activates the needle shielding mechanism.

In addition, some of these needle shields can be easily disconnected from the catheter hub before the needle shield covers the sharp distal tip of the introducer needle. A mechanism to avoid this premature disconnection is a plurality of fingers longitudinally extending from the needle shield with tabs extending radially inwardly from the fingers that engage the flange at the proximal end of the catheter hub. The fingers and tabs hold the needle shield to the catheter. The configuration of the fingers and tabs is designed such that the force needed to overcome the engagement between the fingers and tabs and the catheter hub is greater than the typical force needed to move the introducer needle proximally into the needle shield. However, once the introducer needle has been fully withdrawn into the needle shield, the clinician can exert a greater proximally directed force to remove the needle shield from the catheter hub. Thus the needle shield remains engaged with the catheter until the introducer needle has been completely removed from the catheter and is safely shielded in the needle shield. Unfortunately, this configuration does not consistently ensure that the needle shield remains connected to the catheter hub until the introducer needle is locked in the needle shield. This may be undesirable because the contaminated needle could then be exposed increasing the chances for an accidental needlestick.

SUMMARY OF THE INVENTION

It is therefore an object of this invention to provide a needle shield that is compact.

It is another object of this invention to provide a needle shield that is simple and easy to use.

It is still another object of this invention to provide a needle shield that requires no special features or techniques to be operative.

It is yet another object of this invention to provide a needle shield that automatically shields the sharp distal tip of the introducer needle upon withdrawal of the introducer needle from the catheter.

It is a further object of this invention to provide a catheter and introducer needle assembly with a needle shield where the needle shield remains connected to the catheter until the needle shield covers the sharp distal tip of the introducer needle.

The catheter and introducer needle assembly with needle shield of this invention includes a catheter, an introducer needle and a needle shield.

The catheter has a distal end and a proximal end connected to the distal end of a catheter hub. The catheter is coaxially disposed over the introducer needle and the distal portion of the catheter tightly engages the outer surface of the introducer needle to prevent peelback of the catheter and thus facilitate insertion of the catheter into the patient's blood vessel. Prior to use, the catheter is located about the introducer needle so that the sharp distal tip of the introducer needle is distal of the distal end of the catheter.

The introducer needle has a sharp distal tip and a proximal end connected to the distal end of a needle hub. A flashback chamber may be defined in the needle hub. Typically a vented plug is located in the open proximal end of the flashback chamber to allow air to escape from the flashback chamber when blood enters the flashback chamber from the introducer needle. The introducer needle may also define, along a distal portion thereof, a discontinuous portion, which can take a number of different forms. For example, a slot, or an enlarged diameter portion formed on the introducer needle may be used. If an enlarged diameter portion is used it may have a tapered proximal portion or a tapered distal portion or both. The taper can be oriented at almost any angle to the longitudinal axis of the introducer needle. In certain embodiments, the distal portion may be oriented generally perpendicular to the longitudinal axis of the introducer needle. However, the main requirement is that the discontinuous portion has any configuration that cooperates with a lock associated with the needle shield to prevent unwanted distal movement of the introducer needle with respect to the needle shield. In other words, the sharp distal tip will not be re-exposed from the distal end of the needle shield once the sharp distal tip has been withdrawn into the needle shield after use. The discontinuous portion may also cooperate with a means for preventing unwanted proximal movement of the introducer needle with respect to the needle shield once the sharp distal tip of the introducer needle has been proximally withdrawn into the needle shield. This prevents re-exposure of the sharp distal tip of the introducer needle from the proximal end of the needle shield.

The needle shield is defined by a housing having an internal cavity through which the introducer needle extends. A lock associated with the needle shield prevents unwanted distal movement of the introducer needle once the introducer needle has been proximally withdrawn into the needle shield. Also associated with the needle shield is a means for preventing unwanted proximal movement of the introducer needle once the sharp distal tip of the introducer needle has been proximally withdrawn into the needle shield.

Various locks can be used to prevent unwanted distal movement of the sharp distal tip of the introducer needle out of the needle shield once the sharp distal tip has been proximally withdrawn into the introducer needle shield. For example, a transverse barrier that rides along the needle shaft as the introducer needle is withdrawn into the needle shield and that moves in front of the sharp distal tip once the needle tip is proximal of the transverse barrier may be used. In such an embodiment, no discontinuous portion is needed on the introducer needle. Alternatively, a lock may be used in conjunction with a discontinuous portion formed on the introducer needle. In such an embodiment, the lock allows the discontinuous portion of the introducer needle to move past the lock in a proximal direction but prevents movement of the discontinuous portion past the lock in a distal direction. Such a lock can take many forms and can include a spring gate, a leaf spring with one or a plurality of locking legs, where the locking legs have a variety of configurations, a tube having one or more inwardly and proximally directed tabs, a speed nut with one or more radially inwardly and proximally directed tabs extending from the main body or a retention plate with one or more radially inwardly directed tabs formed around the main body.

The spring gate has a generally U shaped configuration with a pair of spaced apart tines. The introducer needle is disposed between the tines and is moveable longitudinally past the tines. A biasing mechanism forces the spring gate up into contact with the introducer needle. With this embodiment, the discontinuous portion on the needle is preferably an enlarged diameter portion. A tapered portion immediately proximal of the enlarged diameter portion on the introducer needle may be used to facilitate proximal movement of the enlarged diameter portion past the spring gate. The enlarged diameter portion could be formed with a distally facing shoulder to provide a further positive engagement with the spring gate and minimize the possibility that a clinician could force the sharp distal tip of the introducer needle distally out of the needle shield during normal use and under normal conditions.

When the introducer needle is withdrawn proximally into the needle shield, the introducer needle rides past the tines of the spring gate. As the enlarged diameter portion passes by the tines, the enlarged diameter portion engages the tines. This forces the spring gate to rotate toward the proximal end of the introducer needle. The spring gate is also forced downwardly against the bias of the biasing mechanism. This movement by the spring gate allows the enlarged diameter portion of the introducer needle to move proximally past the spring gate. Once the enlarged diameter portion is proximal of the spring gate the biasing mechanism forces the spring gate upwardly and the tines of the spring gate rotate toward the distal end of the introducer needle. This movement of the spring gate ensures that the main portion of the introducer needle is located in the space between the tines of the spring gate so the tines extend up past the introducer needle. In this position, the spring gate abuts a proximal facing surface of a shoulder or wall in the housing to prevent further distal rotation of the spring gate. Thus, if a clinician tries to advance the introducer needle distally, the enlarged diameter portion would engage the tines of the spring gate. In addition, the spring gate would engage the wall or shoulder in the housing and prevent the introducer needle from being moved distally.

Another lock that may be used to prevent unwanted distal movement of the introducer needle once the sharp distal tip of the introducer needle has been proximally withdrawn into the introducer needle shield is a leaf spring. With the leaf spring, any configuration for the discontinuous portion can be used. However, preferably the discontinuous portion is an enlarged diameter portion on the introducer needle with a distally facing shoulder when the leaf spring is used.

The leaf spring has a proximal wall, a support leg and at least one locking leg. Preferably, the support leg and the locking leg are configured such that the locking leg extends generally back toward the proximal end of the support leg. In this configuration the support leg and the locking leg have a generally V-shape, with the apex of the V facing distally. Although this configuration is preferred, any other configuration that biases the locking leg toward the introducer needle could be used. For example, the locking leg could be generally perpendicular to the support leg or oriented at some other angle less than 90 degrees. Alternatively, the locking leg could be formed so it has a generally U-shaped or V-shaped configuration with a pair of spaced apart tines. With such a configuration the locking legs prevent unwanted distal movement of the introducer needle in a manner analogous to the spring gate discussed above. In addition, the portion of the locking leg that rides along the introducer needle shaft could be contoured to approximate a portion of the circumference of the introducer needle to minimize drag as the introducer needle rides past the locking leg.

The configuration of the leaf spring ensures that the locking leg is biased toward and abuts the main portion of the introducer needle. However this bias still allows the locking leg to ride over the enlarged diameter portion as the introducer needle is moved proximally into the needle shield. Once the distally facing shoulder of the enlarged diameter portion is moved proximally of the locking leg, the locking leg moves back into contact with the main portion of the introducer needle. Thereafter, if the introducer needle is moved distally, the locking leg will engage the distally facing shoulder and prevent further distal movement of the introducer needle.

The leaf spring and housing could be configured to maximize the mechanical engagement force between the locking leg and the introducer needle. For example, the cavity where the lock is located could have a tapered cross-section and the leaf spring could be disposed therein so it could move distally into the tapered cross-section.

In this embodiment of the leaf spring, the introducer needle would be proximally withdrawn into the needle shield just like in the previous embodiments until the discontinuous portion is proximal of the locking leg. Thereafter, if the introducer needle is moved distally, the locking leg engages the discontinuous portion and causes the lock to move distally into the tapered cross-section of the cavity. This causes the leaf spring to engage the introducer needle with increasing force until the tapered cross-section prevents further distal movement of the leaf spring. At this point, the locking leg forcefully engages the discontinuous portion preventing distal movement of the introducer needle.

In order to minimize drag on the introducer needle, the locking leg could be initially spaced apart from the introducer needle. In an alternate embodiment, the locking leg could be held out of engagement with the introducer needle by a finger and tab arrangement on the leaf spring and the housing. The leaf spring is movable proximally with respect to the housing by the engagement of the discontinuous portion of the introducer needle with the proximal wall of the leaf spring so the finger and tab can be moved out of engagement with one another. This allows the locking leg to move into engagement with the introducer needle by the inward bias of the locking leg. Thereafter, unwanted distal movement is prevented as discussed above.

In another embodiment of the leaf spring, the cavity has a distal portion and a proximal portion where the diameter of the distal portion is larger than the diameter of the proximal portion. The leaf spring is disposed in the cavity for proximal movement from the distal portion to the proximal portion. When the leaf spring is disposed in the distal portion, the locking leg does not engage the introducer needle. As the introducer needle is withdrawn proximally into the needle shield, the discontinuous portion of the introducer needle engages the proximal wall of the leaf spring. This engagement causes the leaf spring to move proximally with the introducer needle into the proximal portion of the cavity until the proximal wall of the leaf spring abuts the proximal wall of the housing. At this point, any further proximal movement of the leaf spring and the introducer needle is prevented.

When the leaf spring is in the proximal portion, the walls defining the cavity force the locking legs inwardly into engagement with the introducer needle. The leaf spring includes flexible, outwardly extending fingers. The inner walls of the proximal portion in the cavity define slots having a proximally facing wall for receiving the fingers. When the leaf spring is in the proximal portion so the proximal wall of the leaf spring abuts the proximal wall of the housing, the fingers are located in the slots so they are proximal of the proximally facing wall. Thus distal movement of the leaf spring is prevented by the engagement of the fingers and the proximally facing wall. As a result when the discontinuous portion of the introducer needle engages the locking leg, distal movement of the introducer needle is prevented.

Alternatively, the locking leg can be oriented so it is generally perpendicular to the support leg and can be formed with a small diameter opening formed therein. This opening is too small to allow the enlarged diameter portion on the introducer needle to pass therethrough but is large enough to allow the main portion of the introducer needle to pass through.

The leaf spring is held in a biased position by the shaft of the introducer needle. Thus, the locking leg rides along the introducer needle shaft as the introducer needle is retracted into the needle shield. Once the distal end of the introducer needle has been retracted into the needle shield and is proximal of the locking leg, the leaf spring returns to its unbiased position. As such, the locking leg can move so the small diameter opening in the locking leg will be aligned with the sharp distal tip of the introducer needle. Thus, If the introducer needle is moved distally with respect to the leaf spring, the distal end of the introducer needle travels through and past the small diameter opening formed in the locking leg. However, the introducer needle is prevented from being moved distally outside of the needle shield when the enlarged diameter portion on the introducer needle engages the small diameter opening formed in the locking leg.

Preferably, the housing includes at least one additional medial wall adjacent to the locking leg. This medial wall includes an opening therein to allow the main portion of the introducer needle to extend through the medial wall. This provides additional support for the introducer needle and ensures that the introducer needle is aligned with the small diameter opening in the locking leg when the leaf spring returns to its unbiased position.

A variation of the foregoing leaf spring includes an opening in the locking leg with a diameter slightly larger than the diameter of the enlarged diameter portion of the introducer needle. The leaf spring also includes a proximal wall defining an opening therein slightly larger than the diameter of the shaft of the introducer needle but smaller than the diameter of the enlarged diameter portion. The leaf spring is also slidably disposed in the housing of the needle shield but has an end portion of the locking leg that is substantially held in place with respect to the housing. This allows the locking leg to rotate in the housing.

Prior to use when the sharp distal tip of the introducer needle extends beyond the distal end of the needle shield, the locking leg is perpendicular to the longitudinal axis of the introducer needle. In this position, the introducer needle extends through the opening in the proximal wall and the opening in the locking leg. Since the diameter of the opening in the locking leg is slightly larger than the diameter of the enlarged diameter portion, it can be retracted through the opening in the locking leg so the enlarged diameter portion is proximal of the locking leg.

Once the enlarged diameter portion of the introducer needle engages the opening in the proximal wall, the leaf spring moves proximally with the introducer needle until the proximal wall of the leaf spring abuts the proximal wall of the housing. Because one end of the locking leg is substantially held in place with respect to the housing, this proximal movement of the leaf spring causes the proximal leg to rotate clockwise as seen in the FIGS. This changes the orientation of the opening in the locking leg so that a plane defining that opening is no longer perpendicular to the longitudinal axis of the introducer needle. Instead, the opening is angled so that the effective diameter of the opening, i.e. the perpendicular dimension of the opening, is less than the diameter of the enlarged diameter portion. In addition, in this position, a detent associated with the leaf spring prevents subsequent distal movement of the leaf spring. Thus any subsequent distal movement of the introducer needle is prevented since the enlarged diameter portion can not be moved through the opening in the locking leg.

An alternative lock that prevents distal movement of the sharp distal tip of the introducer needle out of the distal end of the needle shield once the sharp distal tip has been proximally withdrawn into the needle shield is a tube formed in the housing. Again, although most forms of the discontinuous portion could be used with this embodiment, the discontinuous portion is preferably an enlarged diameter portion with a distally facing shoulder. The tube is located inside the housing to allow the introducer needle to pass therethrough and includes at least one movable lanced protrusion or tab that extends proximally and inwardly into the tube. Preferably the lanced protrusion, or tab is biased inwardly. Because the lanced protrusion or tab is movable, the enlarged diameter portion of the introducer needle with the distally facing shoulder can move proximally past the lanced protrusion or tab. Once the introducer needle has been withdrawn proximally into the needle shield such that the lanced protrusion or tab is distal of the distally facing shoulder, unwanted distal movement of the introducer needle will be prevented when the distally facing shoulder engages the lanced protrusion or tab.

Although the enlarged diameter portion having a distally facing shoulder is the preferred embodiment for the discontinuous portion, a notch formed in the introducer needle could be used as the discontinuous portion. When the introducer needle is withdrawn proximally into the needle shield, one of the lanced protrusions or tabs extends into the notch. Thereafter, distal movement of the introducer needle is prevented when the lanced protrusion or tab engages the proximal edge of the notch.

Yet another lock that prevents distal movement of the sharp distal tip of the introducer needle out of the distal end of the needle shield once the sharp distal tip has been proximally withdrawn into the needle shield is a speed nut that is formed in or added to the housing. The speed nut is located in the housing and defines a through hole and at least one proximally oriented and radially inwardly extending tab adjacent the through hole. The through hole should be slightly larger than the diameter of the introducer needle to allow the main portion of the introducer needle to pass therethrough. Because the tab is proximally oriented, the discontinuous portion can move proximally past the tab.

Once the introducer needle has been withdrawn proximally into the needle shield such that the tab is distal of the discontinuous portion, any distal movement of the introducer needle will be prevented when the discontinuous portion engages the tab. If an enlarged diameter portion is used for the discontinuous portion, it would be desirable to include a distally facing shoulder on the enlarged diameter portion to ensure firm engagement with the tab. Alternatively, the discontinuous portion may be a notch formed in the needle. When the introducer needle is proximally withdrawn into the needle shield the tab drops into the notch to thereby prevent any further distal movement of the needle when the tab engages the proximal edge of the notch. To avoid difficulties in aligning the tab and the notch, the speed nut could be formed with a plurality of tabs, each of which is configured to engage the notch. Alternatively, the introducer needle could be formed with a plurality of longitudinally displaced notches located around the circumference of the introducer needle.

In still another embodiment of the lock that prevents distal movement of the sharp distal tip of the introducer needle out of the distal end of the needle shield once the sharp distal tip has been proximally withdrawn into the needle shield, a retention plate is located on a proximal face of a medial wall formed in the housing. The wall defines an opening therein that has a diameter large enough to allow the introducer needle and the discontinuous portion to pass through. The retention plate defines at least one, but preferably a plurality of radially inwardly directed tabs. A cut out portion that has a radius substantially equal to or slightly larger than the radius of the main portion of the introducer needle but less than the radius of the enlarged diameter portion is defined between the tabs. In this embodiment, the discontinuous portion is preferably an enlarged diameter portion with a distally facing shoulder. As the introducer needle is withdrawn into the needle shield, the main portion of the introducer needle rides past the retention plate with little or no interference. As the introducer needle moves proximally with respect to the needle shield, the enlarged diameter portion of the introducer needle engages the retention plate and the tabs flex proximally so the enlarged diameter portion can travel proximally past the retention plate. Once the enlarged diameter portion of the needle is proximal of the retention plate, the tabs return to their unflexed position and abut the proximal face of the medial wall. Any subsequent distal movement of the introducer needle is prevented when the enlarged diameter portion engages the tabs of the retention plate since the housing wall prevents the tabs from flexing distally out of the way of the enlarged diameter portion.

The means for preventing further proximal movement of the introducer needle once the sharp distal tip of the introducer needle has been proximally withdrawn into the needle shield may take a number of forms. For example, where the discontinuous portion is an enlarged diameter portion, the housing may include a proximal opening that has a diameter sufficient to allow the main portion of the introducer needle to extend therethrough but that is too small to allow the enlarged diameter portion of the introducer needle from passing therethrough. Alternatively, regardless of the configuration of the discontinuous portion of the introducer needle or where no discontinuous portion is used on the introducer needle, a tether connected to the needle hub and the needle shield could be used.

The needle shield also preferably includes a spring clip that connects the needle shield to the catheter hub and that maintains this connection until the sharp distal tip of the introducer needle has been withdrawn into the needle shield and locked in place. This spring clip can take many forms.

In one embodiment, the needle shield includes a spring clip that has a clip arm that engages the catheter hub. The spring clip is biased to a position where the clip arm does not engage the catheter hub. The spring clip is held in a biased position where the clip arm engages the catheter hub by the introducer needle shaft. Thus, as long as the introducer needle extends distally past the spring clip, the clip arm remains engaged with the catheter hub and the catheter hub stays connected with the needle shield. Once the sharp distal tip of the introducer needle is withdrawn proximally past the spring clip, the clip arm moves out of engagement with the catheter hub. This allows the catheter hub to be separated from the needle shield. This configuration ensures that the needle shield remains engaged with the catheter until the introducer needle has been completely removed from the catheter and is safely shielded in the needle shield.

The spring clip can be used in combination with any of the locks discussed above for preventing unwanted distal movement of the introducer needle with respect to the needle shield. In addition, the spring clip can be formed integrally with or separately from any of those locks.

The specific configuration of the spring clip can take many different forms and can be oriented in the housing in many different ways. For example, the spring clip can have a generally V or U shaped configuration. In this embodiment, the spring clip is located in the housing so it is perpendicular to the longitudinal axis of the introducer needle such that the V or U configuration is readily apparent from an end cross-sectional view of the needle shield. Thus one leg of the V is held in its biased position, adjacent to the other leg, by direct contact with the shaft of the introducer needle. In this arrangement, the spring clip includes a clip arm that extends generally parallel to the longitudinal axis of the introducer needle and engages a detent on the catheter hub that is oriented generally perpendicular to the longitudinal axis of the clip arm. When the introducer needle is withdrawn proximal of the spring clip, it returns to its unbiased position such that the clip arm moves transversely, i.e. generally perpendicularly to the longitudinal axis of the introducer needle, out of engagement with the catheter hub.

In an alternate embodiment, the spring clip is generally straight and is flexed into its biased position by the shaft of the introducer needle. In this embodiment, the clip arm has a hook configuration with one leg of the hook extending perpendicular to the longitudinal axis of the introducer needle with the hook facing distally. When the introducer needle is moved proximal of the spring clip, it returns to its unbiased position such that the clip arm moves transversely out of engagement with the catheter hub.

The spring clip can also be generally V or U shaped but oriented in the housing so it is aligned with the longitudinal axis of the introducer needle such that in a top cross-sectional view of the needle shield, the V or U configuration is apparent. In this configuration, the clip arm extends generally parallel to the longitudinal axis of the introducer needle and directly engages the catheter hub. However, a separate biasing arm extending generally perpendicular to the longitudinal axis of the introducer needle and connected to each of the legs of the V or U is required so the introducer needle can bias the spring clip into engagement with the catheter hub. Each biasing arm defines an opening therein and through which the introducer needle extends to achieve this biasing requirement. Once the introducer needle is moved proximal of the biasing arm, the legs of the spring clip can move to their unbiased position out of engagement with the catheter hub. Alternatively, the spring clip may be formed with only one leg such that the spring clip has a generally L-shaped shaped configuration.

Where the leaf spring uses a locking leg that is generally perpendicular to the introducer needle, the spring clip can be associated with the locking leg. The spring clip can be pivotally connected to the needle shield housing such that it is caused to pivoted between a clipped position and an unclipped position by the movement of the locking leg. Alternatively, the spring clip can be formed as a hook extending distally from the locking leg such that movement of the locking leg from the unshielded to the shielded position causes the hook to move from a clipped position to an unclipped position.

With the foregoing embodiments using a biasing arm, a means for minimizing drag on the introducer needle may be used. Such a means is a flap or finger extending from the opening in the biasing arm generally parallel to the longitudinal axis of the introducer needle. Alternatively, where two biasing arms are used, a pin and tether combination can be used. The pin extending through the biasing arms holds the openings in proper alignment so the introducer needle does not catch on the sides of the openings. A tether connected to the pin and the needle hub pulls the pin out of the biasing arms and allows the spring clip to return to its unbiased position.

Where two biasing arms are used, interlocking fingers may be located on the ends of the biasing arms such that, once the introducer needle is withdrawn proximal of the biasing arms, the interlocking fingers lock together to ensure that a non-defeatable transverse barrier is formed by the biasing arms.

In still another embodiment of the spring clip, the spring clip can be formed with a generally X shaped configuration. In this embodiment, the spring clip is oriented in the housing so the X shape is aligned with the longitudinal axis of the introducer needle such that in a top cross-sectional view of the needle shield, the X shape of the spring clip is apparent. In this embodiment, the introducer needle holds the distal portion of the legs of the X apart so they engage the inside of the catheter hub. Thus, once the introducer needle is withdrawn proximal of the intersection of the legs, the distal portion of the legs can move inwardly out of engagement with the catheter hub.

With all of the foregoing embodiments, the clip arm can be configured so it engages either the inside or the outside of the catheter hub. In addition, the clip arm can be configured frictionally or mechanically to engage the catheter hub. If a mechanical engagement is desired, the clip arm can have a detent thereon that engages a complementary detent formed on the catheter hub. Complementary detents can include, for example, a slot and a finger, or a post of any geometric shape. Regardless of the specific configuration used, the main requirement is to have the clip arm engage the catheter hub so it is difficult for the clinician to remove the catheter hub from the needle shield until the sharp distal tip of the introducer needle is shielded in the needle shield.

BRIEF DESCRIPTION OF THE DRAWINGS

The preferred embodiments are illustrated in the drawings in which like reference numerals refer to like elements and in which:

FIG. 3A is an enlarged elevation view of the distal portion of the introducer needle with one embodiment of the discontinuous portion thereon used in the catheter and introducer needle assembly with the needle shield of this invention;

FIG. 3B is an enlarged elevation view of the distal portion of the introducer needle with a second embodiment of the discontinuous portion thereon used in the catheter and introducer needle assembly with the needle shield of this invention;

FIG. 3C is an enlarged elevation view of the distal portion of the introducer needle with a third embodiment of the discontinuous portion thereon used in the catheter and introducer needle assembly with the needle shield of this invention;

FIG. 36B is a perspective view of a variation of the first embodiment of the spring clip shown in FIG. 36A that connects the needle shield to the catheter hub until the sharp distal tip of the introducer needle is locked in the needle shield;

FIG. 36C is a perspective view of still another variation of the first embodiment of the spring clip shown in FIG. 36 that connects the needle shield to the catheter hub until the sharp distal tip of the introducer needle is locked in the needle shield;

DETAILED DESCRIPTION OF THE INVENTION

Figure 1:
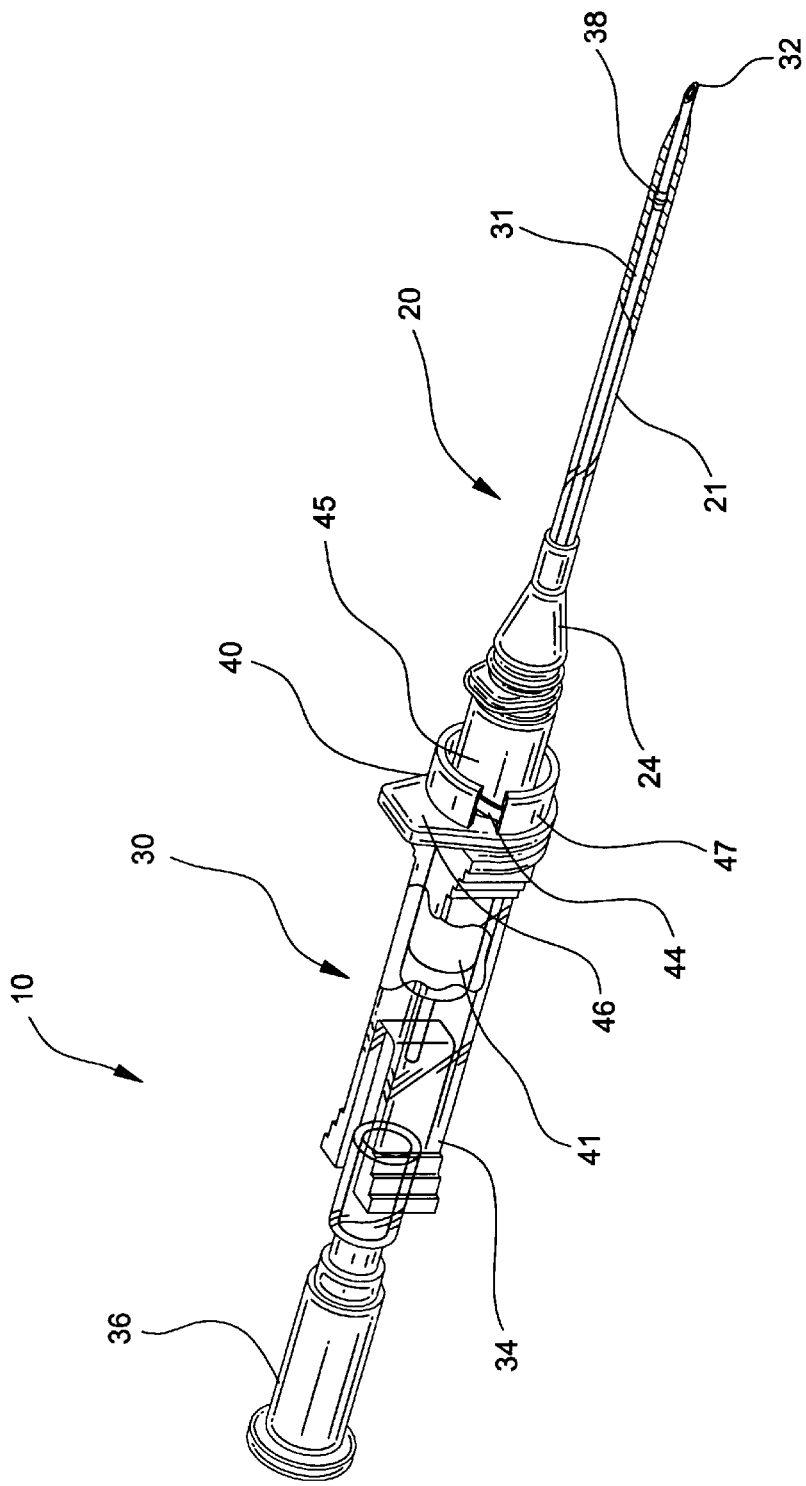
FIG. 1 is a perspective view of a standard catheter and introducer needle assembly with the needle shield of this invention with the catheter in partial cross-section.

As used herein, the term "proximal" refers to a location on the catheter and introducer needle assembly with the needle shield of this invention that, during normal use, is closest to the clinician using the device and farthest from the patient in connection with whom the device is used. Conversely, the term "distal" refers to a location on the catheter and introducer needle assembly of this invention that, during normal use, is farthest from the clinician using the device and closest to the patient in connection with whom the device is used.

As used herein, the term "top", "up" or "upwardly" refers to a location on the catheter and introducer needle assembly with the needle shield of this invention that, during normal use, is radially away from the longitudinal axis of the device and away from the patient's skin. Conversely, as used herein, the term "bottom", "down" or "downwardly" refers to a location on the catheter and introducer needle assembly with the needle shield of this invention that, during normal use, is radially away from the longitudinal axis of the device and toward the patient's skin.

As used herein, the term "in" or "inwardly" refers to a location with respect to the catheter and introducer needle assembly with the needle shield of this invention that, during normal use, is toward the inside of the device. Conversely, as used herein, the term "out" or "outwardly" refers to a location with respect to the catheter and introducer needle assembly with the needle shield of this invention that, during normal use, is toward the outside of the device.

This invention is described herein using like reference numbers for like elements in the different embodiments. Although this invention is described herein in connection with a typical peripheral IV catheter as well as a peripheral IV catheter with an integrated extension tube (an "integrated catheter"), it is to be understood that this invention is applicable to other catheters, For example, this invention is applicable to extended dwell catheters requiring the needle to be connected to the needle hub by a stylet as well as other medical devices where it is desirable for a needle to be shielded after use. In addition, while this invention is satisfied by embodiments in many different forms, there are shown in the drawings and herein-described in detail, preferred embodiments of the invention with the scope of the invention measured by the appended claims.

Figure 2:
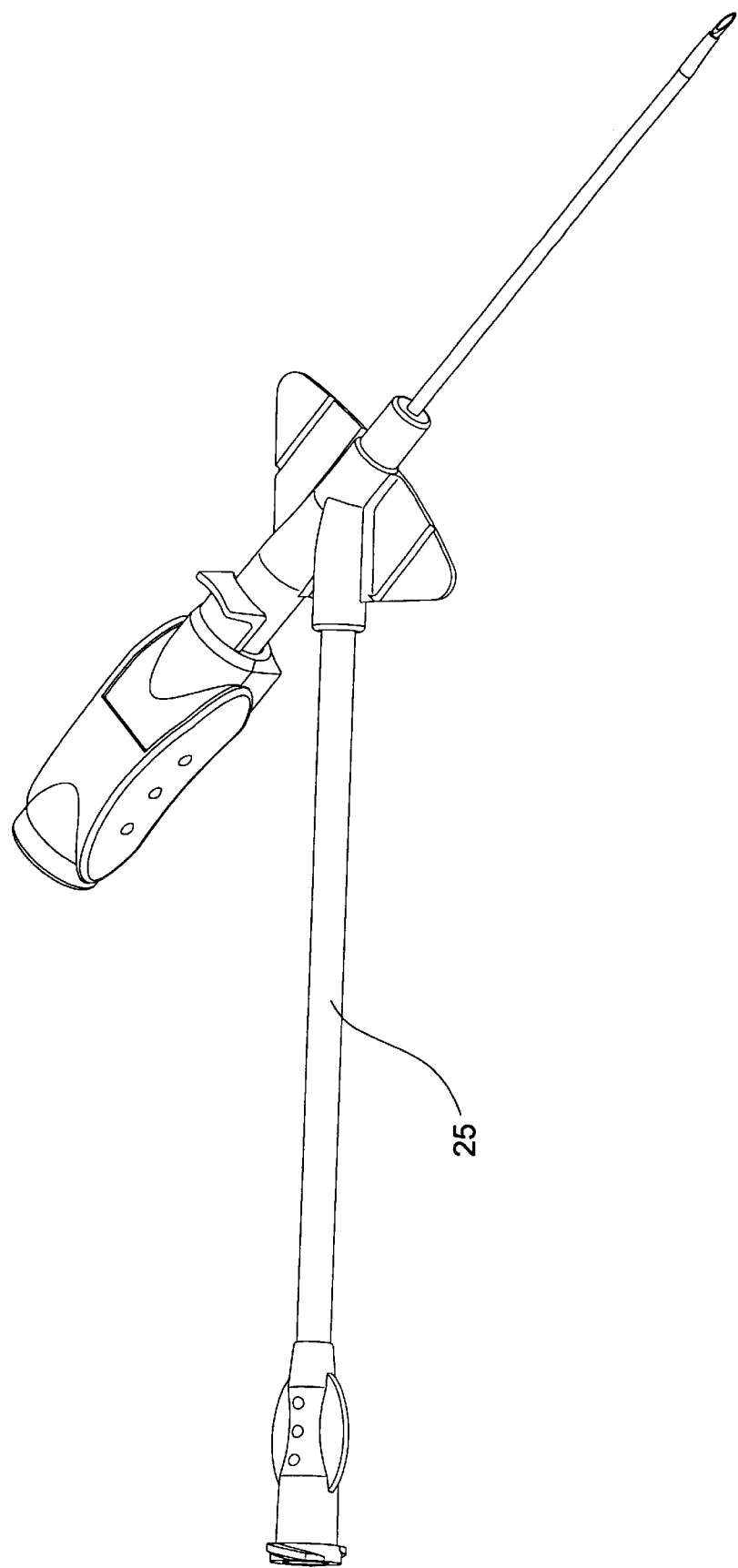
FIG. 2 is a perspective view of an integrated catheter and introducer needle assembly with the needle shield of this invention.

The catheter and introducer needle assembly of this invention is identified generally by the numeral 10 and defines a longitudinal axis extending therethrough. It includes a catheter assembly 20 and an introducer needle assembly 30 that includes a needle shield 40. See FIG. 1. Catheter assembly 20 may include an integrated extension tube 25. See FIG. 2. Such an integrated catheter is described generally in U.S. Pat. No. 5,697,914. As noted above, it is to be understood that the needle shield 40 of this invention can be used in connection with such an integrated catheter.

Catheter assembly 20 includes a catheter 21 that has a proximal end, a distal end and a catheter hub 24 affixed to catheter proximal end. Suitable materials for catheter 21 include, but are not limited to, thermoplastic resins such as fluorinated ethylene propylene (FEP), polytetrafluoroethylene (PTFE), polyurethane and the like. Preferably, catheter 21 is formed from a thermoplastic hydrophilic polyurethane that softens with exposure to physiological conditions present in the patient's body. Suitable materials for catheter hub 24 include, but are not limited to, thermoplastic polymeric resins such as polycarbonate, polystyrene, polypropylene and the like. Catheter hub 24 may include a radially outwardly extending tab, which is useful for advancing catheter 21 into the patient's blood vessel.

Introducer needle assembly 30 includes introducer needle 31 having a sharp distal tip 32 defined by a bevel and a proximal end connected to a needle hub 34. Introducer needle 31 is preferably formed from stainless steel and has a longitudinal axis that is generally parallel to the longitudinal axis of catheter and introducer needle assembly 10. Needle hub 34 can include an integrated flashback chamber having an open proximal end. Needle hub 34 may be formed from the same types of materials that are used to form catheter hub 24. Of course, other materials could be used to form needle hub 34. Preferably, the open proximal end is closed to fluid flow by a vented plug 36 which allows air but not fluid to flow therethrough.

Introducer needle assembly 30 also includes needle shield 40, which includes housing 41 defining an internal cavity 42 therein. Housing 41 also defines a proximal opening 43 and a distal opening 45 in communication with internal cavity 42. This allows introducer needle 31 to extend longitudinally through housing 41. The diameters of cavity 42, proximal opening 43 and distal opening 45 are at least slightly larger than the diameter of the main portion of introducer needle 31. This allows introducer needle 31 easily to pass through needle shield 40. Preferably, cavity 42 and distal opening 45 are at least slightly larger than any discontinuous portion formed on introducer needle 31 as described hereinafter. This: allows the distal portion of introducer needle 31 to be withdrawn into housing 41 but prevents introducer needle 31 from being withdrawn proximally from needle shield 40 as described hereinafter.

Where the spring clip, as described hereinafter, of this invention is not used, housing 41 may include a radially extending flange 46 and a plurality of longitudinally extending fingers 47. Fingers 47 may include radially inwardly directed projections 48. Fingers 47 and projections 48 engage catheter hub 24 to hold introducer needle assembly 30 together with catheter assembly 20. Typically, catheter hub 24 includes a radially projecting thread or ear 44 at its proximal end to facilitate the connection of another device thereto. This provides a portion of catheter hub 24 for fingers 47 and projections 48 to engage so that catheter hub 24 and introducer needle assembly 30 remain connected until introducer needle 31 is removed from catheter assembly 20 and is shielded by needle shield 40.

Introducer needle 31 includes a discontinuous portion formed thereon along a distal portion thereof. The discontinuous portion may take many forms. For example, it can be an enlarged diameter portion 38, see FIGS. 3A, 3B, 3C and 3G, or a notch 39, see FIGS. 3D and 3G, or a combination of an enlarged diameter portion 38 and a notch 39, see FIGS. 3E, 3F and 3G. Where the discontinuous portion 38 is an enlarged diameter portion, the proximal portion 38a may be tapered and the distal portion 38b may be a distally facing shoulder oriented generally perpendicular to the longitudinal axis of introducer needle 31. See e.g. FIG. 3A. Alternatively, distal portion 38b could be tapered. See e.g. FIG. 3C. This taper can be at just about any angle between almost parallel to and perpendicular to the longitudinal axis of introducer needle. Preferably, enlarged diameter portion 38, such as shown in FIGS. 3A, 3C, 3F and 3G, is formed on introducer needle 31 by centerless grinding a larger diameter introducer needle. Although enlarged diameter portion 38 is shown in the FIGS. as being circumferentially disposed about the shaft of introducer needle 31, it is to be understood, that enlarged diameter portion 38 could be formed asymmetrically about the shaft of introducer needle 31. For example, enlarged diameter portion could be formed as a crimped portion on introducer needle 31. See FIGS. 3B and 3E. For the avoidance of doubt, as used herein the term diameter refers to the length of a straight line passing through the center of an object.

Where the discontinuous portion that is used for introducer needle 31 is enlarged diameter portion 38, it should have a diameter greater than the diameter of proximal opening 43 regardless of the specific configuration used for enlarged diameter portion 38. This provides one mechanism to ensure that introducer needle 31 cannot be pulled in a proximal direction completely out of needle shield 40. This is because enlarged diameter portion 38 blocks further proximal movement of introducer needle 31 through proximal opening 43. Alternatively, a washer 49 having an opening therein with a diameter slightly larger than the diameter of the main portion of introducer needle 31 but smaller than the diameter of enlarged diameter portion 38 can be placed into cavity 42 abutting the proximal wall of cavity 42. In this position, the opening of washer 49 is aligned with proximal opening 43. Thus washer 49 would prevent enlarged diameter portion 38 from passing through proximal opening 43.

Figure 42:
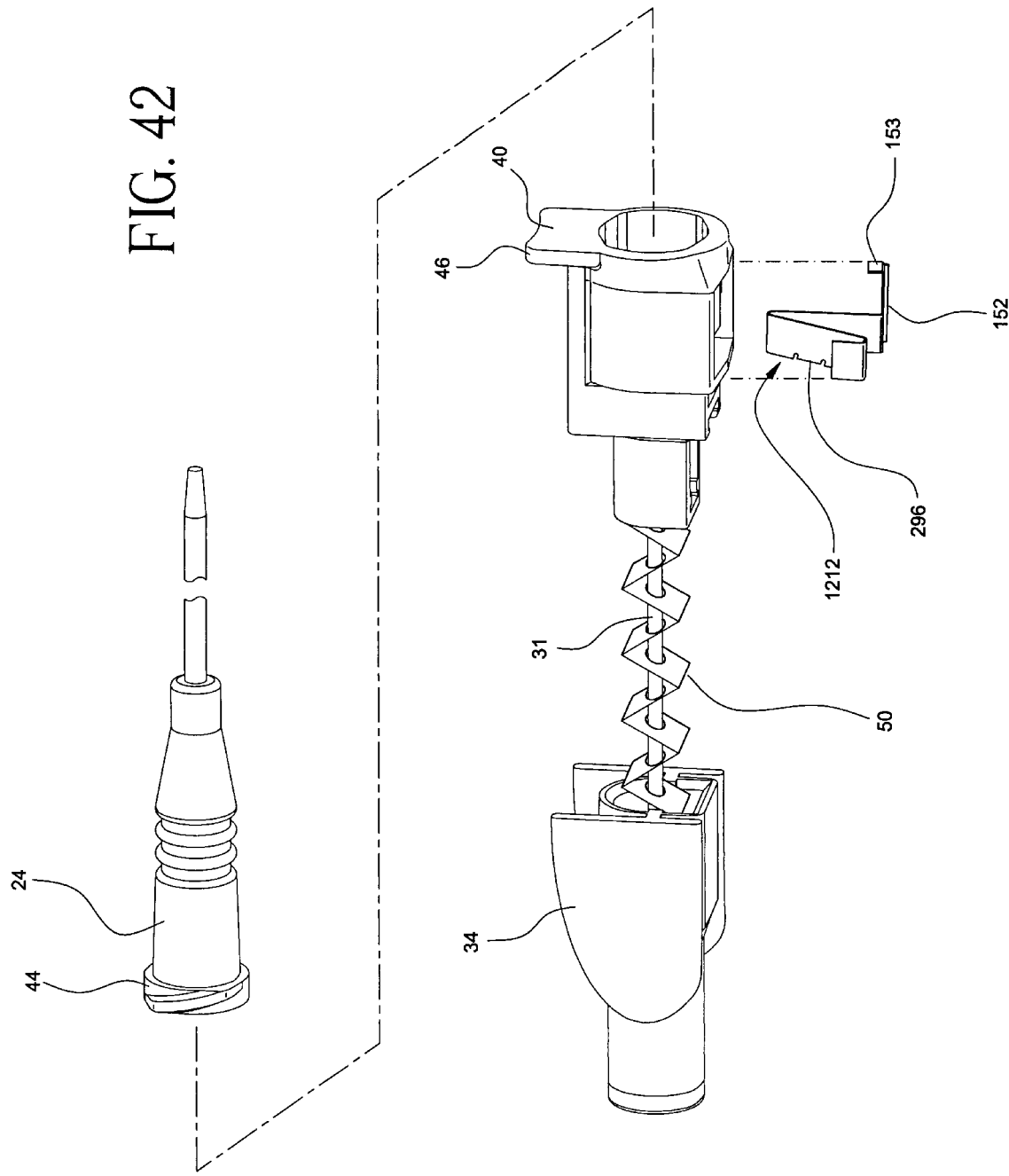
FIG. 42 is an exploded perspective view of a catheter, introducer needle, tether and the needle shield with a second embodiment of a spring clip with a transverse barrier that connects the needle shield to the catheter hub until the sharp distal tip of the introducer needle is locked in the needle shield.
Figure 43:
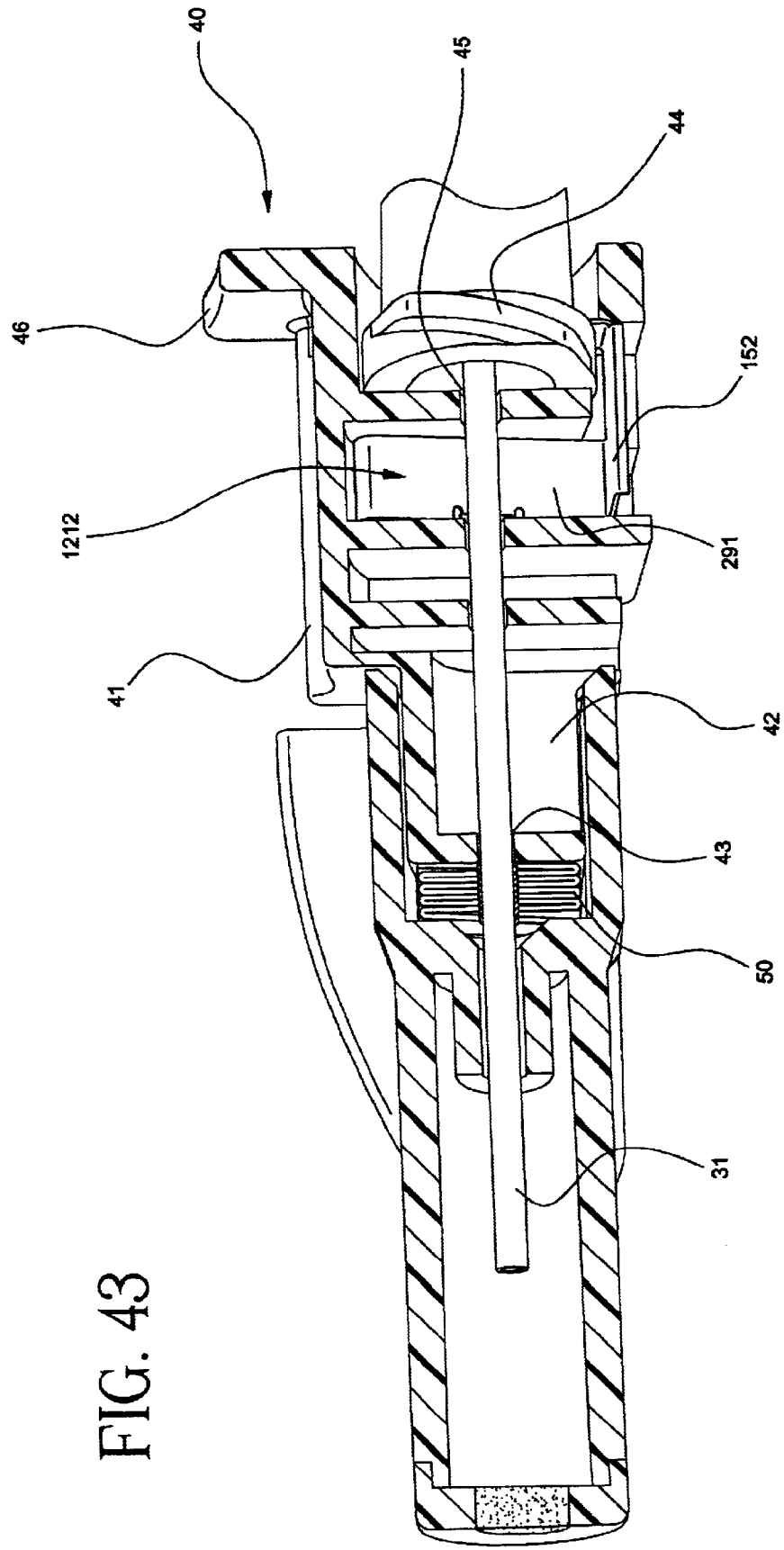
FIG. 43 is a cross-sectional view of the needle shield with the second embodiment of the spring clip with a transverse barrier that connects the needle shield to the catheter hub until the sharp distal tip of the introducer needle is locked in the needle shield, a portion of the introducer needle, the tether, the needle shield, and the proximal portion of the catheter hub with the sharp distal tip of the introducer needle extending from the distal end of the needle shield and the needle shield connected to the catheter hub.
Figure 44:
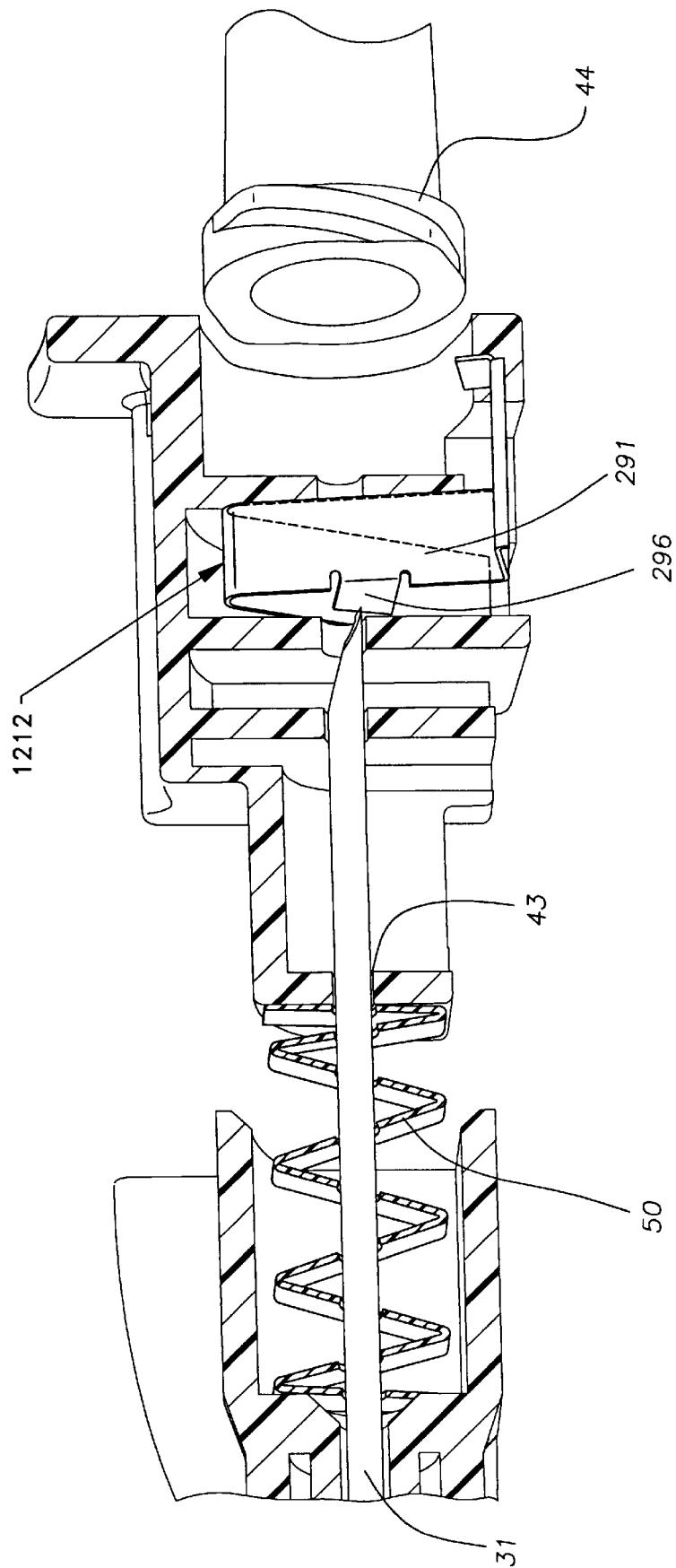
FIG. 44 is a cross-sectional view of the needle shield with the second embodiment of the spring clip with a transverse barrier that connects the needle shield to the catheter hub until the sharp distal tip of the introducer needle is locked in the needle shield, the distal portion of the needle hub, the distal portion of the introducer needle, the tether, and the proximal portion of the catheter hub with the sharp distal tip of the introducer needle locked in the needle shield and the needle shield disconnected from the catheter hub.
Figure 45:
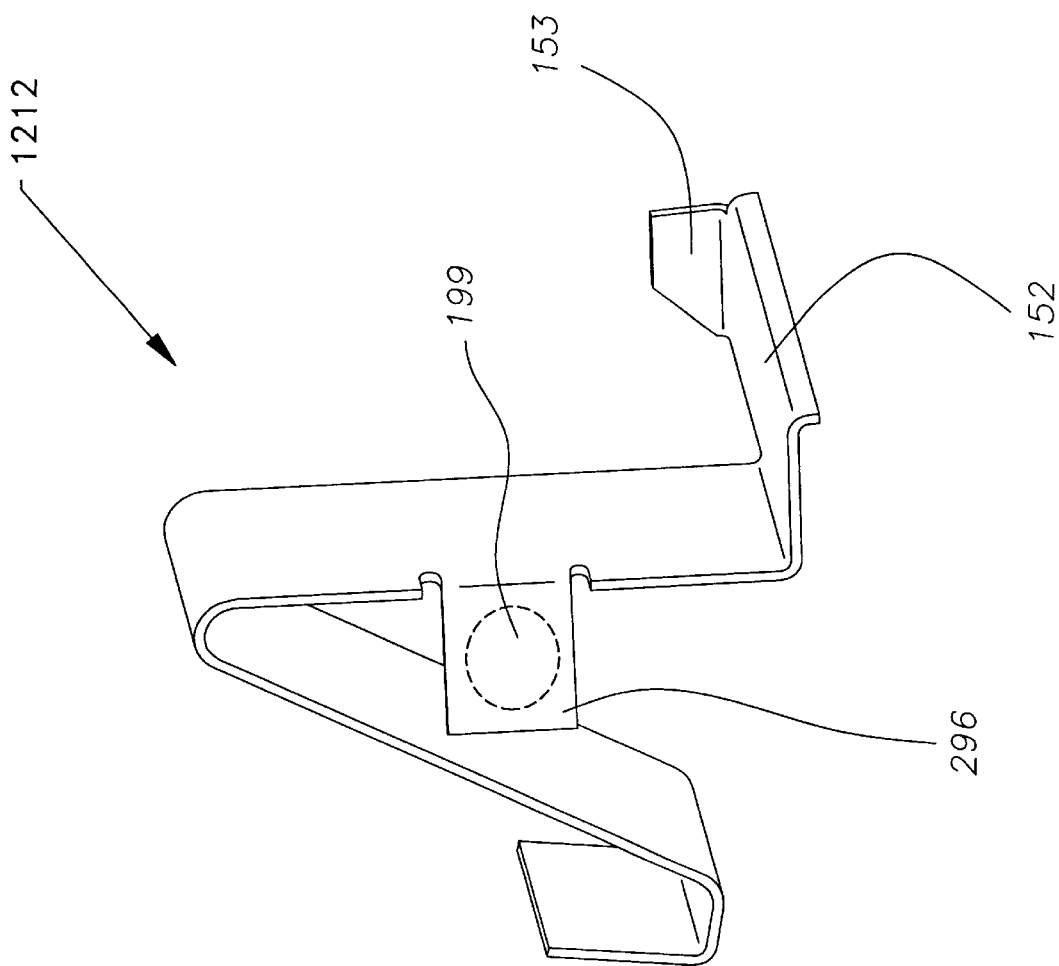
FIG. 45 is a perspective view of the second embodiment of the spring clip with a transverse barrier shown in FIGS. 42 through 44.
Figure 46:
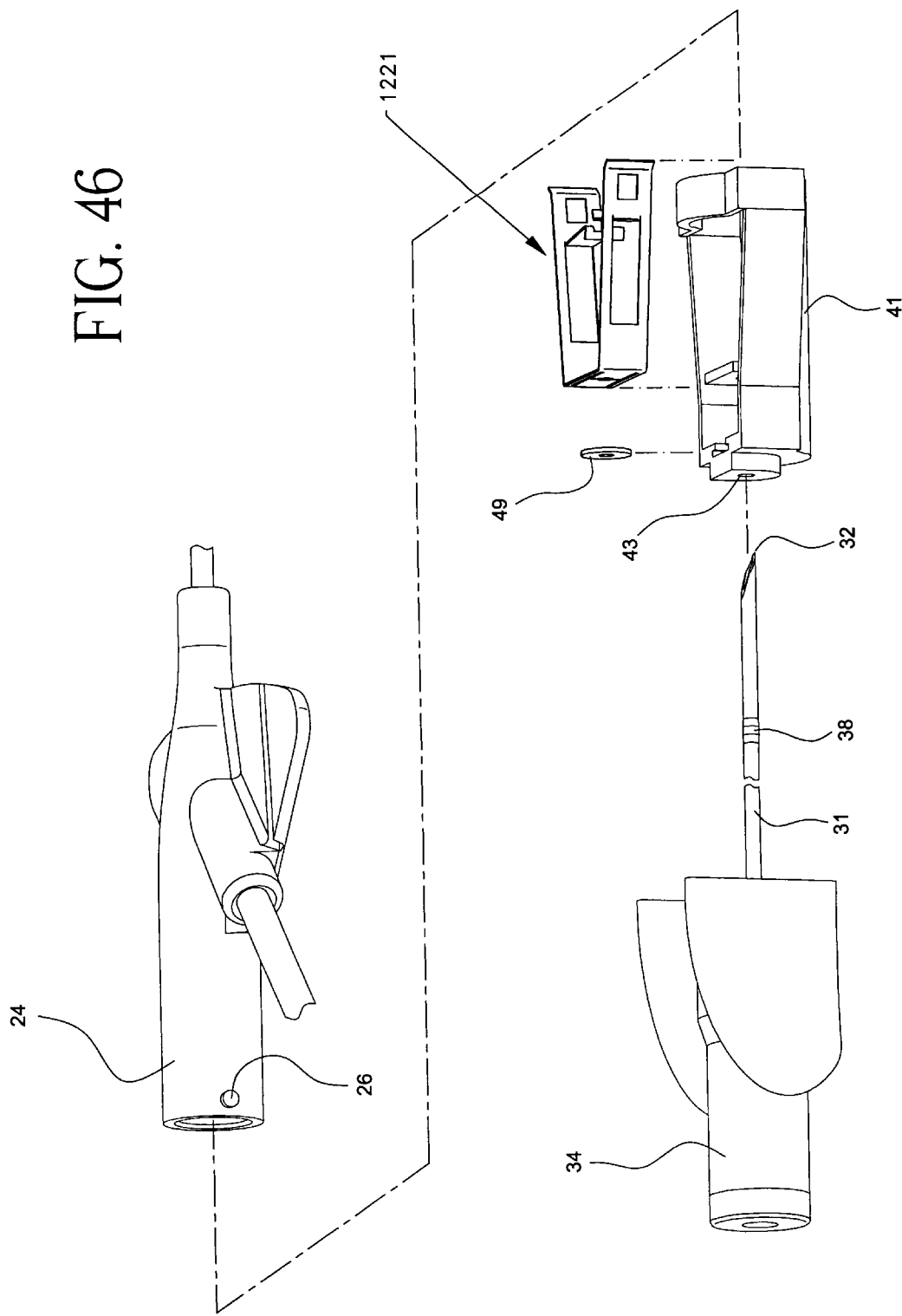
FIG. 46 is an exploded perspective view of an integrated catheter, an introducer needle and the needle shield with a first embodiment of an integrated clip lock that connects the needle shield to the catheter hub until the sharp distal tip of the introducer needle is locked in the needle shield and that prevents unwanted distal movement of the introducer needle.
Figure 47:
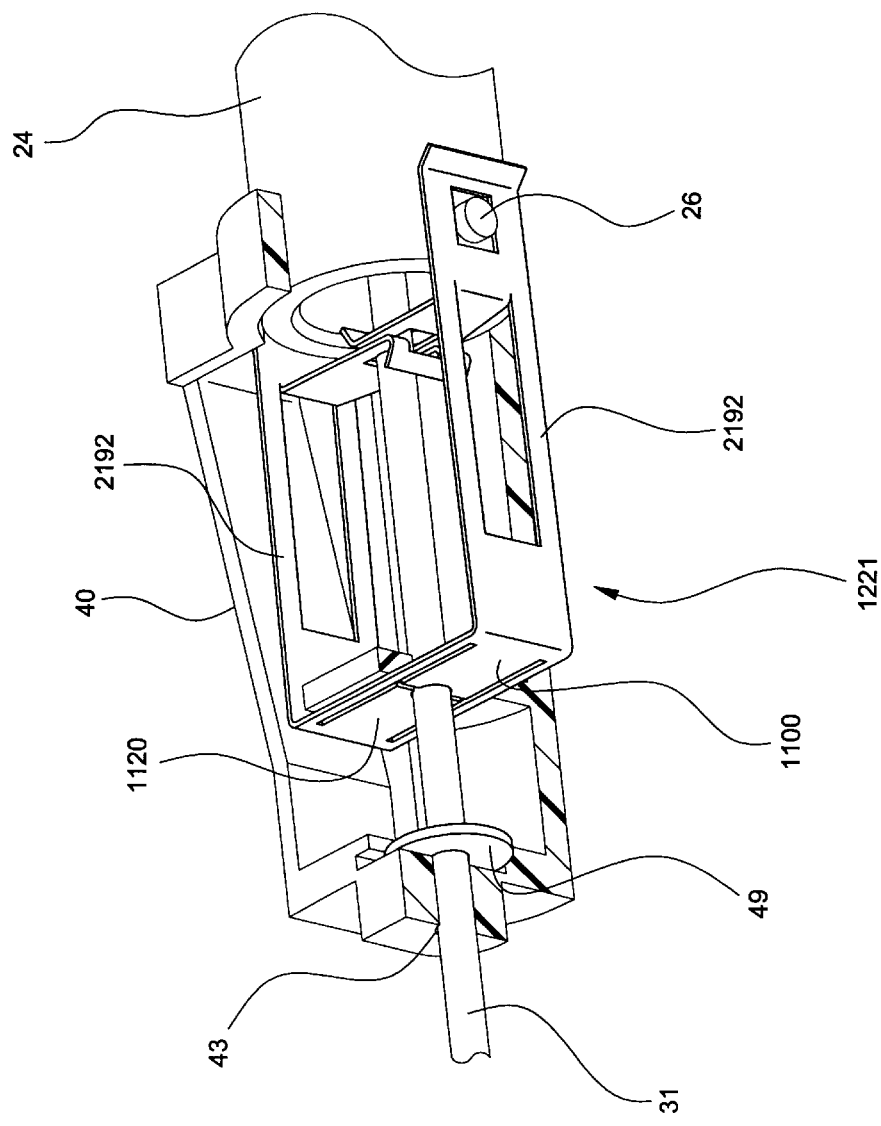
FIG. 47 is a perspective partial cross-sectional view of the needle shield with the first embodiment of the integrated clip lock that connects the needle shield to the catheter hub until the sharp distal tip of the introducer needle is locked in the needle shield and that prevents unwanted distal movement of the introducer needle, a portion of the introducer needle and the proximal portion of the catheter hub with the sharp distal tip of the introducer needle extending from the distal end of the needle shield and the needle shield connected to the catheter hub.
Figure 48:
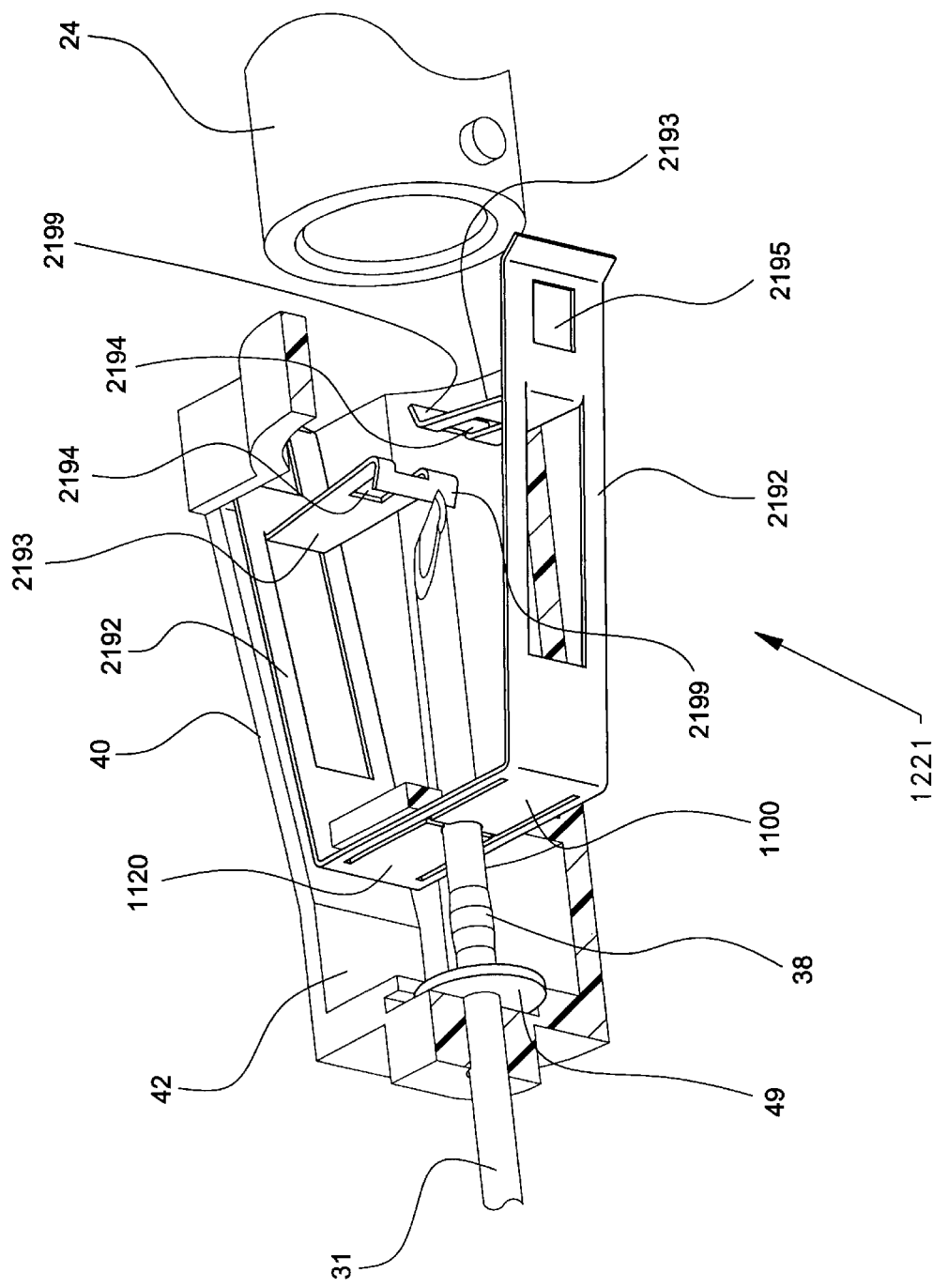
FIG. 48 is a perspective partial cross-sectional view of the needle shield with the first embodiment of the integrated clip lock that connects the needle shield to the catheter hub until the sharp distal tip of the introducer needle is locked in the needle shield and that prevents unwanted distal movement of the introducer needle, the distal portion of the introducer needle and the proximal portion of the catheter hub with the sharp distal tip of the introducer needle locked in the needle shield and the needle shield disconnected from the catheter hub.
Figure 49:
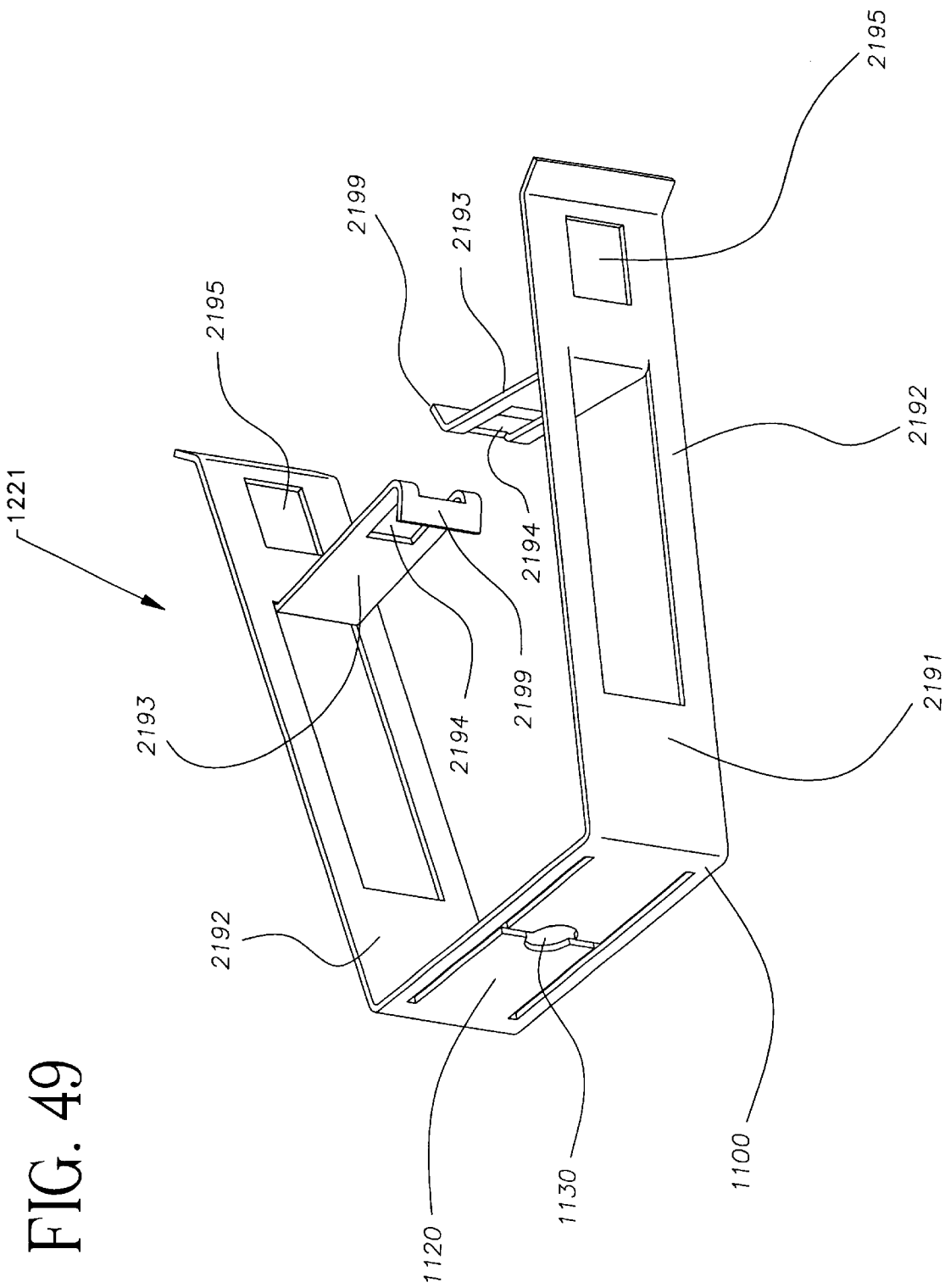
FIG. 49 is a perspective view of the first embodiment of the integrated clip lock that is shown in FIGS. 46 through 48 that connects the needle shield to the catheter hub until the sharp distal tip of the introducer needle is locked in the needle shield and that prevents unwanted distal movement of the introducer needle.

Alternatively, if notch 39 were used as the discontinuous portion or if no discontinuous portion were used on introducer needle, a tether 50 could be used to connect needle shield 40 with needle hub 34. See for example FIG. 42. Tether 50 must be configured such that its effective length will not allow sharp distal tip 32 to be pulled proximally completely out of needle shield 40.

The diameter of enlarged diameter portion 38 preferably should be at least about 0.002 inches greater than the outside diameter of the main portion of introducer needle 31. It has been surprisingly found that this dimension is sufficient, in the context of this invention, to prevent sharp distal tip 32 of introducer needle 31 from being moved distally out of needle shield 40 after sharp distal tip 32 has been withdrawn proximally into needle shield 40. Where enlarged diameter portion 38 is symmetrically disposed about the shaft of introducer needle 31, preferably the diameter of enlarged diameter portion 38 should be about 0.004 inches greater than the diameter of the main portion of introducer needle 31. To ensure this difference in diameter is achieved, that portion of introducer needle 31 immediately distal to distal portion 38b can be formed with a slightly increasing taper from distal portion 38b toward the distal end of introducer needle 31. See FIG. 3A. Grinding that portion of introducer needle 31 can form this taper immediately distal of distal portion 38b.

The lock that prevents unwanted distal movement of sharp distal tip 32 of introducer needle 31 out of the distal end of needle shield 40 once sharp distal tip 32 has been proximally withdrawn into needle shield 40 can take many forms. As used herein the phrase "unwanted distal movement of introducer needle 31" means distal movement of introducer needle 31, during normal use of catheter and introducer needle assembly 10 and under normal circumstances, such that sharp distal tip 32 is not re-exposed from distal opening 45 of needle shield 40 after the lock engages introducer needle 31.

As shown in FIGS. 4 through 7, the lock can be in the form of a spring gate 100, which can include a separate biasing mechanism 150, to lock introducer needle 31 in place in needle shield 40. In this embodiment for the lock, the discontinuous portion is preferably an enlarged diameter portion 38.

Spring gate 100 and biasing mechanism 150 are located in cavity 42 of housing 41 of needle shield 40 and about introducer needle 31. Spring gate 100 has a pair of spaced apart tines 110 connected by a base 120. Tines 110 should define at least one portion having a distance therebetween that is slightly larger than the diameter of the main portion of introducer needle 31 and is less than the diameter of enlarged diameter portion 38. This allows the main portion of introducer needle 31 to be positioned between tines 110 and move proximally past tines 110. Base 120 may extend generally perpendicular to tines 110 to provide more surface area to contact biasing mechanism 150, described below. Although the face of spring gate 100 is shown in the FIGS. as having a generally U-shape, it is to be understood that other shapes could be used for the face of spring gate 100 as long as the shape allows at least one tine 110 to engage enlarged diameter portion 38. For example, the face of spring gate 100 could have a V-shape or an L-shape.

Figure 4:
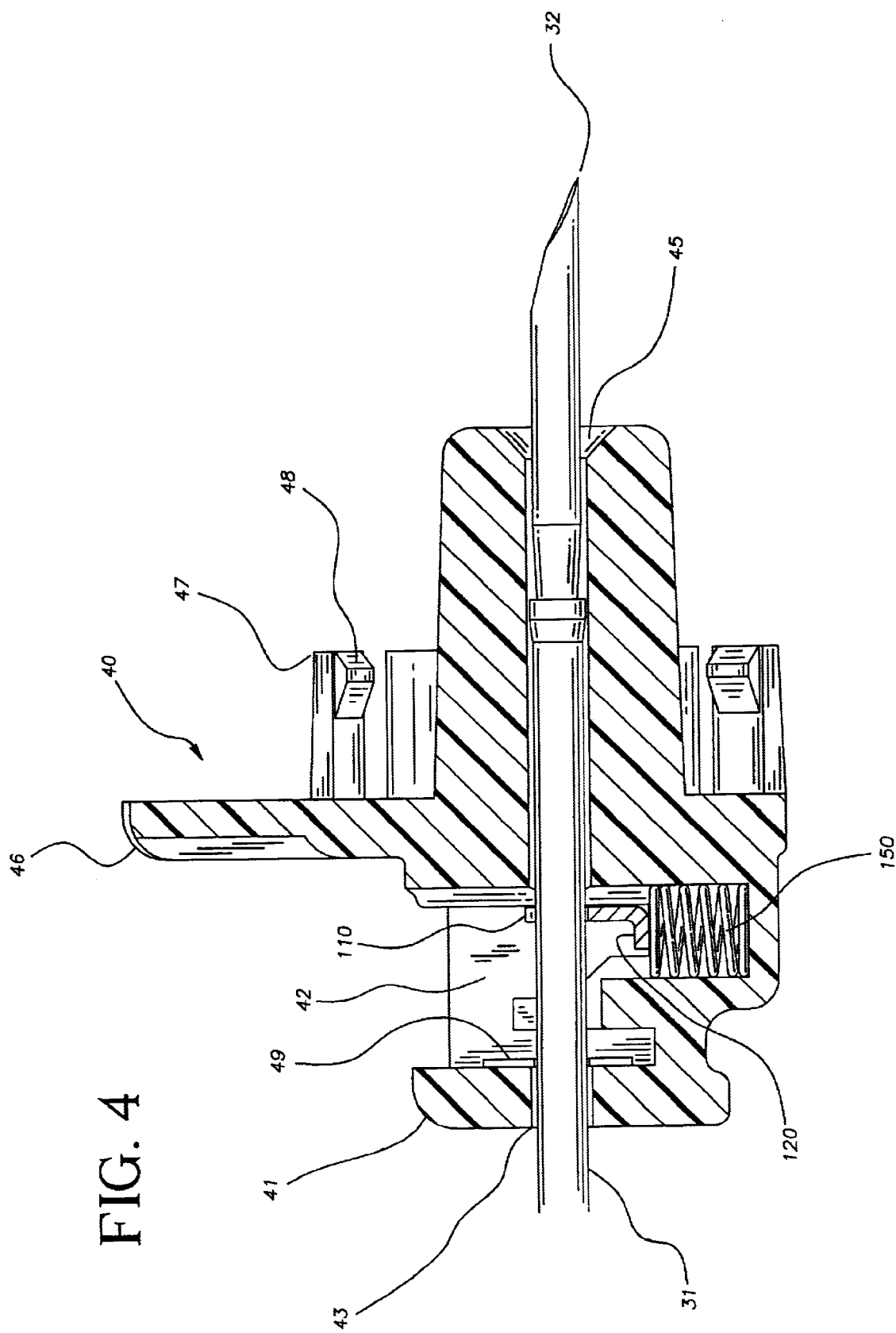
FIG. 4 is a cross-sectional view of the needle shield with a first embodiment of the lock that prevents unwanted distal movement of the introducer needle and the distal portion of the introducer needle with the sharp distal tip of the introducer needle extending from the distal end of the needle shield.
Figure 5:
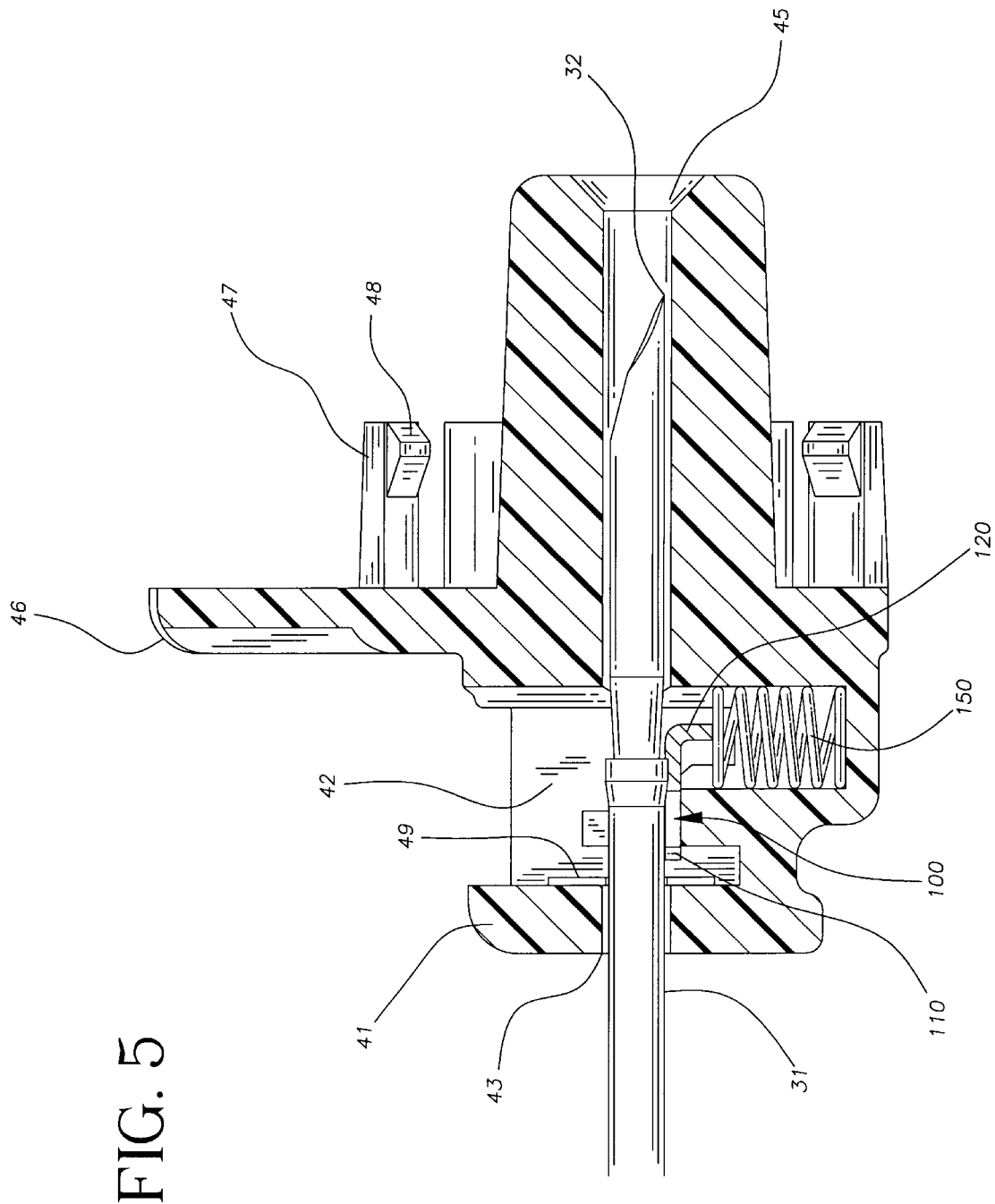
FIG. 5 is a cross-sectional view of the needle shield with the first embodiment of the lock that prevents unwanted distal movement of the introducer needle and the distal portion of the introducer needle with the sharp distal tip of the introducer needle withdrawn into the needle shield.
Figure 6:
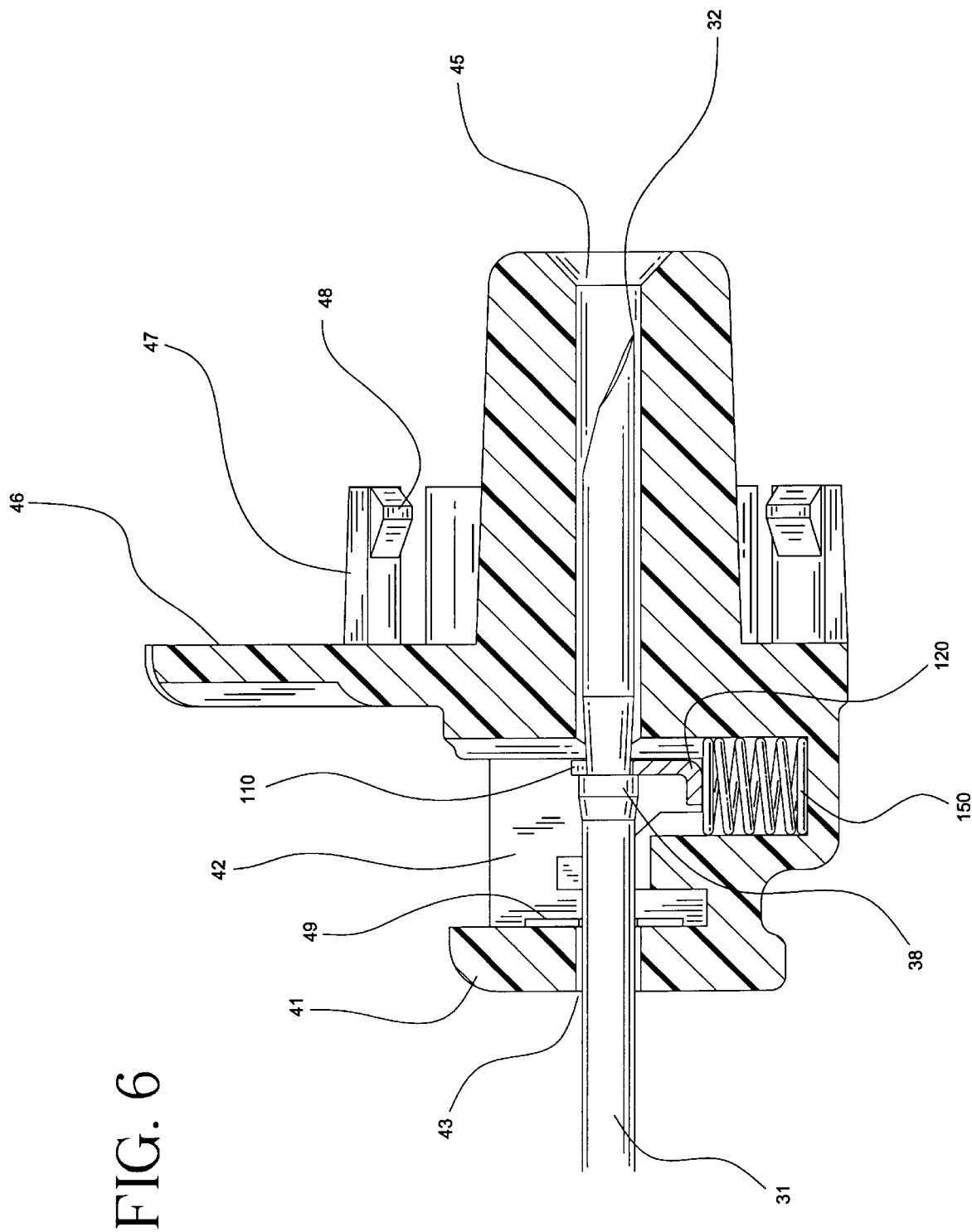
FIG. 6 is a cross-sectional view of the needle shield with the first embodiment of the lock that prevents unwanted distal movement of the introducer needle and the distal portion of the introducer needle with the sharp distal tip of the introducer needle locked in the needle shield.
Figure 7:
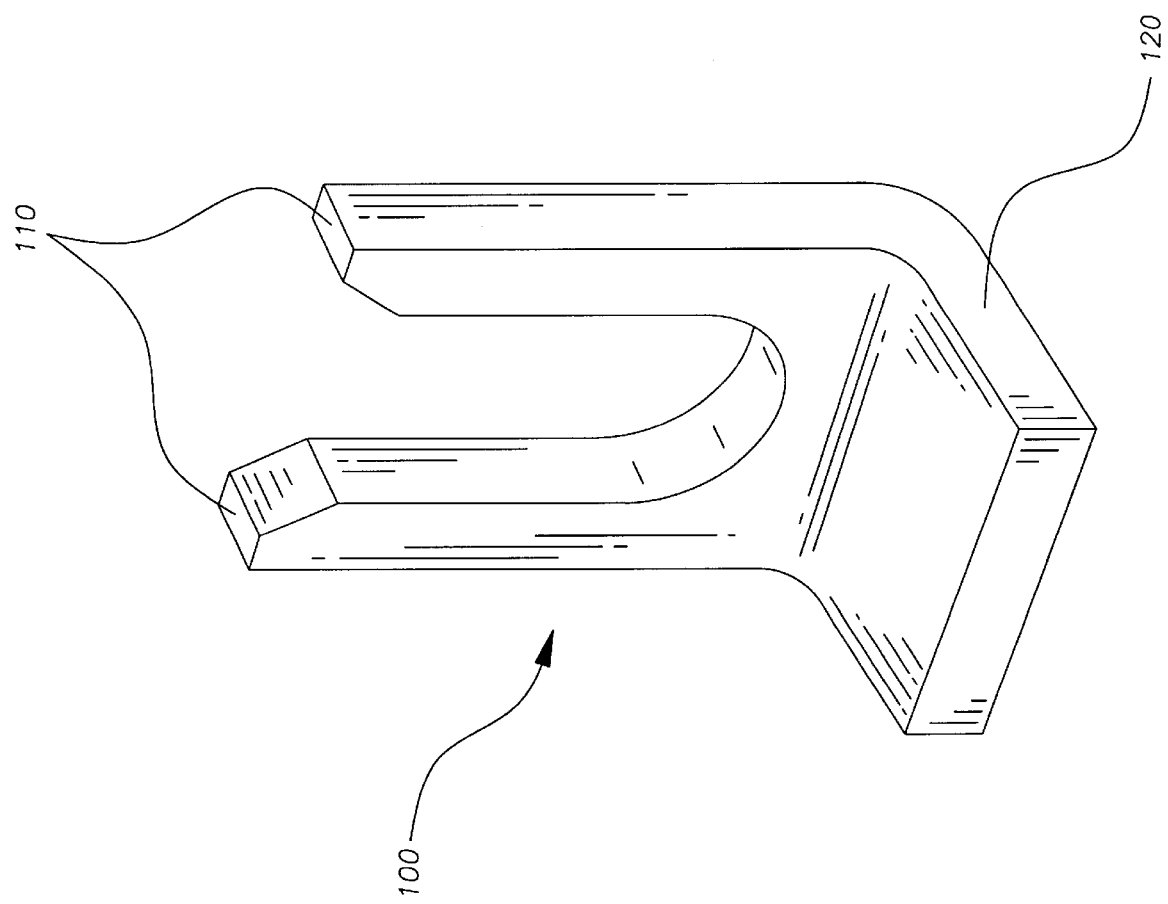
FIG. 7 is a perspective view of the spring gate that is used in the first embodiment of the lock shown in FIGS. 4 through 6 that prevents unwanted distal movement of the introducer needle.

Biasing mechanism 150 forces spring gate 100 up into contact with introducer needle 31 and ensures that tines 110 and base 120 remain adjacent to introducer needle 31. Biasing mechanism 150 may take any appropriate form. For example, it may be a helical spring as shown in FIGS. 4 through 6, or it may be a compressible rubber-like material that acts as a spring or it may be configured as a leaf spring. Moreover, biasing mechanism 150 and tines 110 could be integrated as one member.

As introducer needle 31 is withdrawn proximally into needle shield 40, the main portion of introducer needle 31 passes between tines 110. When enlarged diameter portion 38 abuts tines 110, spring gate 110 is rotated proximally and forced downwardly against the bias of biasing mechanism 150 by the proximal movement of enlarged diameter portion 38. This allows enlarged diameter portion 38 to pass proximally past tines 110. Compare FIGS. 4 and 5. Once enlarged diameter portion 38 is proximal of tines 110, biasing mechanism 150 forces spring gate 100 to rotate clockwise, as seen in the FIGS, back into engagement with introducer needle 31. When enlarged diameter portion 38 is proximal of tines 110, sharp distal tip 32 is proximal of distal opening 45. See FIG. 6. Similarly, all of the embodiments disclosed herein are configured such that sharp distal tip 32 is locked in needle shield 40 proximal of distal opening 45.

Subsequent distal movement of introducer needle 31 is prevented by the engagement of enlarged diameter portion 38 and tines 110. Since tines 110 engage the distal wall of cavity 42, tines 110 cannot be moved distally past this distal wall. Thus, if a clinician tries to advance introducer needle 31 distally after enlarged diameter portion 38 has been moved proximal of tines 110, enlarged diameter portion 38 would butt up against tines 110 which in turn would butt up against the distal wall of cavity 42. Biasing mechanism 150 ensures that tines 110 remain engaged to introducer needle 31. And as discussed above, further proximal movement of introducer needle 31 from needle shield 40 is prevented because enlarged diameter portion 38 blocks further proximal movement of introducer needle 31 through proximal opening 43 or washer 49. Alternatively, a tether 50 connecting needle shield 40 and needle hub 34 could be used to prevent unwanted proximal movement of introducer needle 31 out of needle shield 40.

A second embodiment for the lock that prevents unwanted distal movement of introducer needle 31 is a leaf spring 200. See FIGS. 8 through 10. Leaf spring 200 has a proximal wall 210 defining an opening 215 therein aligned with proximal opening 43 of cavity 42. Proximal wall 210 is generally perpendicular to the longitudinal axis of introducer needle 31. Where enlarged diameter portion 38 is used on introducer needle 31, preferably opening 215 has a diameter at least slightly larger than the diameter of the main portion of introducer needle 31 but smaller than the diameter of enlarged diameter portion 38. Of course, it is not necessary for leaf spring 200 to include proximal wall 210 and opening 215 as long as proximal opening 43, washer 49 or tether 50 is used to prevent proximal movement of sharp distal tip 32 out of needle shield 40.

Figure 8:
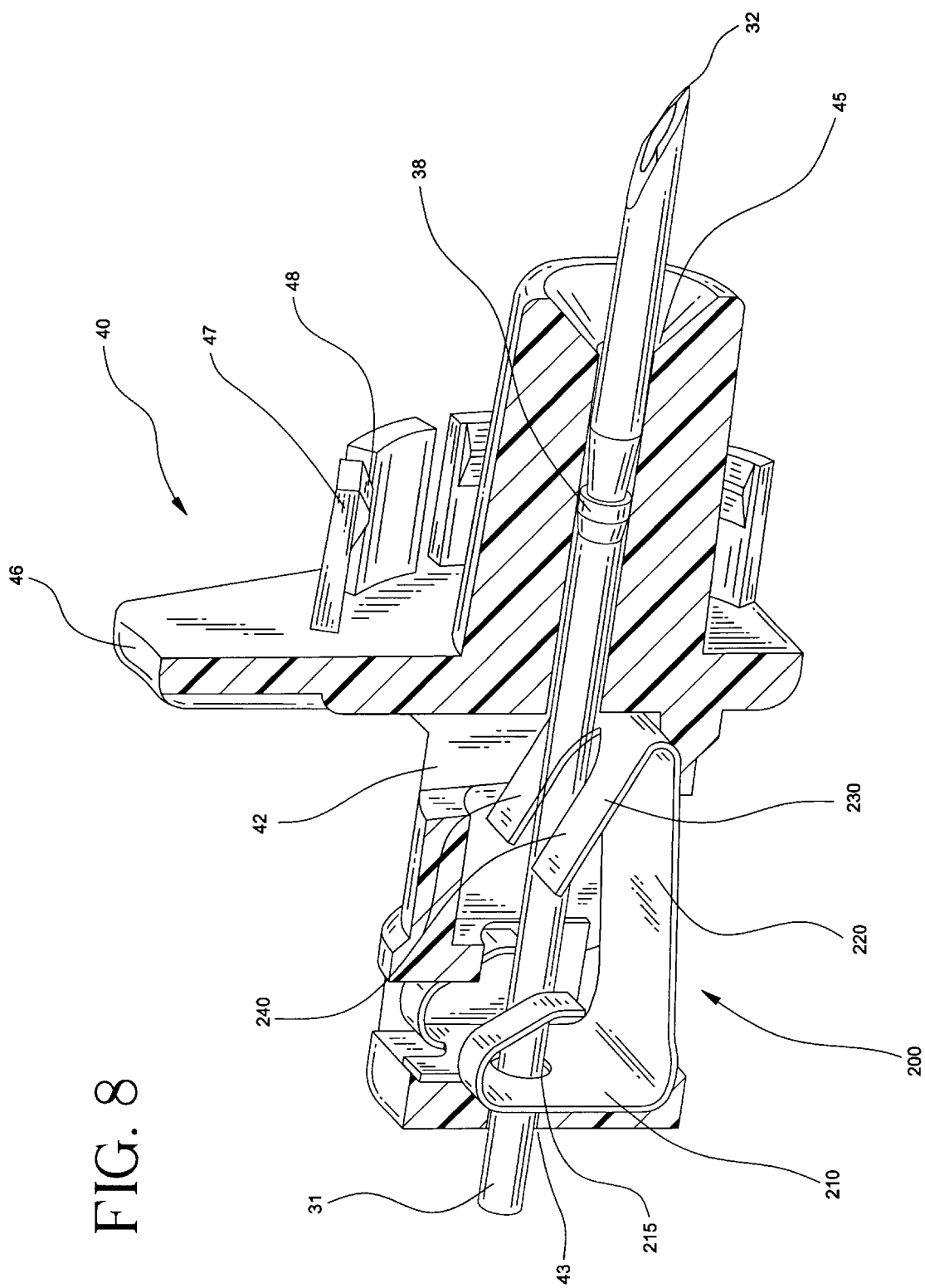
FIG. 8 is a perspective cross-sectional view of the needle shield with a second embodiment of the lock that prevents unwanted distal movement of the introducer needle and the distal portion of the introducer needle with the sharp distal tip of the introducer needle extending from the distal end of the needle shield.
Figure 9:
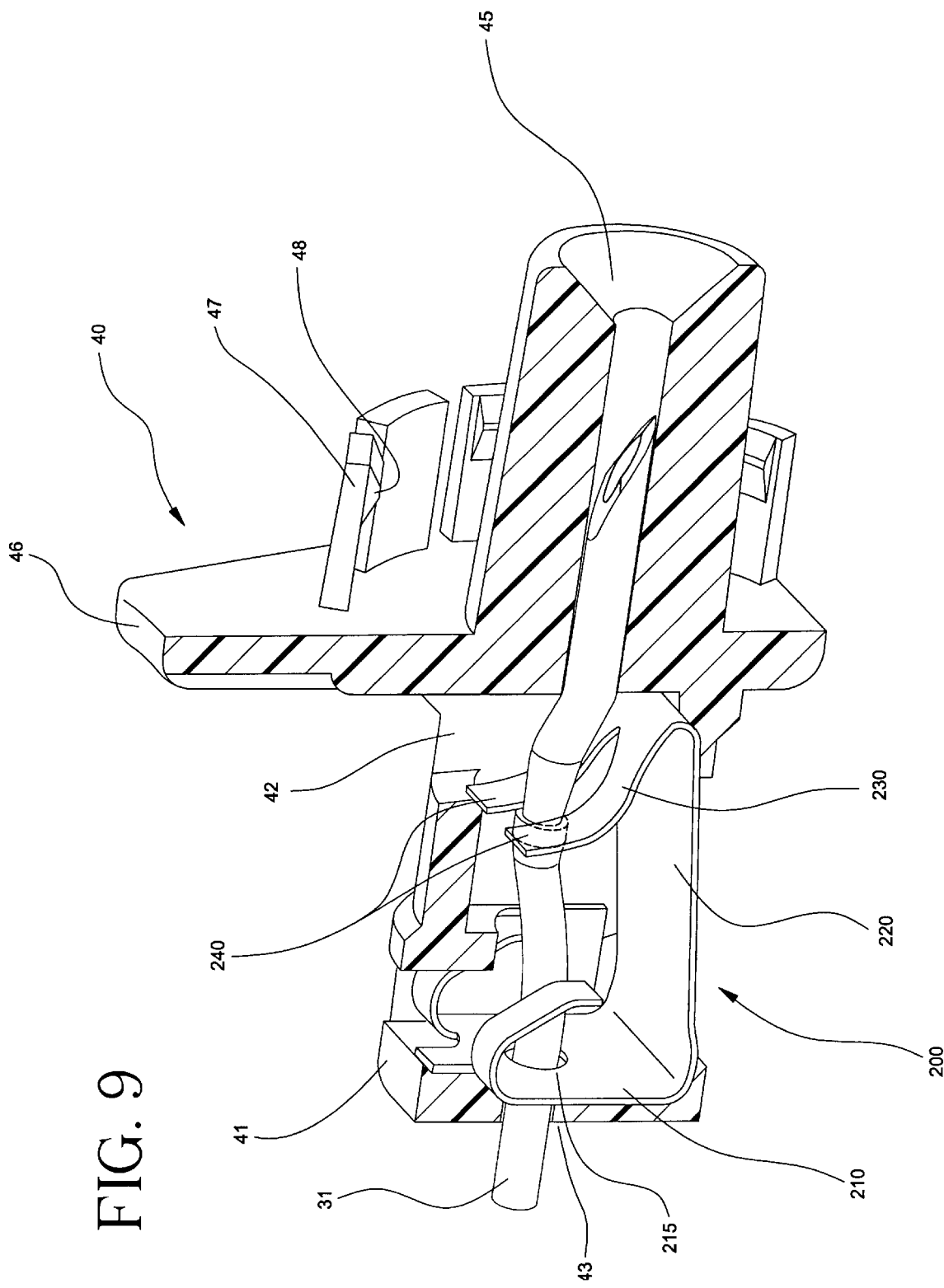
FIG. 9 is a cross-sectional view of the needle shield with the second embodiment of the lock that prevents unwanted distal movement of the introducer needle and the distal portion of the introducer needle with the sharp distal tip of the introducer needle locked in the needle shield.
Figure 10:
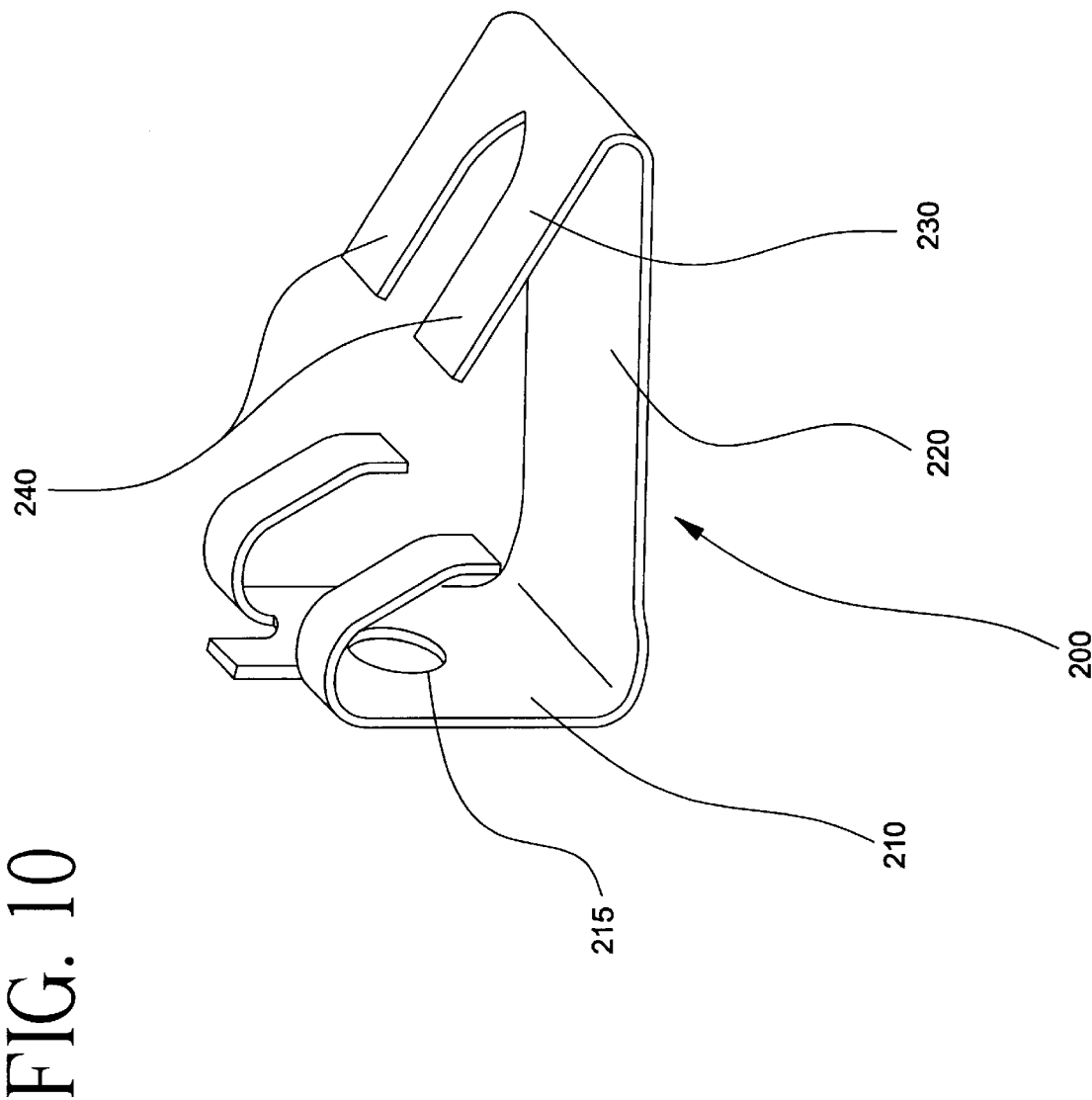
FIG. 10 is a perspective view of the leaf spring that is the second embodiment of the lock shown in FIGS. 8 and 9 that prevents unwanted distal movement of the introducer needle.

Leaf spring 200 also has a support leg 220 and a locking leg 230 oriented at an angle to support leg 220 such that locking leg 230 is directed generally toward proximal wall 210 so that locking leg 230 is preferably not perpendicular to support leg 220. Preferably, locking leg 230 approaches being parallel to support leg 220. As seen in FIGS. 8–10 support leg 220 and locking leg 230 are preferably-oriented to each other such that leaf spring 200 has a generally V-shape lying on its side, with the apex of the V facing distally. This V-shaped configuration ensures that locking leg 230 is biased toward introducer needle 31 and is oriented at an angle to support leg 220.

Locking leg 230 includes a pair of spaced apart tines 240. Along at least one portion of tines 240, a distance is defined therebetween that is slightly larger than the diameter of the main portion of introducer needle 31 and is less than the diameter of enlarged diameter portion 38. This allows the main portion of introducer needle 31 to extend between tines 240 and move proximally past tines 240. Tines 240 are preferably oriented on locking leg 230 so as to assume a generally V-shaped configuration.

As introducer needle 31 is withdrawn proximally into needle shield 40, the main portion of introducer needle 31 passes between tines 240. When enlarged diameter portion 38 abuts tines 240, they are rotated counterclockwise, as seen in the FIGS. This allows enlarged diameter portion 38 to move proximally past tines 240. Once enlarged diameter portion 38 is proximal of tines 240, the bias of leaf spring 200 causes locking leg 230 and tines 240 to rotate clockwise, as seen in the FIGS. back into engagement with introducer needle 31. If introducer needle 31 is subsequently moved distally, locking leg 230 and tines 240 will continue to rotate clockwise, as seen in the FIGS. This forces introducer needle 31 upwardly into tight engagement with the walls defining cavity 42 of needle shield 40 and prevents re-exposure of sharp distal tip 32. Any subsequent distal movement of introducer needle 31 is prevented and, if enough distally directed force is applied to introducer needle 31, could cause introducer needle 31 to buckle and permanently lock introducer needle 31 in needle shield 40. See FIG. 9.

Further proximal movement of introducer needle 31 is prevented by the engagement of enlarged diameter portion 38 with proximal wall 210. Again, if desired, a tether 50 connecting needle shield 40 to needle hub 34 could be used to prevent this unwanted proximal movement of introducer needle 31 with respect to needle shield 40.

A third embodiment for the lock that prevents unwanted distal movement of introducer needle 31 is a leaf spring 300. See FIGS. 11 through 13. Leaf spring 300 has a proximal wall 310 defining an opening 315 therein aligned with proximal opening 43 of cavity 42. Proximal wall 310 is generally perpendicular to the longitudinal axis of needle shield 40. Where enlarged diameter portion 38 is used on introducer needle 31, preferably the diameter of opening 315 is slightly larger than the diameter of the main portion of introducer needle 31 but smaller than the diameter of enlarged diameter portion 38. Of course, it is not necessary for leaf spring 300 to include proximal wall 310 and opening 315 as long as proximal opening 43, washer 49 or tether 50 is used to prevent proximal movement of sharp distal tip 32 out of needle shield 40.

Figure 11:
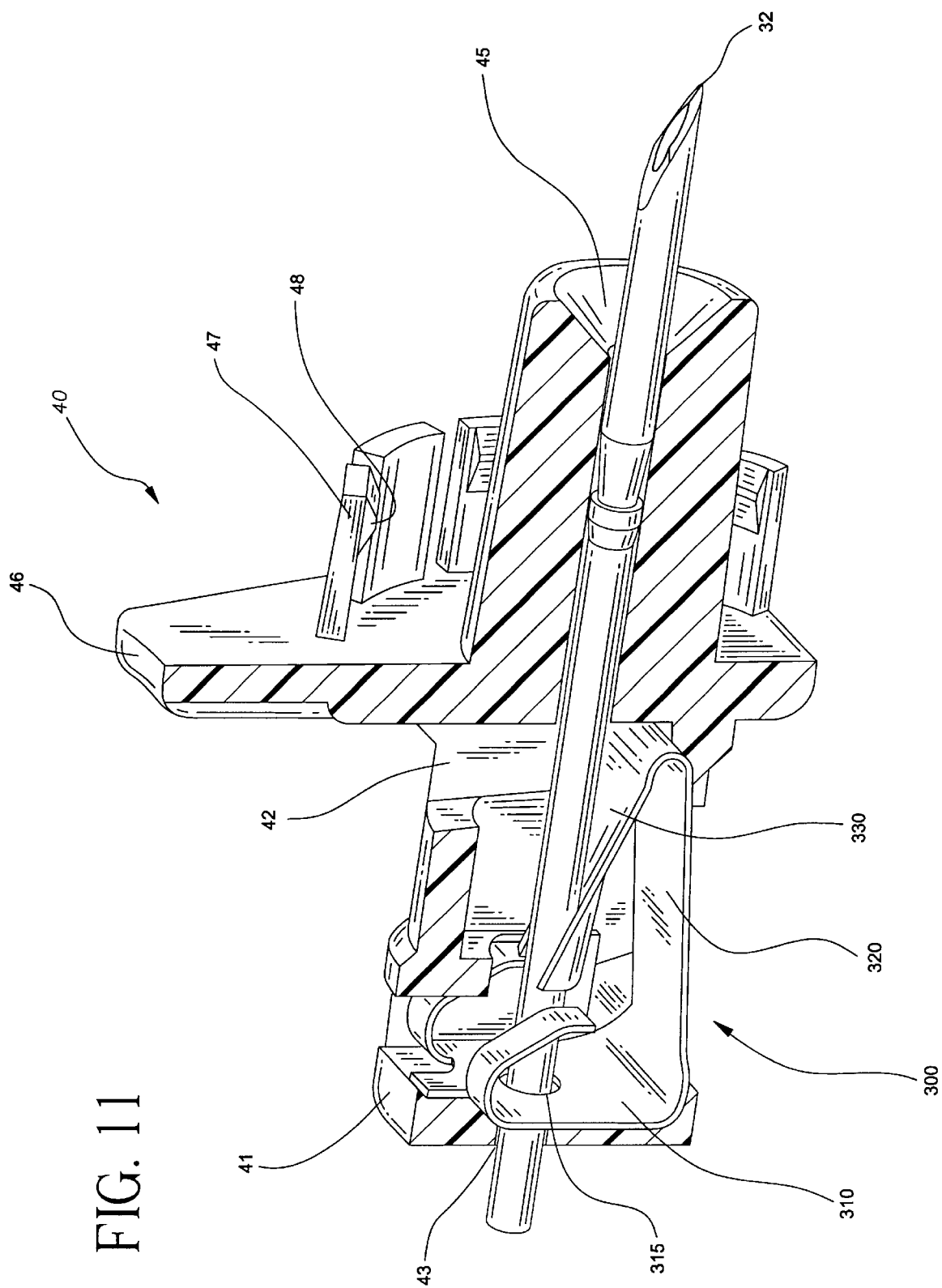
FIG. 11 is a perspective cross-sectional view of the needle shield with a third embodiment of the lock that prevents unwanted distal movement of the introducer needle and the distal portion of the introducer needle with the sharp distal tip of the introducer needle extending from the distal end of the needle shield.

Leaf spring 300 also has a support leg 320 and a locking leg 330 oriented at an angle to support leg 320 such that locking leg 330 is directed generally toward proximal wall 310 and is not perpendicular to support leg 320. Preferably, locking leg 330 approaches being parallel to support leg 320. As seen in FIG. 11, support leg 320 and locking leg 330 are preferably oriented to each other such that leaf spring 300 has a generally V-shape lying on its side, with the apex of the V facing distally. This V-shaped configuration ensures that locking leg 330 is biased toward introducer needle 31. Alternatively locking leg 330 could be oriented at a different angle to support leg 320. For example, locking leg 330 could be oriented at an angle to support leg 320 that approaches 90 degrees. See FIG. 17 and compare support leg 620 and locking leg 630. Indeed, locking leg 330 could in fact be perpendicular to support leg 320 or could be oriented anywhere between being parallel to or perpendicular to support leg 320. The main criterion for the configuration of leaf spring 300 is to have locking leg 330 biased toward introducer needle 31 so it engages enlarged diameter portion 38.

That portion of locking leg 330 that abuts introducer needle 31 can be contoured to form a generally semi-circular cross-section to approximate a portion of the circumference of the main portion of introducer needle 31. This minimizes drag on introducer needle 31 as it is being moved proximally past locking leg 330.

Figure 12:
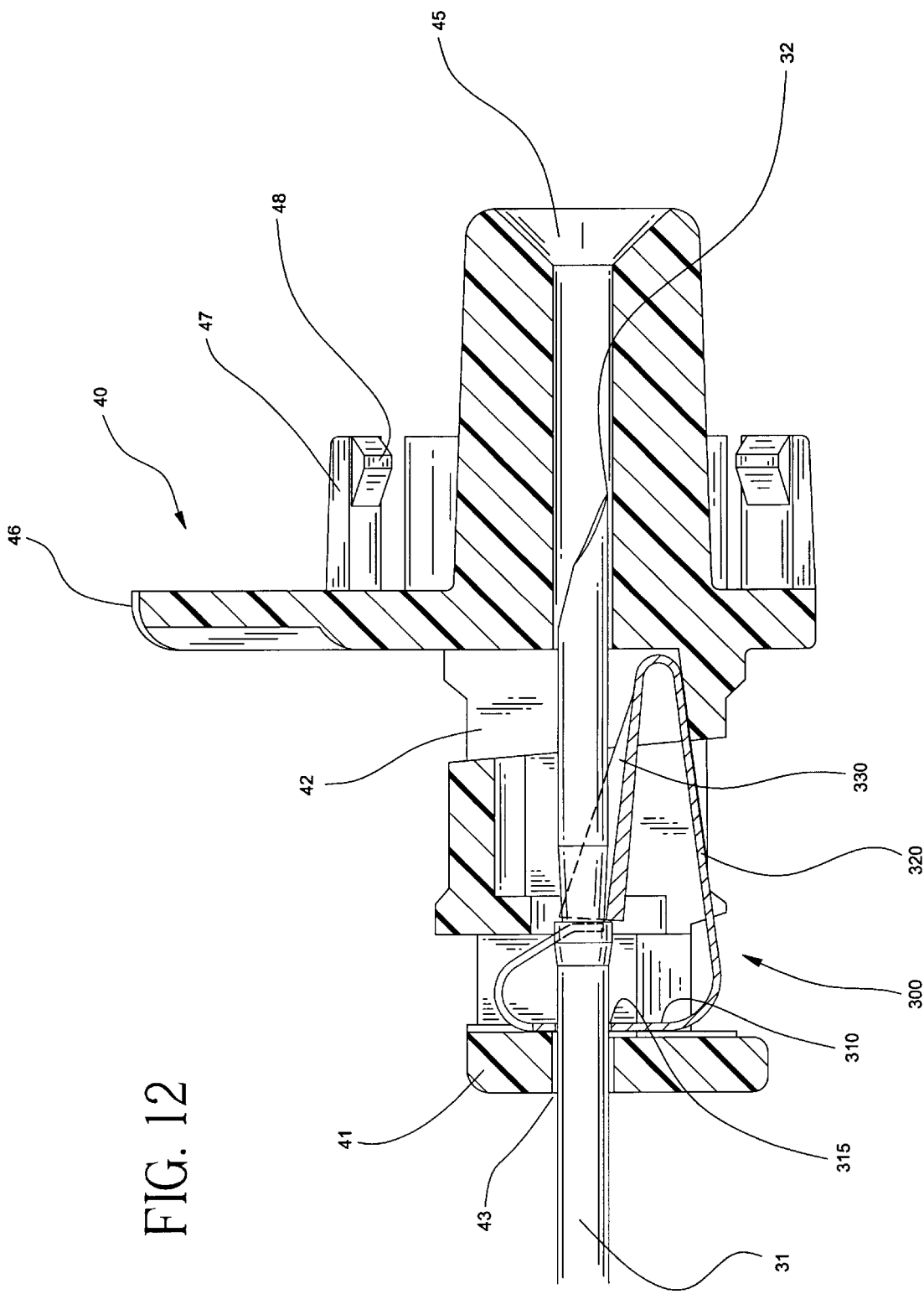
FIG. 12 is a cross-sectional view of the needle shield with the third embodiment of the lock that prevents unwanted distal movement of the introducer needle and the distal portion of the introducer needle with the sharp distal tip of the introducer needle locked in the needle shield.
Figure 13:
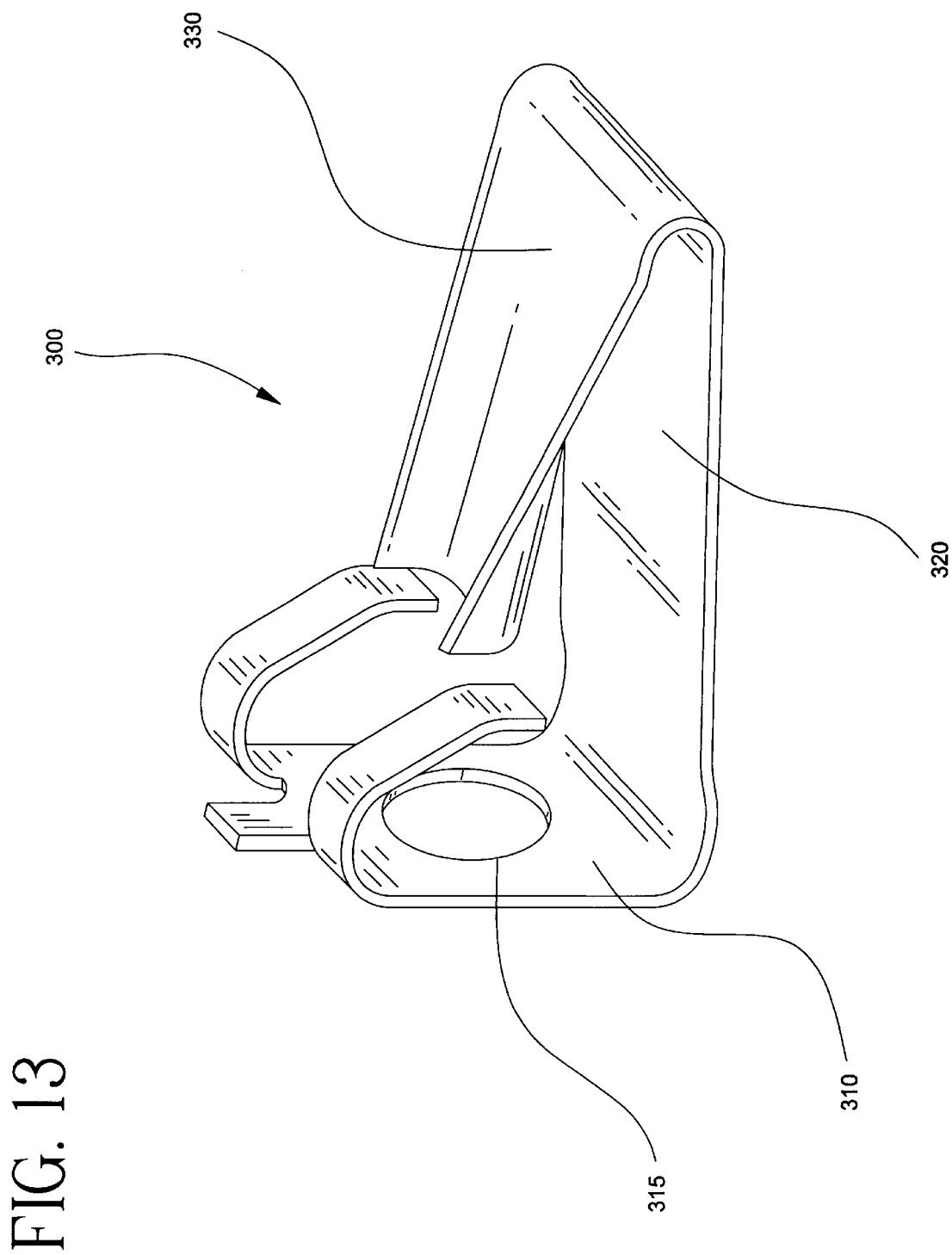
FIG. 13 is a perspective view of the leaf spring that is the third embodiment of the lock shown in FIGS. 11 and 12 that prevents unwanted distal movement of the introducer needle.

In the embodiment of FIGS. 11 through 13, enlarged diameter portion 38 shown in FIG. 3A is preferably used. This embodiment includes a tapered proximal portion 38a and a distal portion 38b that is generally perpendicular to the longitudinal axis of introducer needle 31. However, it is to be understood that the other embodiments for the discontinuous portion on introducer needle 31 could be used. In addition, the end of locking leg 330 that engages the discontinuous portion could be configured appropriately to mechanically engage the discontinuous portion. For example, if notch 39 were used as the discontinuous portion, the portion of locking leg 330 that engages notch 39 would include a tab to engage the notch. See for example, the tab in FIG. 31.

Locking leg 330 rides along the main portion of introducer needle 31 as introducer needle 31 is withdrawn proximally into needle shield 40. Locking leg 330 also rides over enlarged diameter portion 38 as it is pulled proximally past locking leg 330. Having a tapered proximal portion 38a facilitates movement of enlarged diameter portion 38 past locking leg 330 so enlarged diameter portion 38 is proximal of locking leg 330. If introducer needle 31 is moved distally after enlarged diameter portion 38 and distal portion 38b are moved proximally of the proximal end of locking leg 330, the proximal end of locking leg 330 will engage distal portion 38b and prevent further distal movement of introducer needle 31. In addition, such distally directed force applied to introducer needle 31 will cause locking leg 330 to rotate clockwise, as seen in the FIGS. This forces introducer needle 31 upwardly into tight engagement with the walls defining cavity 42 of needle shield 40 and prevents re-exposure of sharp distal tip 32.

Further proximal movement of introducer needle 31 is prevented by the engagement of enlarged diameter portion 38 with proximal wall 310. Again, if desired, a tether 50 connecting needle shield 40 to needle hub 34 could be used to prevent this unwanted proximal movement of introducer needle 31 with respect to needle shield 40.

Figure 14:
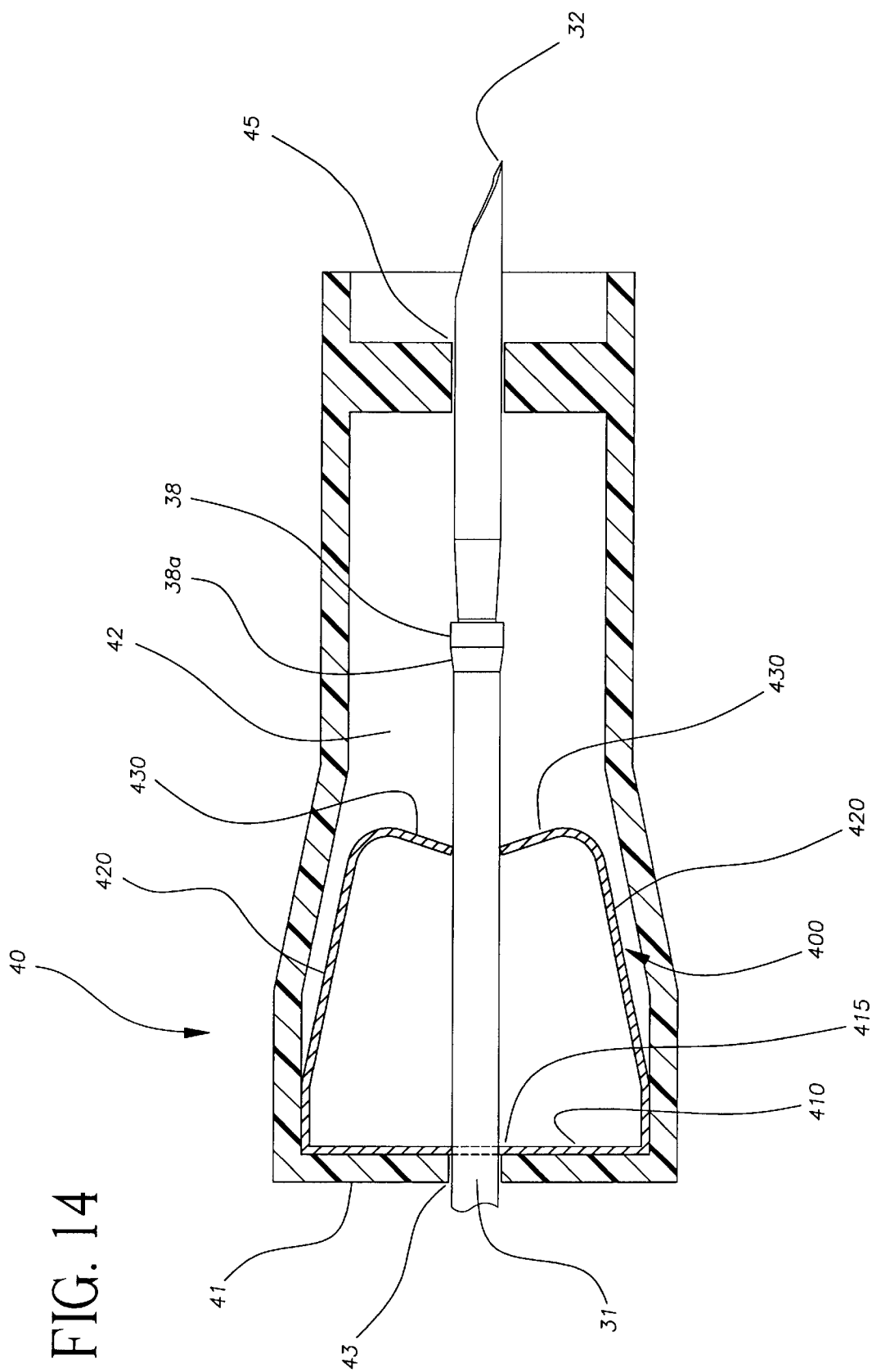
FIG. 14 is a schematic cross-sectional view of the needle shield with a fourth embodiment of the lock that prevents unwanted distal movement of the introducer needle and the distal portion of the introducer needle with the sharp distal tip of the introducer needle extending from the distal end of the needle shield.
Figure 15:
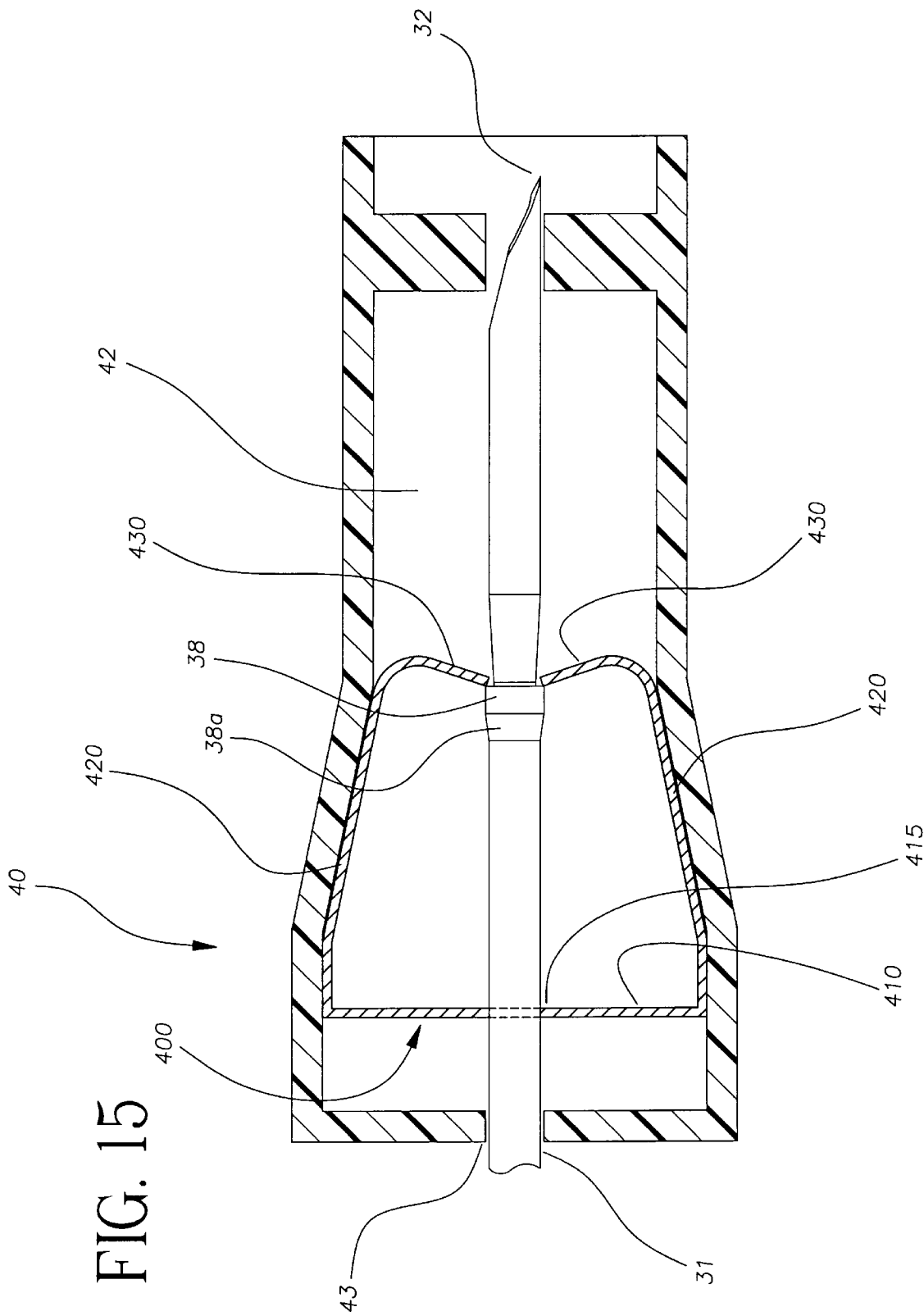
FIG. 15 is a schematic cross-sectional view of the needle shield with the fourth embodiment of the lock that prevents unwanted distal movement of the introducer needle and the distal portion of the introducer needle with the sharp distal tip of the introducer needle locked in the needle shield.

A fourth embodiment for the lock that prevents unwanted distal movement of introducer needle 31 is shown in FIGS. 14 and 15. The fourth embodiment is a leaf spring 400 that includes a proximal wall 410 supporting a pair of support legs 420 each of which is connected to a locking leg 430. Proximal wall 410 defines an opening 415 therein through which introducer needle 31 can extend. Proximal wall 410, support legs 420 and locking legs 430 are configured so that locking legs are biased toward the main portion of introducer needle 31. In this embodiment, introducer needle 31 preferably includes enlarged diameter portion 38 shown in FIG. 3A. Although as previously discussed, other embodiments for the discontinuous portion could also be used.

Locking legs 430 can be oriented at a wide range of angles to support legs 420. Preferably locking legs 430 are oriented at an angle less than 90 degrees to support legs. Regardless of the angle of orientation, locking legs 430 must engage distal portion 38b in order to prevent unwanted distal movement of introducer needle 31.

Locking legs 430 ride along the main portion of introducer needle 31 as introducer needle 31 is withdrawn proximally into needle shield 40. Locking legs 430 ride over enlarged diameter portion 38 as it is pulled proximally past locking legs 430. Tapered proximal portion 38a facilitates movement of enlarged diameter portion 38 past locking legs 430 so enlarged diameter portion is proximal of locking legs 430. If introducer needle 31 is moved distally after enlarged diameter portion 38 and distal portion 38b are moved proximally of the proximal end of locking legs 430, the ends of locking legs 430 will engage distal portion 38b and prevent further distal movement of introducer needle 31.

Further proximal movement of introducer needle 31 is prevented by the engagement of enlarged diameter portion 38 with proximal wall 410. Again, if desired, a tether 50 connecting needle shield 40 to needle hub 34 could be used to prevent this unwanted proximal movement of introducer needle 31 with respect to needle shield 40.

As shown in FIGS. 14 and 15, leaf spring 400 and housing 41 may be configured to enhance the mechanical engagement between locking legs 430 and enlarged diameter portion 38. This is achieved by allowing leaf spring 400 to move distally in cavity 42 after enlarged diameter portion 38 has been withdrawn into needle shield 40 proximal of locking legs 430. In this embodiment, cavity 42 has a tapered cross section. This taper is such that the inner diameter of cavity 42 decreases from its proximal portion toward its distal portion. This taper should be sufficient to engage support legs 420 and force support legs 420 toward introducer needle 31. Preferably this taper, as defined by the angle between the wall of cavity 42 and the longitudinal axis of introducer needle 31, should be less than 90 degrees minus the static slip angle created between the surface of support legs 420 and the wall of cavity 42. With this configuration, any subsequent distal movement of introducer needle 31 will cause leaf spring 400 to move distally with introducer needle 31 until support legs 420 engage the tapered walls of housing 41. As support legs 420 engage the tapered walls, locking legs 430 are forced into tighter contact with the shaft of introducer needle 31 and may even bind into the surface of introducer needle 31. This tight contact between locking legs 430 and distal portion 38b ensures that the force needed to overcome the mechanical engagement between the ends of locking legs 430 and distal portion 38b will be too high for a clinician, using catheter and introducer needle assembly 10 in a normal manner and in normal circumstances, to overcome.

Figure 16:
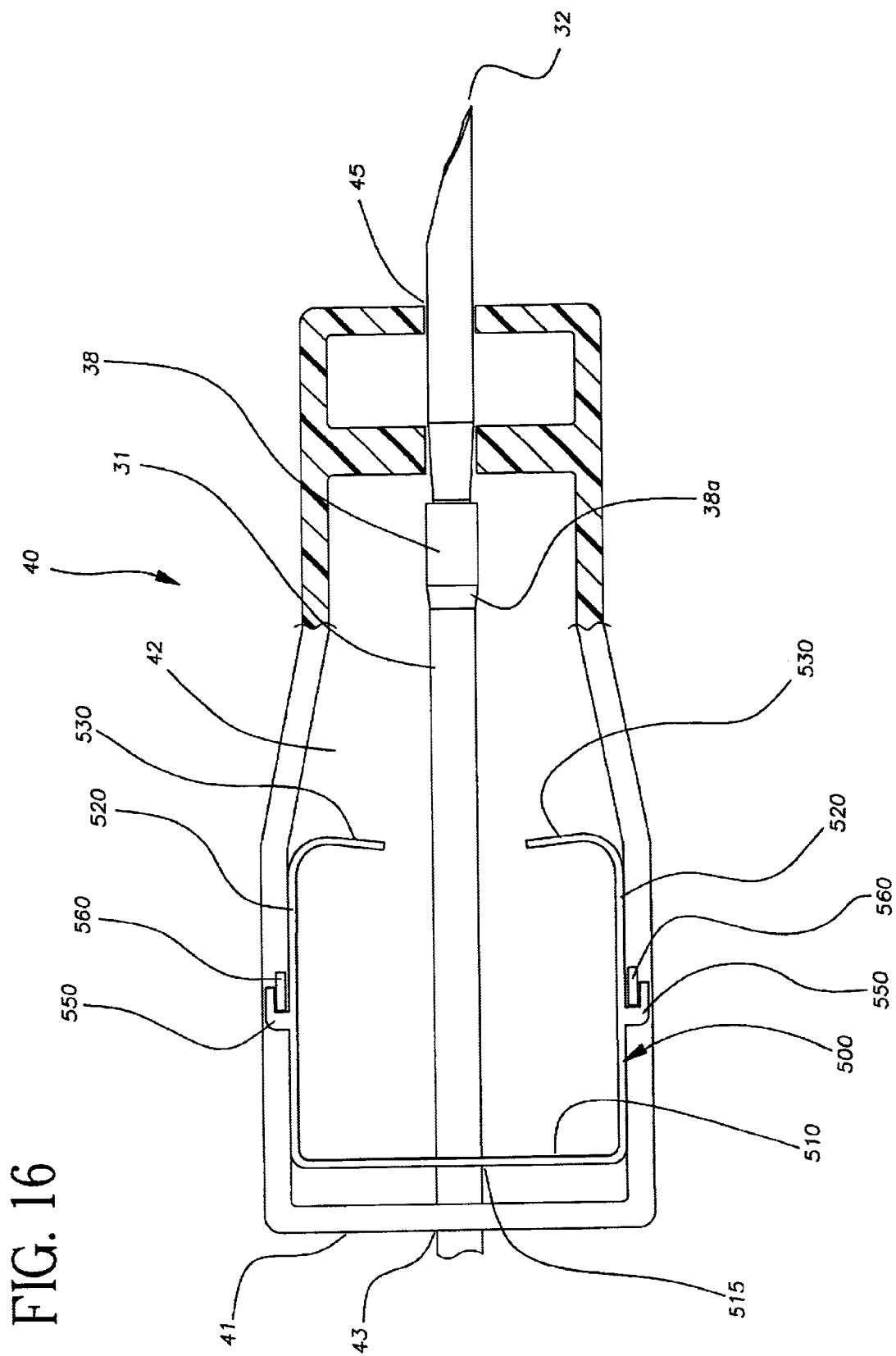
FIG. 16 is a schematic cross-sectional view of the needle shield with the fifth embodiment of the lock that prevents unwanted distal movement of the introducer needle and the distal portion of the introducer needle with the sharp distal tip of the introducer needle extending from the distal end of the needle shield.

The fifth embodiment of the lock that prevents unwanted distal movement of introducer needle 31 is a variation of the fourth embodiment of the lock that prevents unwanted distal movement of introducer needle 31 and that minimizes drag on introducer needle 31 as it is being withdrawn in needle shield 40. See FIG. 16. The fifth embodiment is a leaf spring 500 that includes a proximal wall 510 supporting a pair of support legs 520 each of which is connected to a locking leg 530. Proximal wall 510 defines an opening 515 therein through which introducer needle 31 can extend. Proximal wall 510, support legs 520 and locking legs 530 are configured so that locking legs are biased toward the shaft of introducer needle 31. In this embodiment, introducer needle 31 preferably includes enlarged diameter portion 38 shown in FIG. 3A. Although as previously discussed, other embodiments for the discontinuous portion could also be used.

At least one, but preferably each support leg 520 includes a support finger 550 thereon. Each support finger 550 cooperates with a support tab 560 formed on housing 41 to hold each support leg 520 away from the shaft of introducer needle 31. Leaf spring 500 is disposed in cavity 42 such that proximal wall 510 is spaced distally from the proximal wall of cavity 42 to allow proximal movement of leaf spring 500 when introducer needle 31 is withdrawn into needle shield 40. When enlarged diameter portion 38 engages proximal wall 510 as a result of the proximal movement of introducer needle 31, leaf spring 500 will be moved proximally with continued proximal movement of introducer needle 31. This allows each support finger 550 to be moved out of engagement with support tabs 560, which in turn allows support legs 520 to return to their inward position. In the inward position, locking legs 530 engage the main portion of introducer needle 31. Unwanted distal and proximal movement of introducer needle 31 is prevented in a similar manner as is accomplished in the fourth embodiment of the lock.

Figure 17:
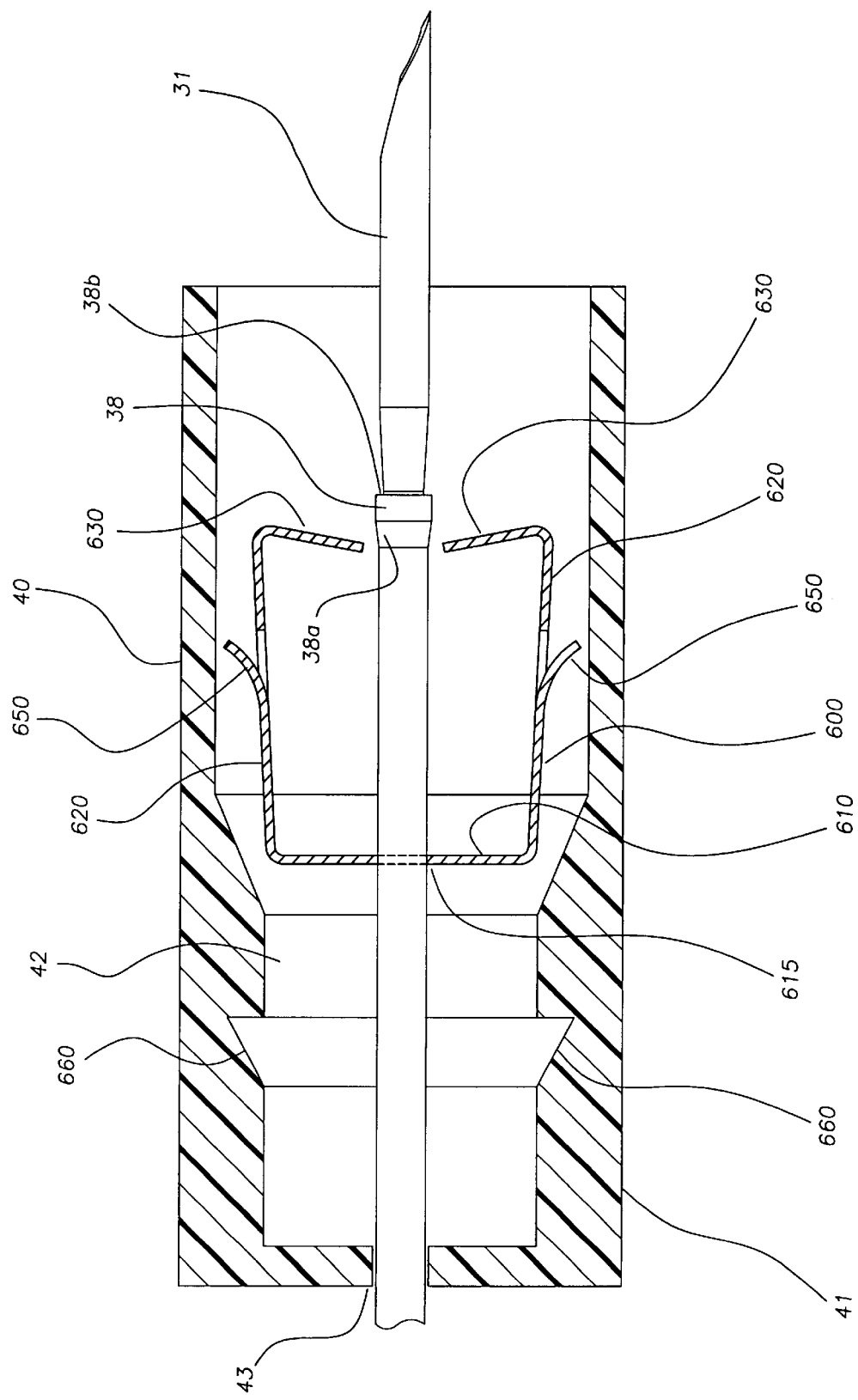
FIG. 17 is a schematic cross-sectional view of the needle shield with a sixth embodiment of the lock that prevents unwanted distal movement of the introducer needle and the distal portion of the introducer needle with the sharp distal tip of the introducer needle extending from the distal end of in the needle shield.
Figure 18:
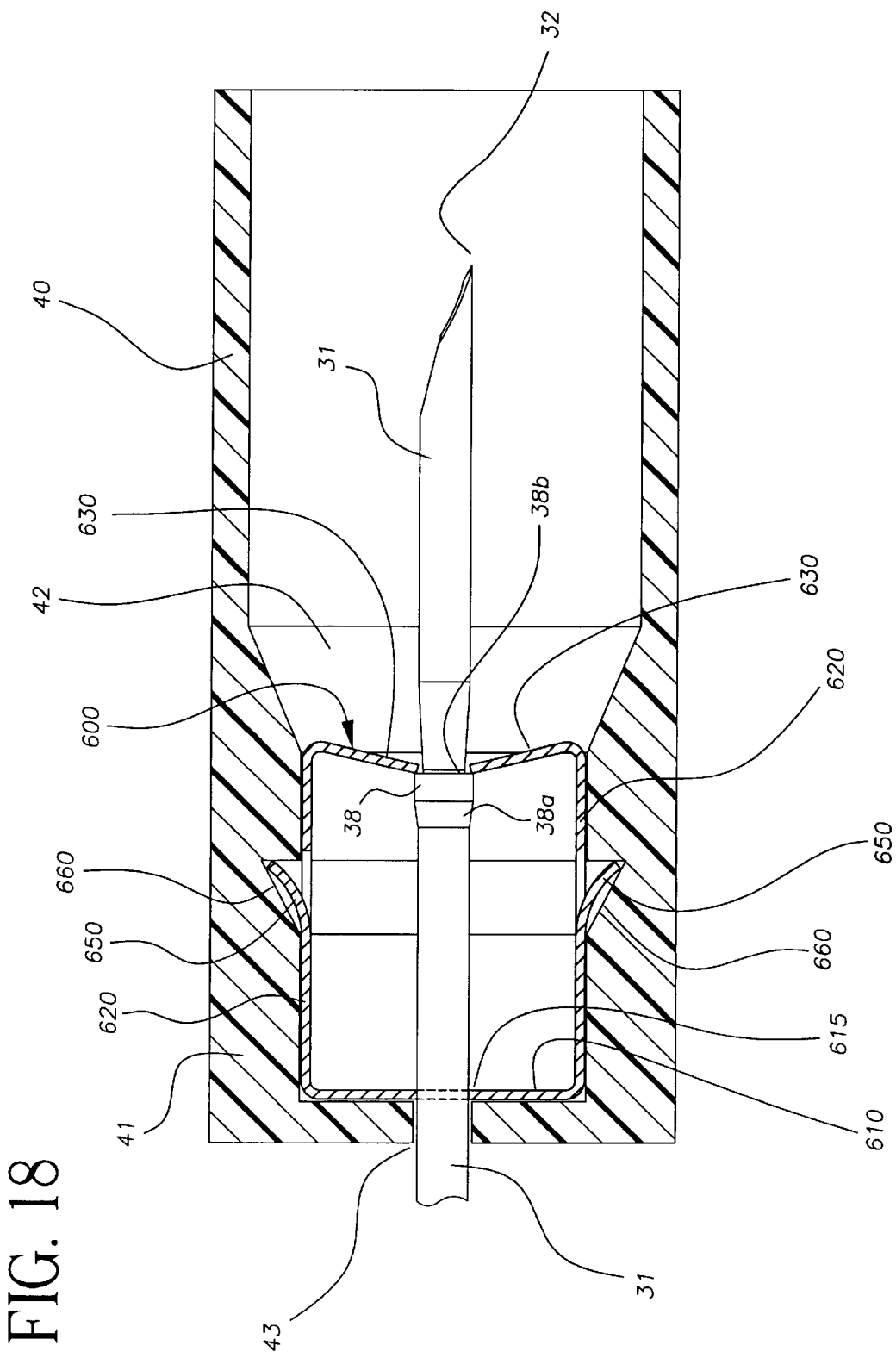
FIG. 18 is a schematic cross-sectional view of the needle shield with the sixth embodiment of the lock that prevents unwanted distal movement of the introducer needle and the distal portion of the introducer needle with the sharp distal tip of the introducer needle locked in the needle shield.

The sixth embodiment of the lock that prevents unwanted distal movement of introducer needle 31 is shown in FIGS. 17 and 18. In this embodiment, the leaf spring 600 includes a proximal wall 610 supporting a pair of support legs 620 each of which is connected to a locking leg 630. Proximal wall 610 defines an opening 615 therein through which introducer needle 31 can extend. In this embodiment, it is not necessary that locking legs 630 be biased toward the shaft of introducer needle 31. In fact, in order to minimize drag on the shaft of introducer needle 31 as it is moved proximally into needle shield 40, the ends of locking legs 630 are preferably spaced away from the shaft of introducer needle 31. This allows introducer needle 31 to be easily withdrawn into needle shield 40.

In this embodiment, introducer needle 31 preferably includes enlarged diameter portion 38 shown in FIG. 3A. Although as previously discussed, other embodiments for the discontinuous portion could also be used.

Cavity 42 has a proximal portion and a distal portion where the diameter of the proximal portion is smaller than the diameter of the distal portion. When sharp distal tip 32 is distal of the distal end of needle shield 40 prior to use in inserting a catheter into a patient, leaf spring 600 is located substantially in the distal portion of cavity 42. As introducer needle 31 continues to be moved proximally into needle shield 40, enlarged diameter portion 38 moves proximally of locking legs 630 and subsequently engages proximal wall 610 and subsequently pulls leaf spring 600 into the proximal portion of cavity 42. The smaller diameter for the proximal portion forces support legs 620 and thus locking legs 630 toward the main portion of introducer needle 31 so that locking legs 630 can engage introducer needle 31 distal of but adjacent to enlarged diameter portion 38.

The leaf spring 600 includes at least one, and preferably two, flexible radially outwardly biased fingers 650 extending from support legs 620. Housing 41 defines a slot 660 for each finger 650 wherein each slot 660 has a proximally facing shoulder. As leaf spring 600 is pulled proximally into the proximal portion of cavity 42 by the engagement between enlarged diameter portion 38 and proximal wall 610, fingers 650 flex inwardly because of their contact with the inner walls of housing 41. However, once fingers 650 become aligned with slots 660, fingers 650 can return to their outward position and move into slots 660. The engagement of fingers 650 and the proximally facing shoulder of slot 660 prevents any subsequent distal movement of leaf spring 600 with respect to housing 41. When leaf spring 600 is in this position in housing 41, the ends of locking legs 630 abut introducer needle 31 distal of but adjacent to enlarged diameter portion 38. Thus, any unwanted distal movement of introducer needle 31 is prevented by the engagement of the ends of locking legs 630 and distal portion 38b.

Figure 19:
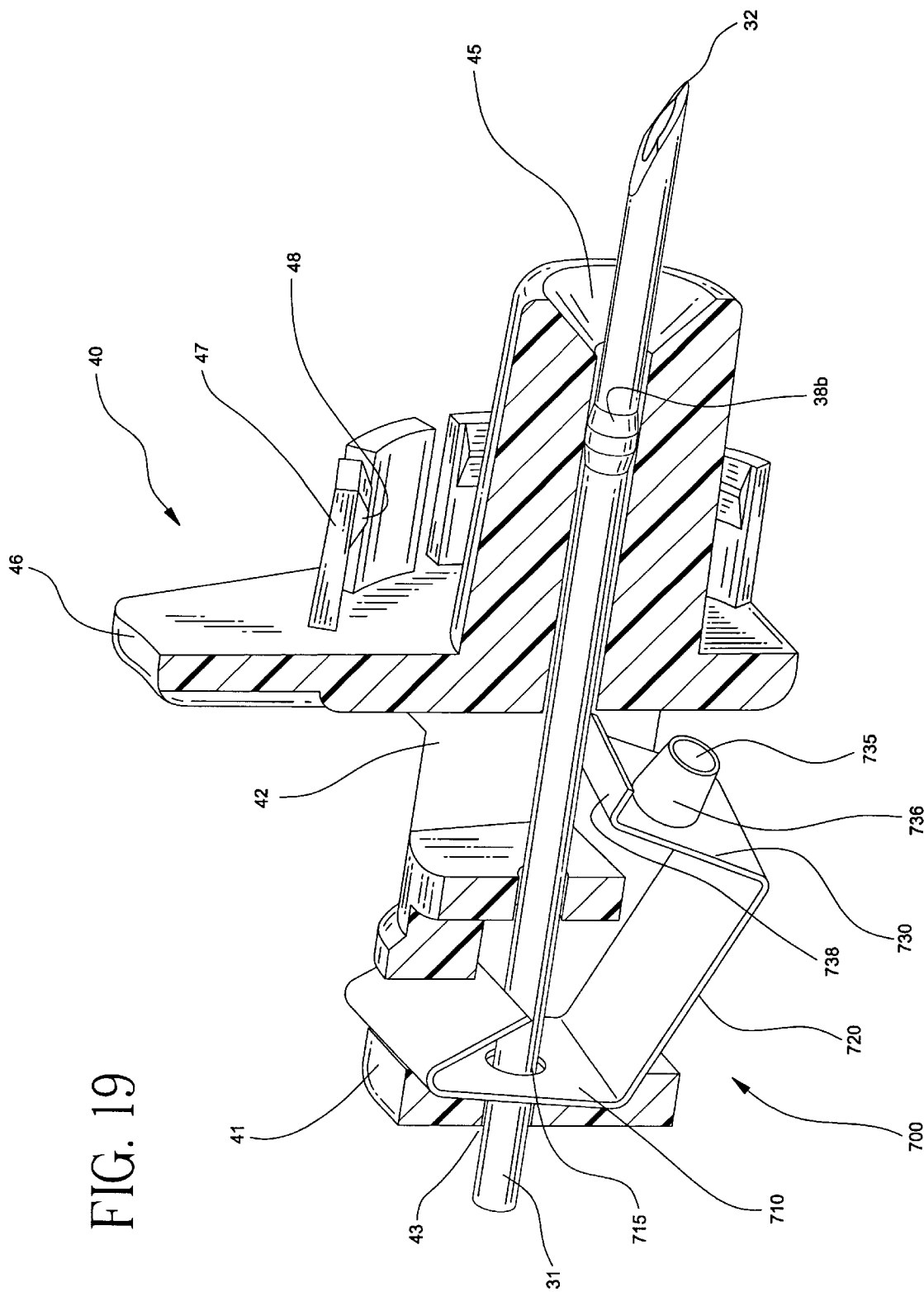
FIG. 19 is a perspective cross-sectional view of the needle shield with a seventh embodiment of the lock that prevents unwanted distal movement of the introducer needle and the distal portion of the introducer needle with the sharp distal tip of the introducer needle extending from the distal end of in the needle shield.
Figure 20:
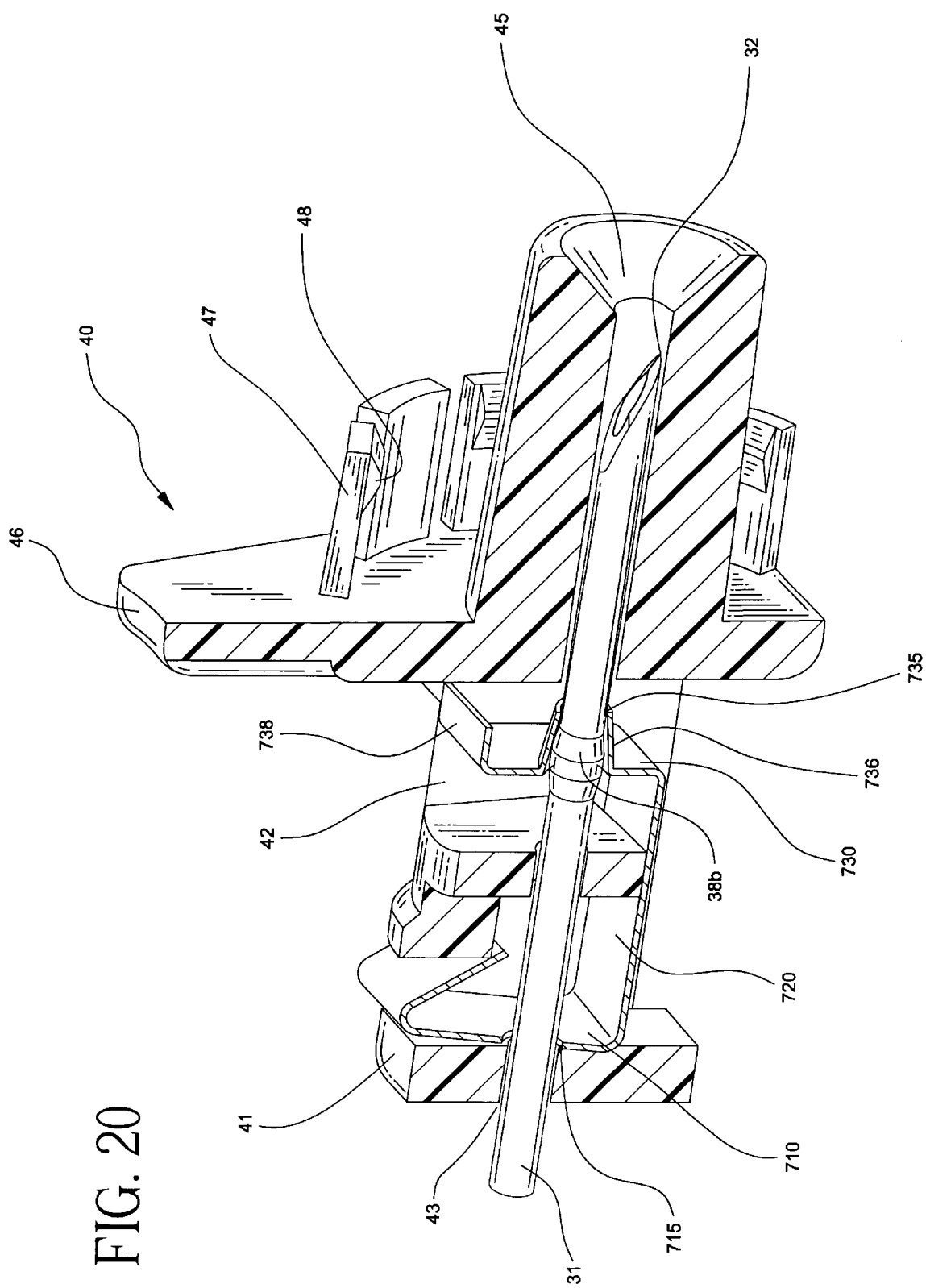
FIG. 20 is a perspective cross-sectional view of the needle shield with the seventh embodiment of the lock that prevents unwanted distal movement of the introducer needle and the distal portion of the introducer needle with the sharp distal tip of the introducer needle locked in the needle shield.
Figure 21:
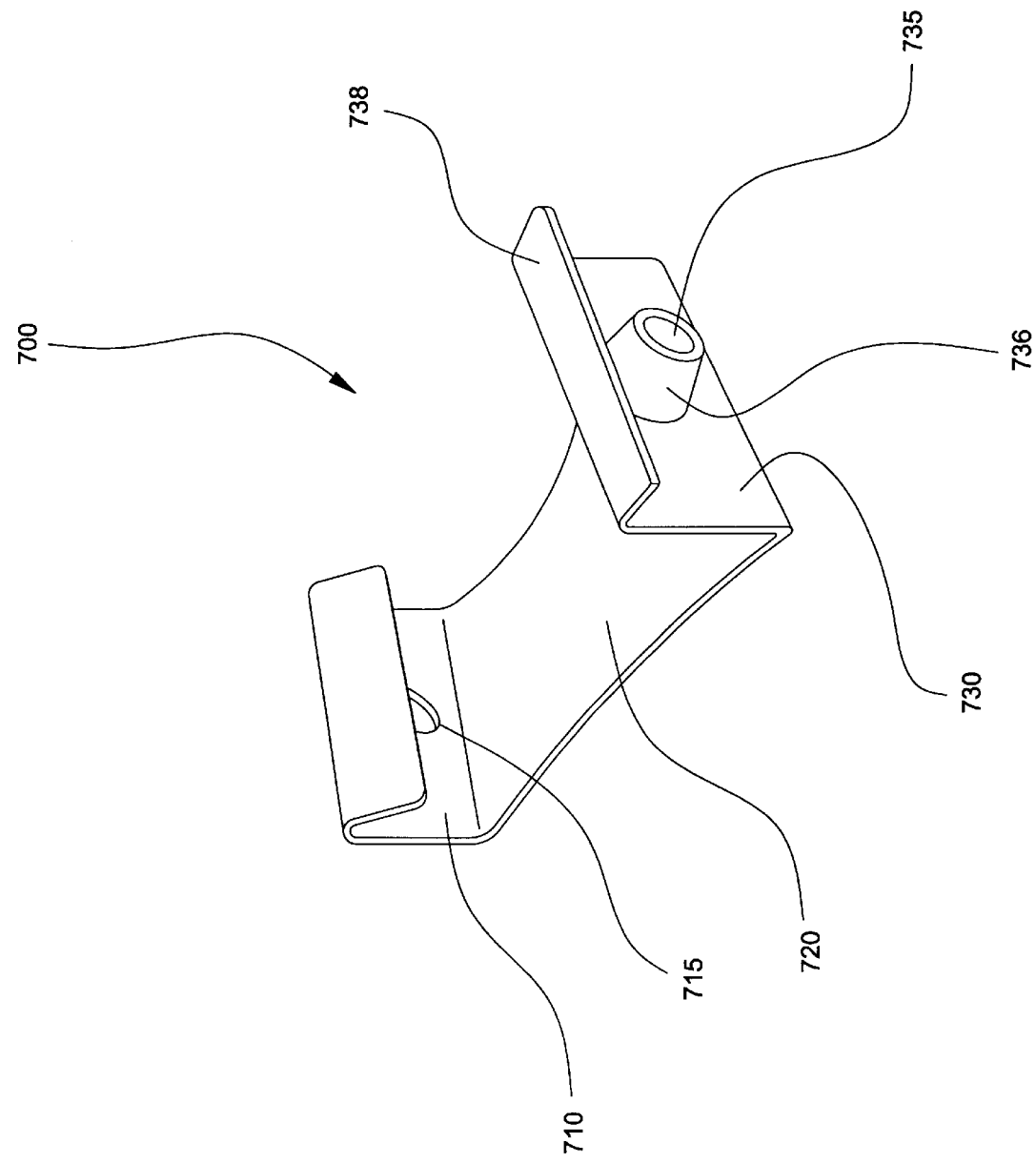
FIG. 21 is a perspective view of the leaf spring that is the seventh embodiment of the lock shown in FIGS. 19 and 20 that prevents unwanted distal movement of the introducer needle.

A seventh embodiment for the lock that prevents unwanted distal movement of introducer needle 31 is shown in FIGS. 19 through 21. In this embodiment, leaf spring 700 includes a proximal wall 710 supporting a support leg 720, which in turn is connected to a locking leg 730. Proximal wall 710 defines an opening 715 therein through which introducer needle 31 can extend. Preferably locking leg 730 is substantially perpendicular to support leg 720 and defines an opening 735 therein. Preferably the diameter of opening 735 is slightly larger than the diameter of the main portion of introducer needle 31 but is smaller than the diameter of enlarged diameter portion 38. Proximal wall 710, support leg 720 and locking leg 730 are configured such that locking leg 730 is biased toward introducer needle 31. Of course, the orientation of leaf spring 700 could be at any angle around the longitudinal axis of introducer needle 31 so that support leg is biased toward introducer needle 31.

In this embodiment, introducer needle 31 must include enlarged diameter portion 38. Preferably, enlarged diameter portion 38 shown in FIG. 3C is used.

In the unlocked and biased position for leaf spring 700, sharp distal tip 32 of introducer needle 31 is distal of the distal end of needle shield 40 and locking leg 730 contacts and is biased toward introducer needle 31. See FIG. 19. As introducer needle 31 is withdrawn proximally into needle shield 40 locking leg 730 rides over the surface of introducer needle 31. Locking leg 730 can include a proximally or distally directed tab 738 that contacts introducer needle 31 to minimize drag on introducer needle 31. Once sharp distal tip 32 of introducer needle 31 is moved proximal of locking leg 730, leaf spring 700 returns to its unbiased, i.e. activated, position such that opening 735 is substantially aligned with the longitudinal axis of introducer needle 31 and distal opening 45. If introducer needle 31 is thereafter moved distally with respect to needle shield 40, sharp distal tip 32 of introducer needle 31 extends through opening 735 until enlarged diameter portion 38 engages opening 735. Unwanted distal movement of introducer needle 31 is thus prevented so that sharp distal tip 32 cannot be re-exposed outside needle shield 40.

Further proximal movement of introducer needle 31 is prevented by the engagement of enlarged diameter portion 38 with proximal wall 710. Again, it is not necessary for leaf spring 700 to include proximal wall 710 and opening 715. As long as proximal opening 43, washer 49 or tether 50 could be used instead to prevent this unwanted proximal movement of introducer needle 31 with respect to needle shield 40.

Locking leg 730 can have a funnel configuration 736 adjacent to opening 735. This funnel configuration 736 acts as a guide for introducer needle 31 to ensure that it passes through opening 735 if introducer needle 31 is moved distally after it has been withdrawn into needle shield 40. Funnel configuration 736 can be configured so that it is complementary to the shape of the tapered distal portion 38b of enlarged diameter portion 38 shown in FIG. 3C.

An eighth embodiment of the lock that prevents unwanted distal movement of introducer needle 31 is shown in FIGS. 22 through 25. In this embodiment, introducer needle 31 must include enlarged diameter portion 38. Preferably, enlarged diameter portion 38 shown in FIG. 3C is used.

The lock of this embodiment is a leaf spring 800 that includes a proximal wall 810, a support leg 820 connected to one end of proximal wall 810 and a locking leg 830 connected to support leg 820. In addition, leaf spring 800 includes an outwardly biased locking arm 850 connected to the other end of proximal wall 810. An opening 815 is defined in proximal wall 810 and an opening 835 is defined in locking leg 830. Both openings 815 and 835 allow introducer needle 31 to extend therethrough. Opening 835 has a diameter slightly larger than the diameter of enlarged diameter portion 38, whereas opening 815 has a diameter smaller than the largest diameter of enlarged diameter portion 38.

Cavity 42 of housing 41 defines a proximal portion, a medial portion and a distal portion wherein the diameter of the medial portion is less than the diameters of the proximal portion and the distal portion. As a result of this configuration, cavity 42 defines a proximally facing shoulder 860 and a distally facing shoulder 870. Leaf spring 800 is initially located in the medial portion of cavity 42 such that locking leg 830 abuts distally facing shoulder 870. In addition, leaf spring 800 is located in the medial portion of cavity 42 such that it is movable proximally with respect to housing 41.

Figure 22:
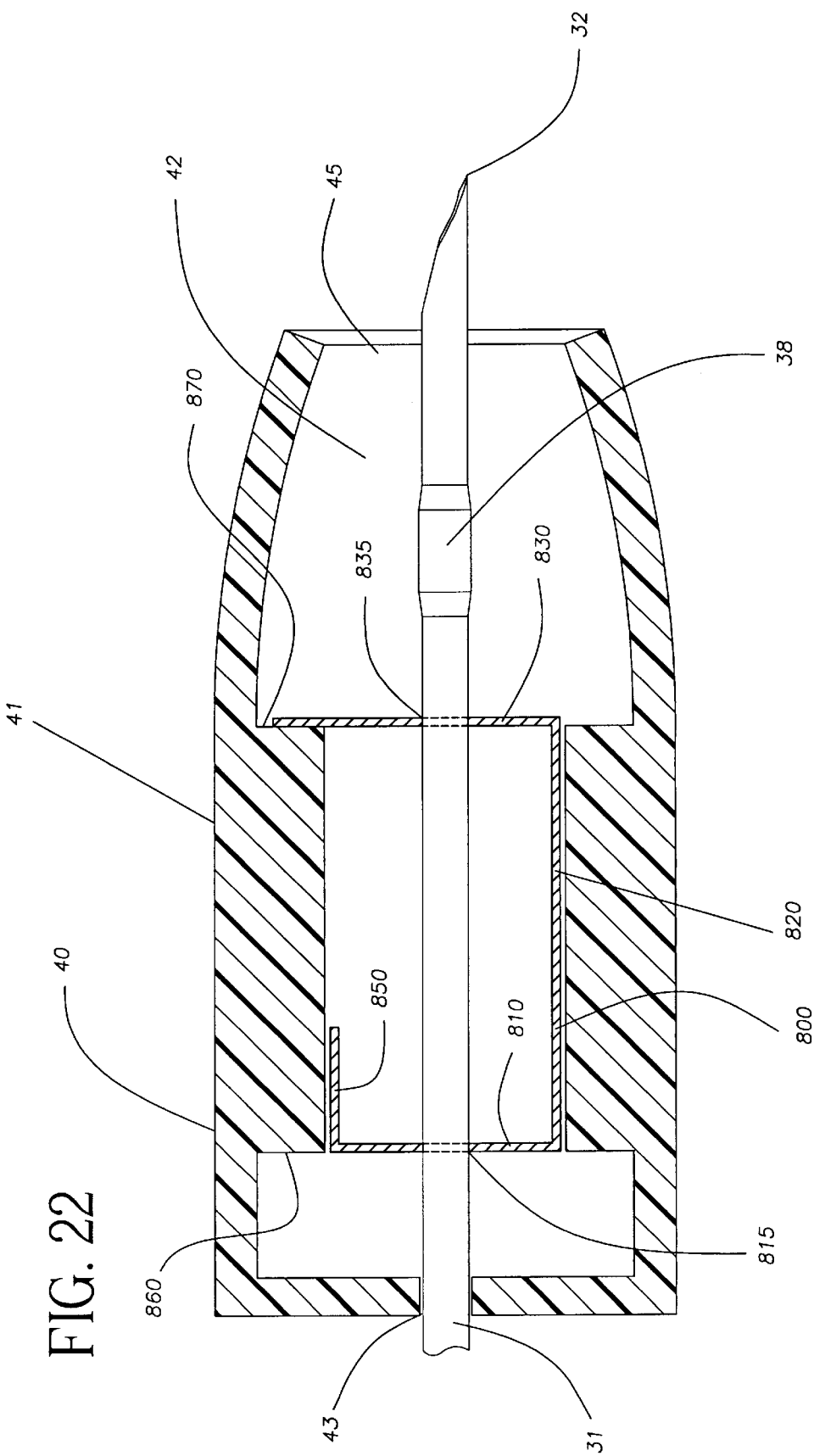
FIG. 22 is a schematic cross-sectional view of the needle shield with an eighth embodiment of the lock that prevents unwanted distal movement of the introducer needle and the distal portion of the introducer needle with the sharp distal tip of the introducer needle extending from the distal end of in the needle shield.
Figure 23:
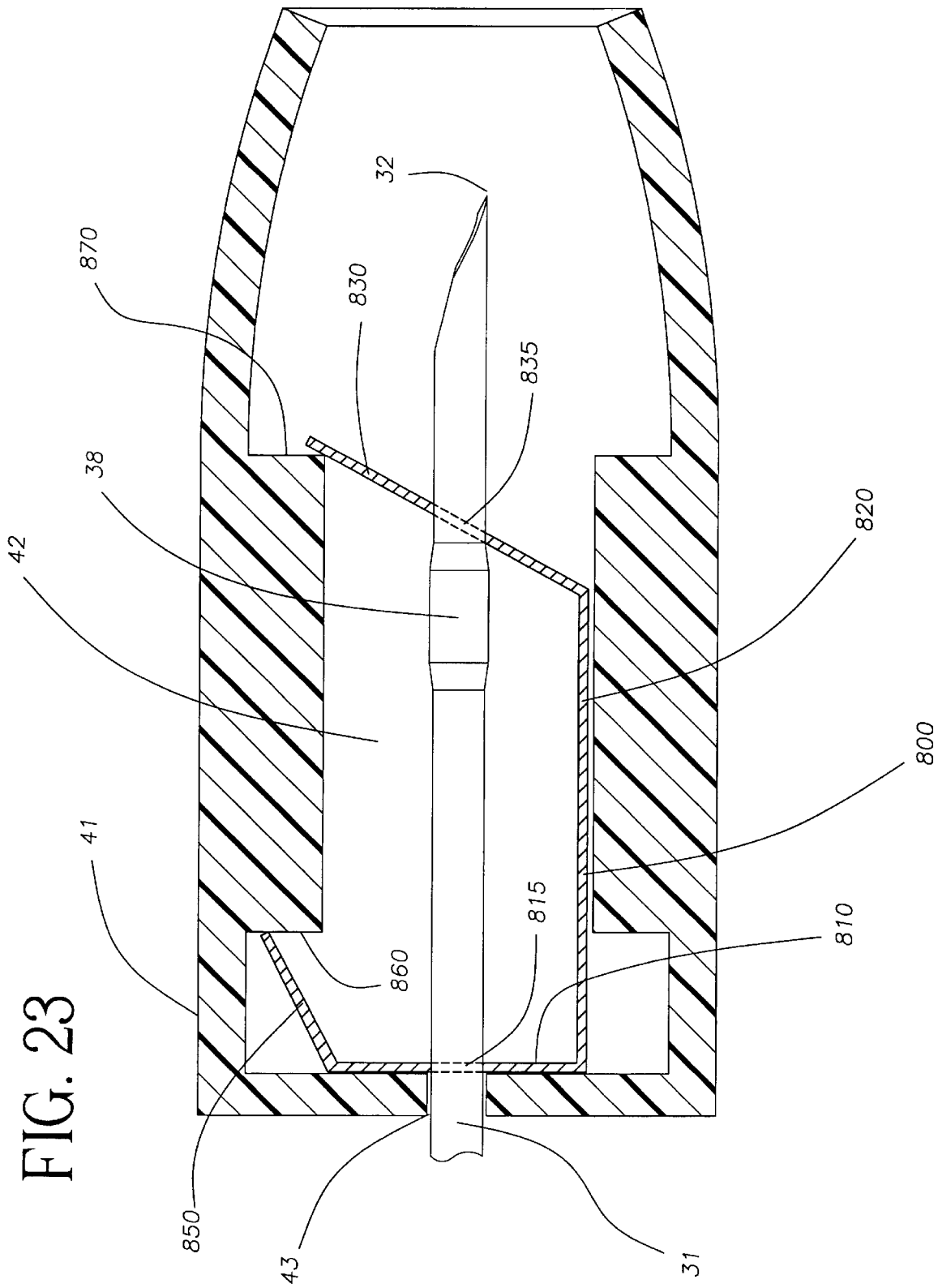
FIG. 23 is a schematic cross-sectional view of the needle shield with the eighth embodiment of the lock that prevents unwanted distal movement of the introducer needle and the distal portion of the introducer needle with the sharp distal tip of the introducer needle locked in the needle shield.
Figure 25:
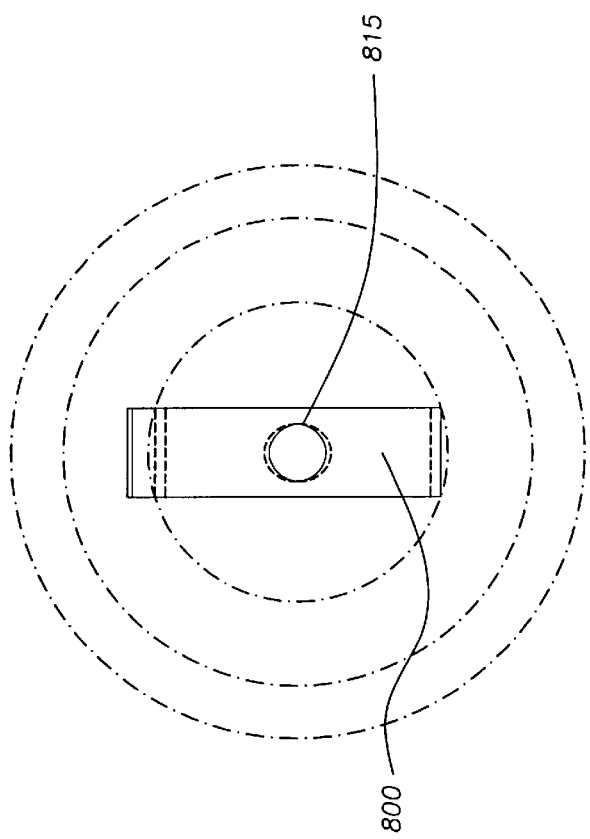
FIG. 25 is a distal end view of the leaf spring that is the eighth embodiment of the lock that prevents unwanted distal movement of the introducer needle having the orientation shown in FIG. 23.
Figure 24:
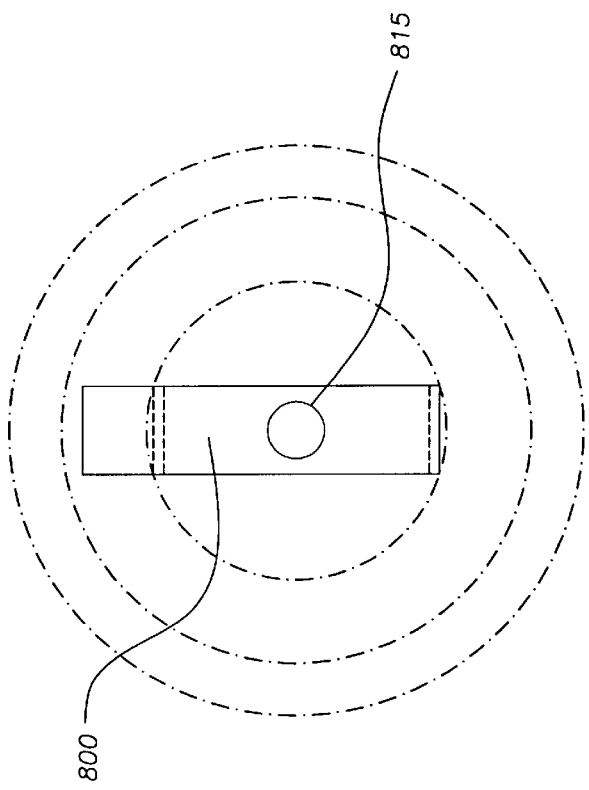
FIG. 24 is a distal end view of the leaf spring that is the eighth embodiment of the lock that prevents unwanted distal movement of the introducer needle having the orientation shown in FIG. 22.

Prior to withdrawal of sharp distal tip 32 into needle shield 40; leaf spring 800 is in the position shown in FIG. 22 such that locking leg 830 is generally perpendicular to the shaft of introducer needle 31. As introducer needle 31 is moved proximally into needle shield 40, enlarged diameter portion 38 passes through opening 835 of locking leg 830 until the proximal end of enlarged diameter portion 38 engages proximal wall 810. Since the diameter of opening 815 is less than the largest diameter of enlarged diameter portion 38, continued relative proximal movement of introducer needle 31 with respect to leaf spring 800 is prevented. However, continued proximal movement of introducer needle 31 causes leaf spring 800 to move proximally until proximal wall 810 abuts against the proximal wall of cavity 42. At this point, further proximal movement of introducer needle 31 and leaf spring 800 is prevented.

Since locking leg 830 abuts distally facing shoulder 870 in housing 41, the proximal movement of leaf spring 800 with respect to housing 41 causes locking leg 830 to rotate. As such the orientation of locking leg 830 with respect to introducer needle 31 changes so locking leg 830 is no longer perpendicular to introducer needle 31. Compare FIGS. 22 and 23. In addition, the proximal movement of leaf spring 800 causes locking arm 850 to become aligned with the larger diameter proximal portion of cavity 42. This allows locking arm 850 to move to its outward position, away from introducer needle 31 into the proximal portion of cavity 42 so that locking arm 850 abuts proximally facing shoulder 860. In this position, any subsequent distal movement of leaf spring 800 with respect to housing 41 is prevented.

When locking leg 830 is no longer perpendicular to introducer needle 31, opening 835 is skewed with respect to enlarged diameter portion 38. Thus, in this orientation, the effective diameter of opening 835 is less than the diameter of enlarged diameter portion 38 and is approximately equal to the diameter of the main portion of introducer needle 31. As used herein, the term "effective diameter" means the diameter of the image of opening 835 when it is projected onto a plane perpendicular to the longitudinal axis of introducer needle 31. Because, the effective diameter of opening 835 is less than the diameter of enlarged diameter portion 38 in the orientation shown in FIGS. 23 and 25, enlarged diameter portion 38 is prevented from moving distally past locking leg 830 and sharp distal tip 32 is effectively locked in needle shield 40. Indeed, as introducer needle 31 is moved distally, the binding force between locking leg 830 and introducer needle 31 increases making it extremely difficult for enlarged diameter portion 38 to be moved distally past locking leg 830 and thus defeat this lock.

Figure 26:
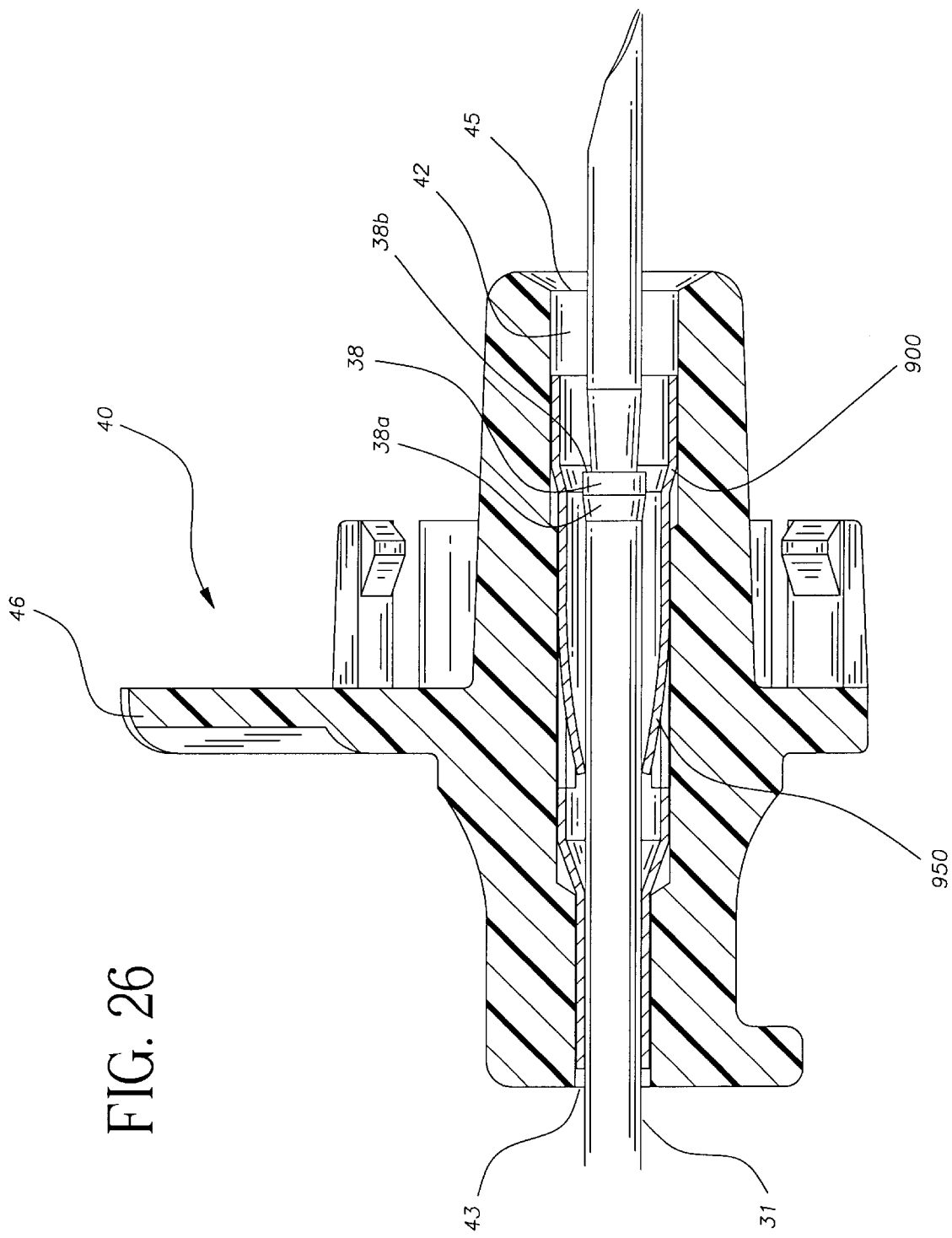
FIG. 26 is a cross-sectional view of the needle shield with a ninth embodiment of the lock that prevents unwanted distal movement of the introducer needle and the distal portion of the introducer needle with the sharp distal tip of the introducer needle extending from the distal end of the needle shield.
Figure 27:
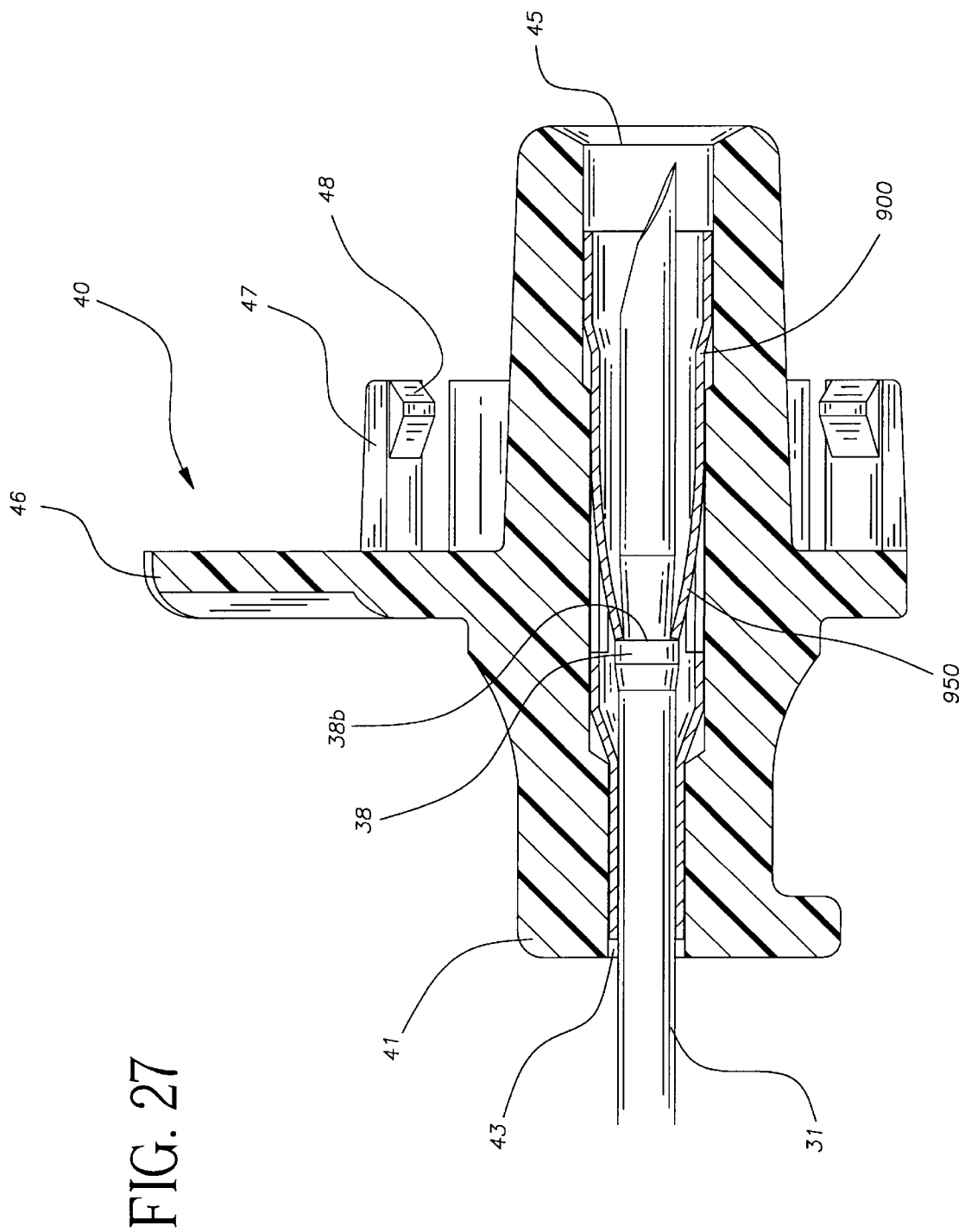
FIG. 27 is a cross-sectional view of the needle shield with the ninth embodiment of the lock that prevents unwanted distal movement of the introducer needle and the distal portion of the introducer needle with the sharp distal tip of the introducer needle locked in the needle shield.
Figure 28:
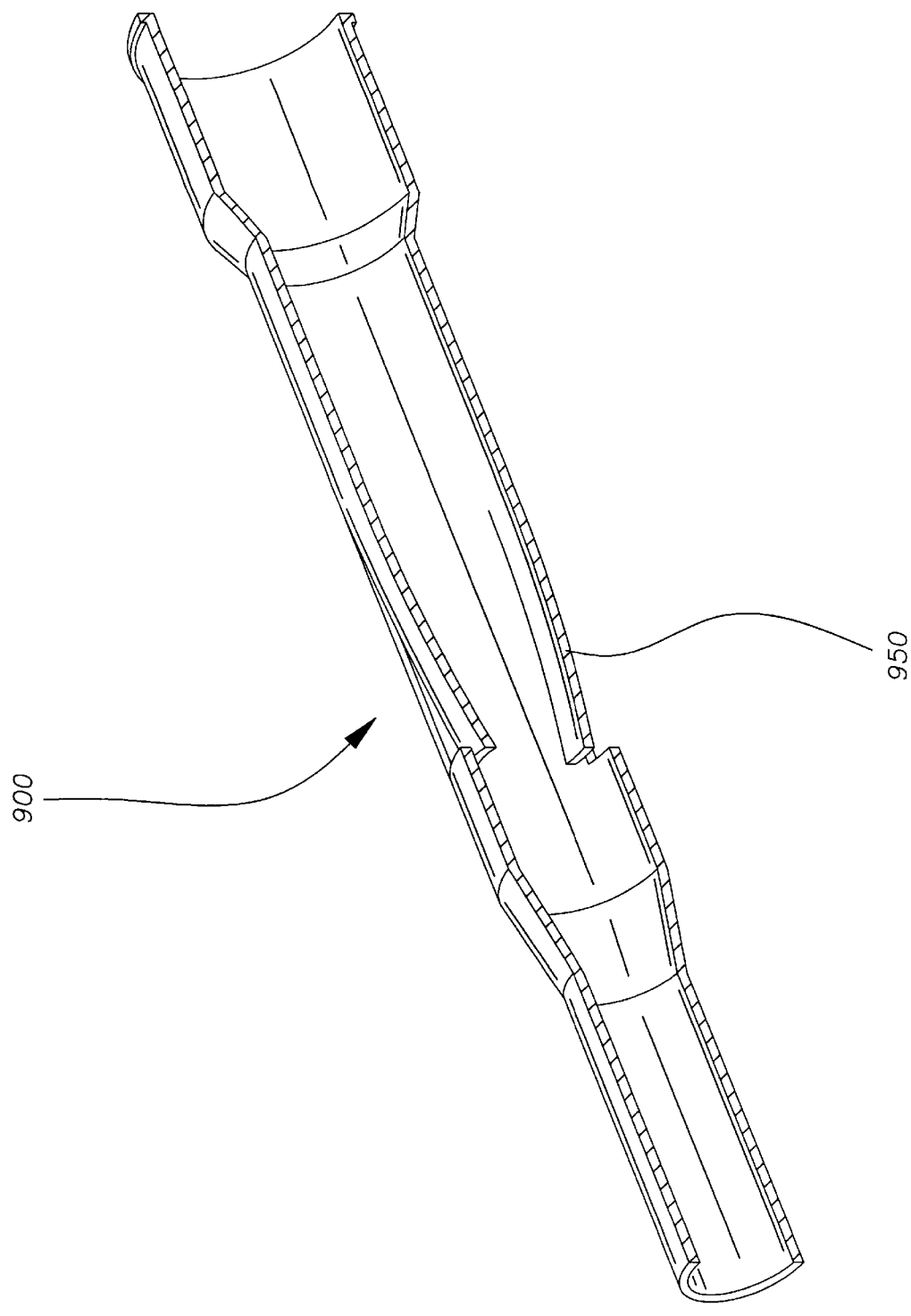
FIG. 28 is a perspective cross-sectional view of the tube that is the ninth embodiment of the lock shown in FIGS. 26 and 27 to prevent unwanted distal movement of the introducer needle.
Figure 29:
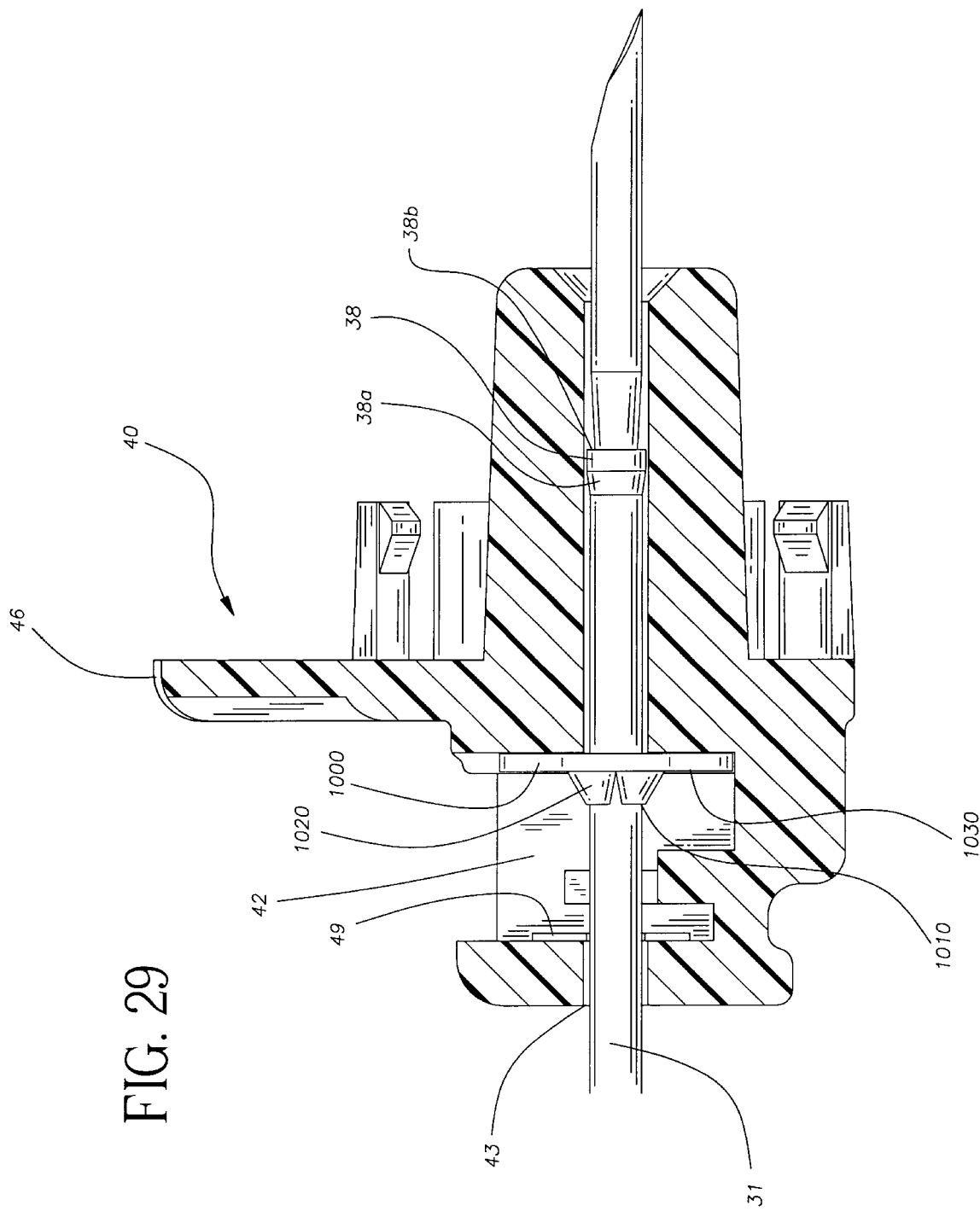
FIG. 29 is a cross-sectional view of the needle shield with a tenth embodiment of the lock that prevents unwanted distal movement of the introducer needle and the distal portion of the introducer needle with the sharp distal tip of the introducer needle extending from the distal end of in the needle shield.
Figure 30:
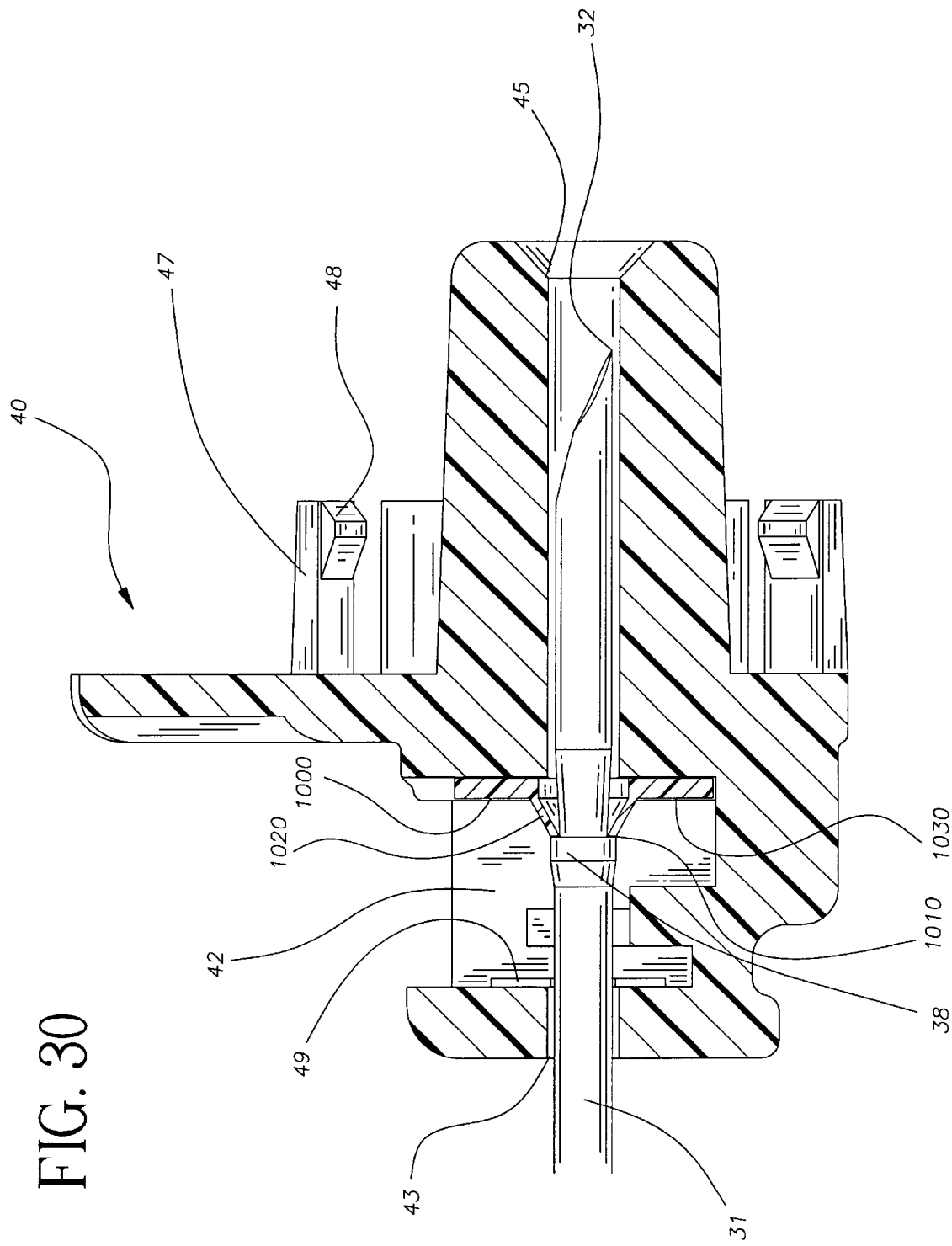
FIG. 30 is a cross-sectional view of the needle shield with the tenth embodiment of the lock that prevents unwanted distal movement of the introducer needle and the distal portion of the introducer needle with the sharp distal tip of the introducer needle locked in the needle shield.

A ninth embodiment of the lock that prevents unwanted distal movement of introducer needle 31 is shown in FIGS. 26 through 28 and is a tube 900. In this embodiment, the discontinuous portion on introducer needle 31 is preferably an enlarged diameter portion. Even more preferably, enlarged diameter portion 38 shown in FIG. 3A is used although other embodiments for enlarged diameter portion 38 could be used.

Tube 900 is located in cavity 42 and includes at least one movable lanced tab 950 that extends inwardly into tube 900 in a proximal direction. Preferably two such tabs 950 are formed on opposite sides of tube 900. The distal portion of tube 900 has an inner diameter greater than the diameter of enlarged diameter portion 38 to allow introducer needle 31 freely to move therein. Because tabs 950 are movable, enlarged diameter portion 38 can move past the proximal ends of tabs 950 as introducer needle 31 is withdrawn proximally into needle shield 40. Again the proximal movement of introducer needle 31 past tabs 950 is facilitated by tapered proximal portion 38a. Once introducer needle 31 has been withdrawn proximally into needle shield 40 such that tabs 950 are distal of distal portion 38b, any unwanted distal movement of introducer needle 31 will be prevented by the engagement of the proximal ends of tabs 950 with enlarged diameter portion 38. Further proximal movement of introducer needle 31 is prevented by the engagement of enlarged diameter portion 38 with proximal opening 43. Alternatively, the proximal portion of tube 900 could be formed with an inner diameter smaller than the diameter of enlarged diameter portion 38 to prevent unwanted proximal movement of introducer needle out of tube 900. In addition, washer 49 or tether 50 could be used to prevent unwanted proximal movement.

A tenth embodiment of the lock that prevents unwanted movement of introducer needle 31 is shown in FIGS. 29 through 32. This lock is a speed nut 1000, which defines a through hole 1010 that has a diameter slightly larger than the diameter of the main portion of introducer needle 31. This allows introducer needle 31 to extend through speed nut 1000. Speed nut 1000 includes at least one but preferably a plurality of movable tabs 1020 extending from the main body portion 1030 of speed nut 1000. Tabs 1020 are biased toward introducer needle 31 so they are proximally oriented and extend inwardly toward the proximal end of introducer needle 31. The distal ends of tabs 1020 are connected to main body portion 1030 of speed nut 1000 by, for example, a living hinge. See FIG. 32.

Because tabs 1020 are proximally oriented and movable, enlarged diameter portion 38 can move easily past the proximal ends of tabs 1020 as introducer needle 31 is withdrawn proximally into needle shield 40. Once introducer needle 31 has been withdrawn proximally into needle shield 40 such that tabs 1020 are distal of enlarged diameter portion 38, unwanted distal movement of introducer needle 31 will be prevented by the engagement of the proximal ends of tabs 1020 with distal portion 38b of enlarged diameter portion 38. The generally proximal orientation of tabs 1020 also causes tabs 1020 to bite into the surface of introducer needle 31 to hold introducer needle 31 in place. Further proximal movement of introducer needle 31 is prevented by the engagement of enlarged diameter portion 38 with proximal opening 43 or washer 49. Again, proximal opening 43, washer 49 or tether 50 could be used to prevent this unwanted proximal movement.

Figure 3D:
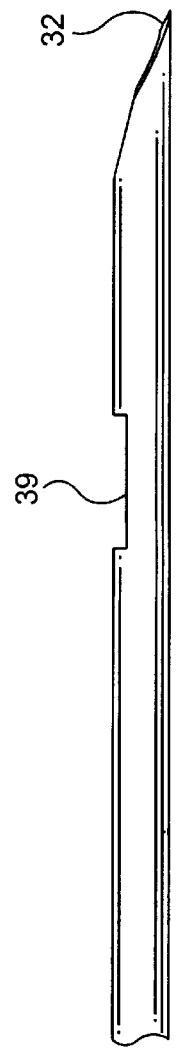
FIG. 3D is an enlarged elevation view of the distal portion the introducer needle with a fourth embodiment of the discontinuous portion thereon used in the catheter and introducer needle assembly with the needle shield of this invention.
Figure 3E:
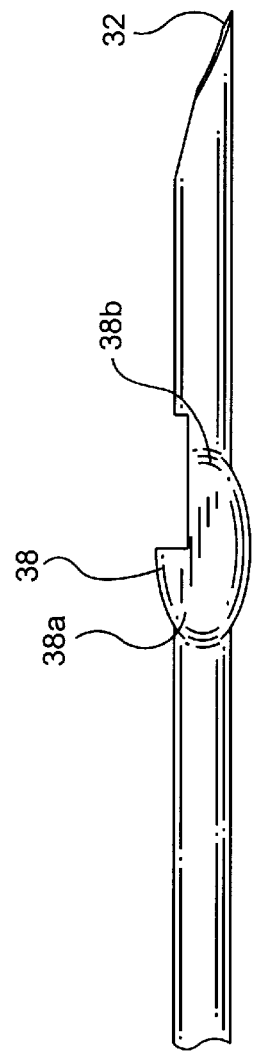
FIG. 3E is an enlarged elevation view of the distal portion of the introducer needle with a fifth embodiment of the discontinuous portion thereon used in the catheter and introducer needle assembly with the needle shield of this invention.
Figure 3F:
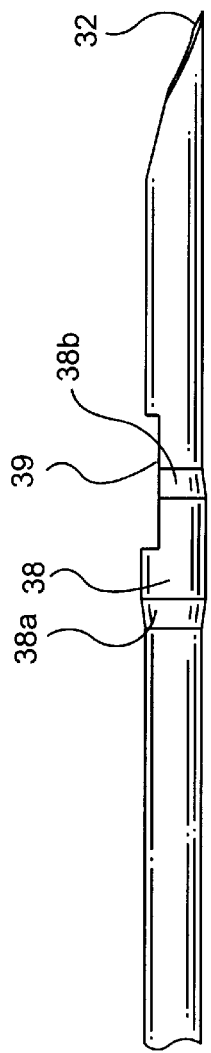
FIG. 3F is an enlarged elevation view of the distal portion of the introducer needle with a sixth embodiment of the discontinuous portion thereon used in the catheter and introducer needle assembly with the needle shield of this invention.
Figure 3G:
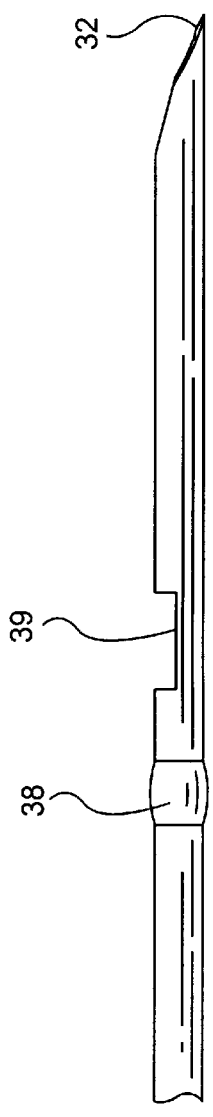
FIG. 3G is an enlarged elevation view of the distal portion of the introducer needle with a seventh embodiment of the discontinuous portion thereon used in the catheter and introducer needle assembly with the needle shield of this invention.
Figure 31:
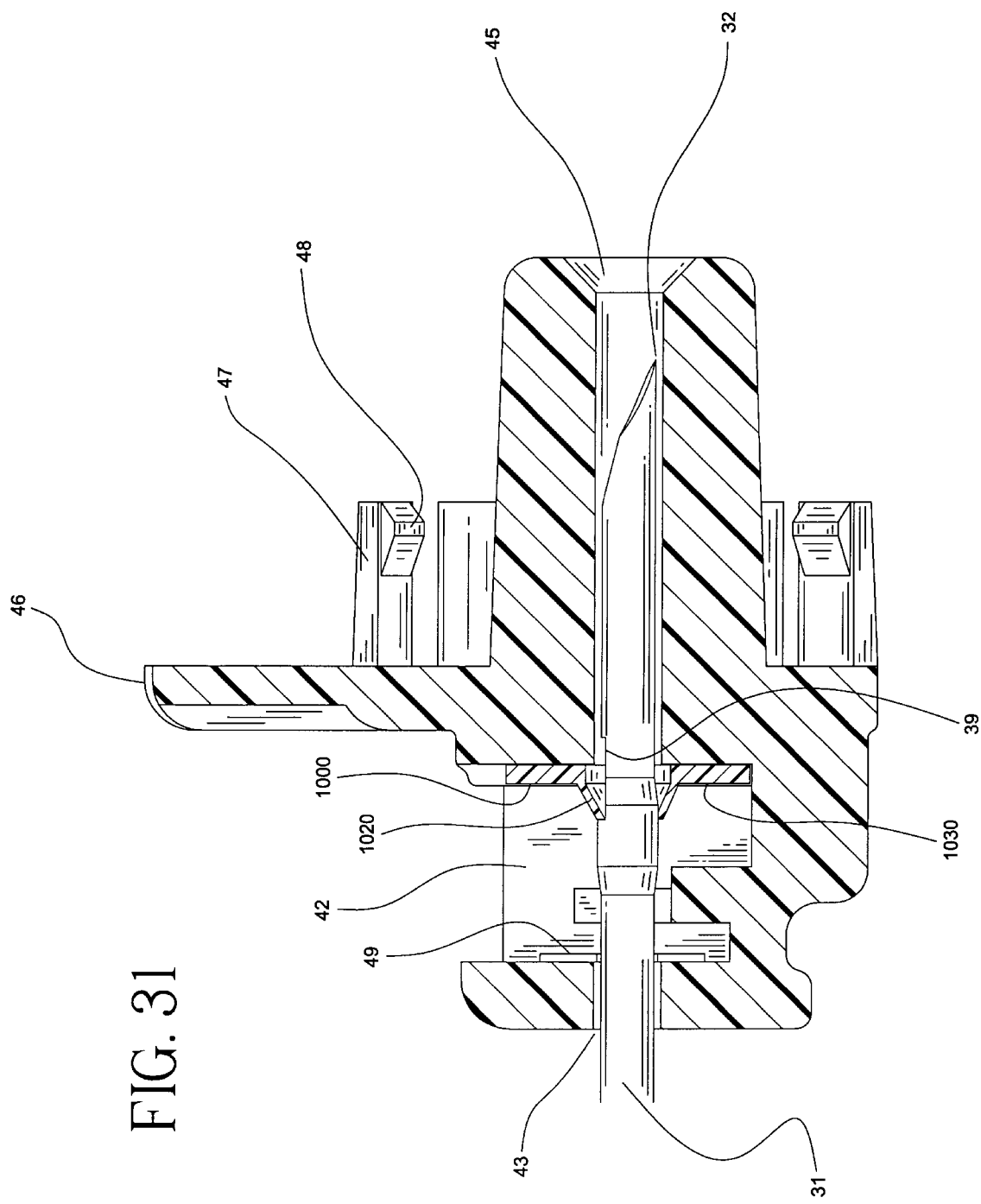
FIG. 31 is a cross-sectional view of the needle shield with the tenth embodiment of the lock that prevents unwanted distal movement of the introducer needle and the distal portion of the introducer needle shown in FIG.3F with the sharp distal tip of the introducer needle locked in the needle shield.
Figure 32:
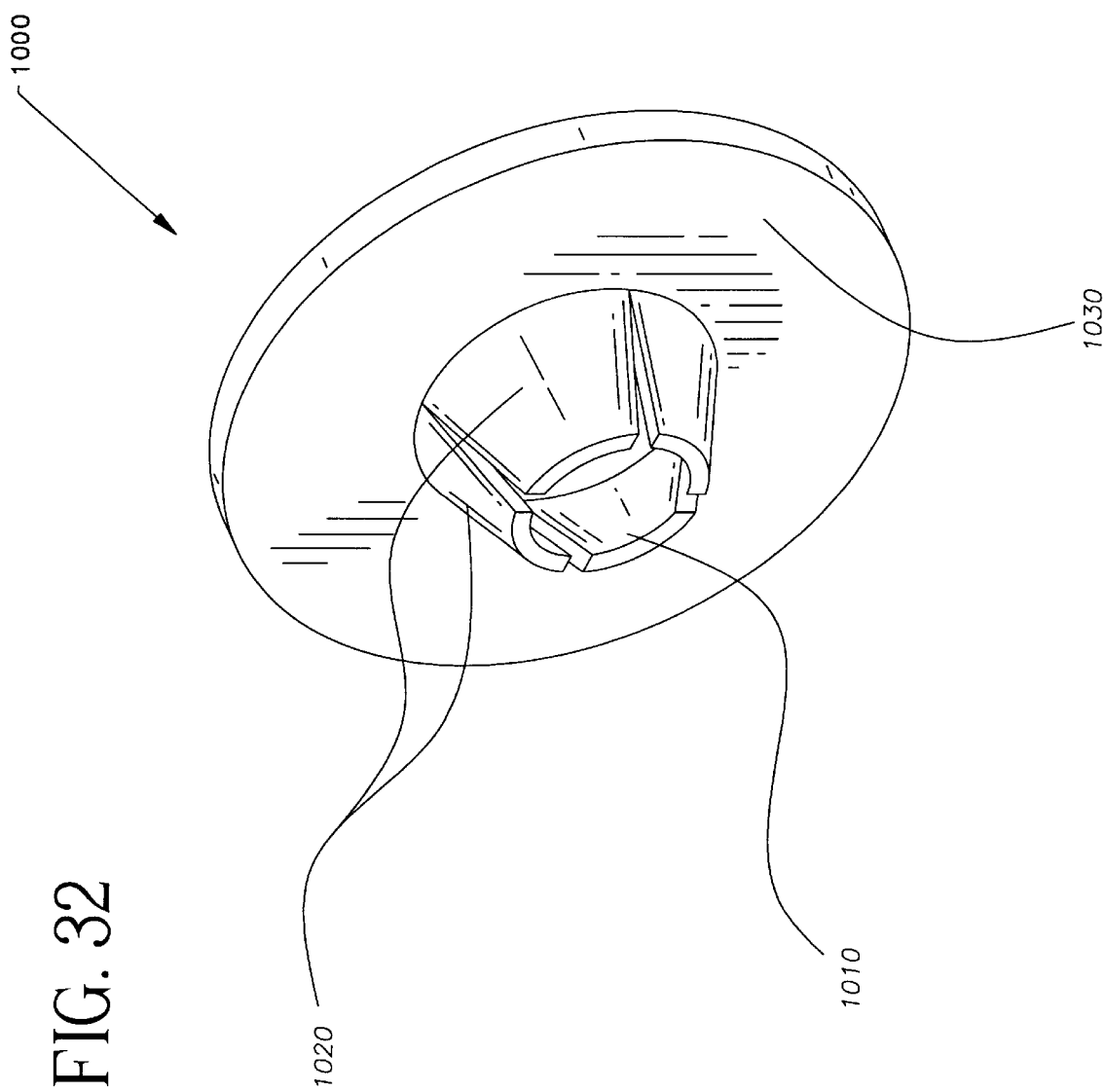
FIG. 32 is a perspective view of the speed nut that is the tenth embodiment of the lock shown in FIGS. 29 through 31 to prevent unwanted distal movement of the introducer needle.
Figure 33:
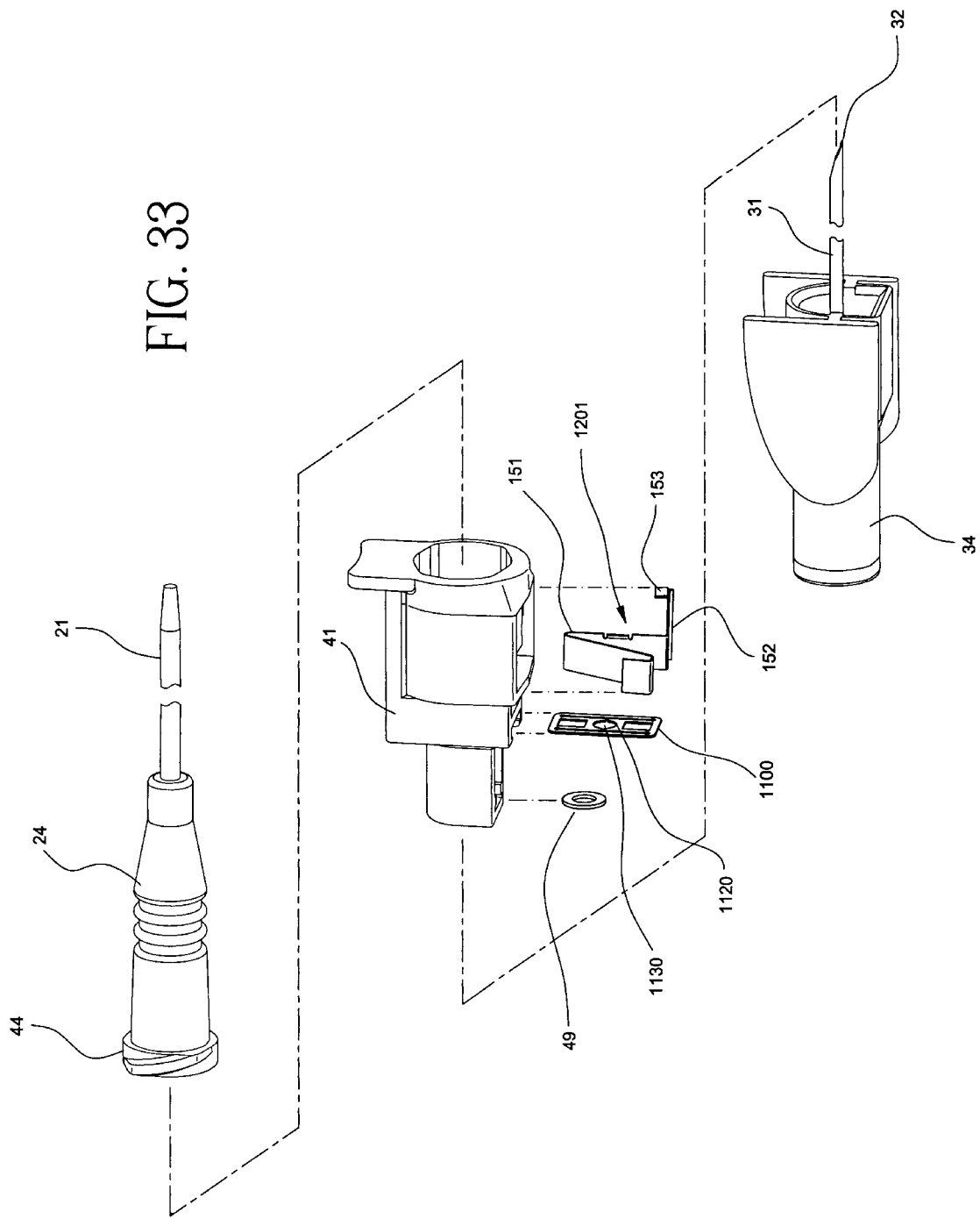
FIG. 33 is an exploded perspective view of a catheter, introducer needle and the needle shield with an eleventh embodiment of the lock that prevents unwanted distal movement of the introducer needle and a first embodiment of the spring clip that connects the needle shield to the catheter hub until the sharp distal tip of the introducer needle is locked in the needle shield.
Figure 34:
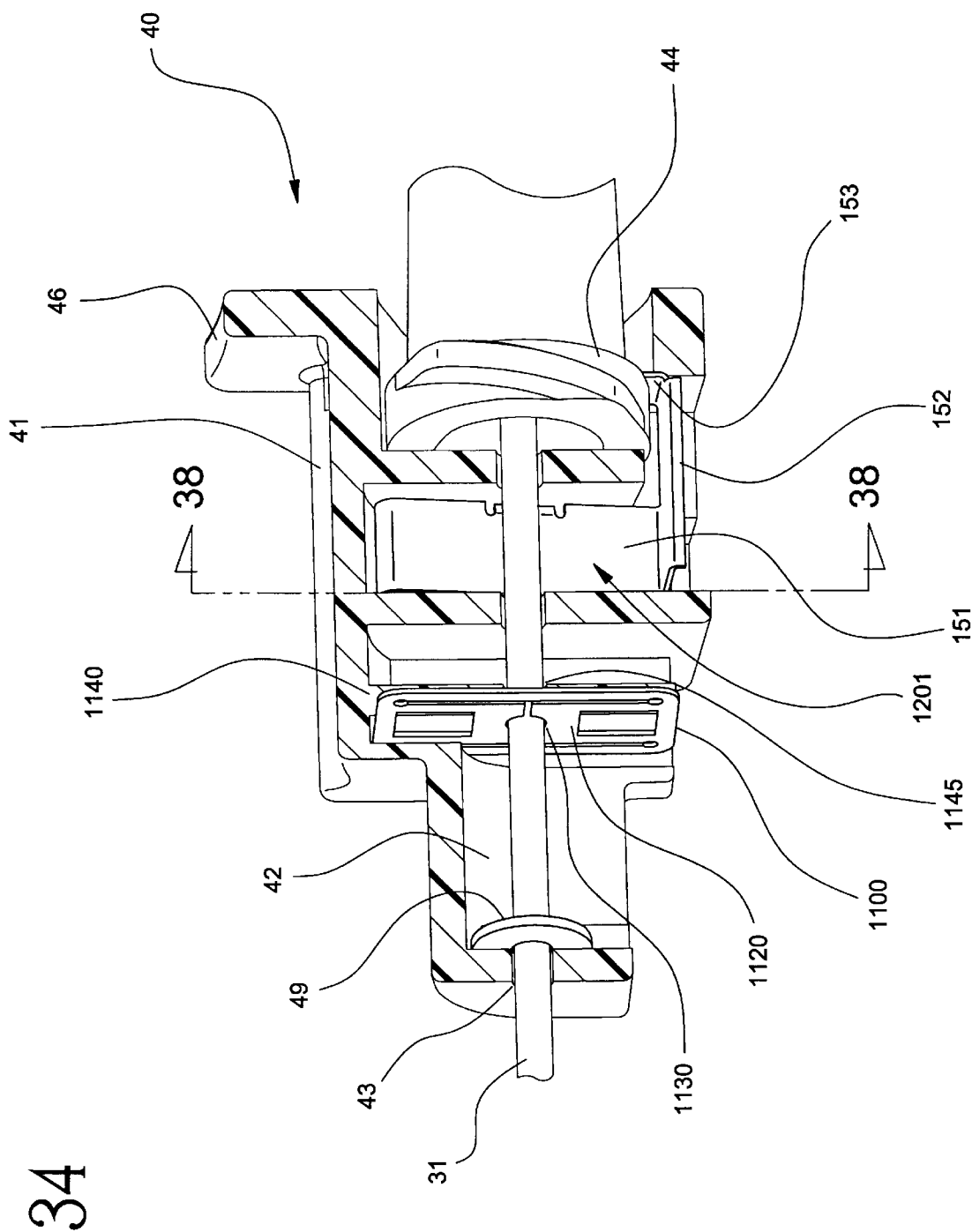
FIG. 34 is a partial cross-sectional view of the needle shield with the eleventh embodiment of the lock that prevents unwanted distal movement of the introducer needle, the first embodiment of the spring clip that connects the needle shield to the catheter hub until the sharp distal tip of the introducer needle is locked in the needle shield, a portion of the introducer needle and the proximal portion of the catheter hub with the sharp distal tip of the introducer needle extending from the distal end of in the needle shield and the needle shield connected to the catheter hub.
Figure 35:
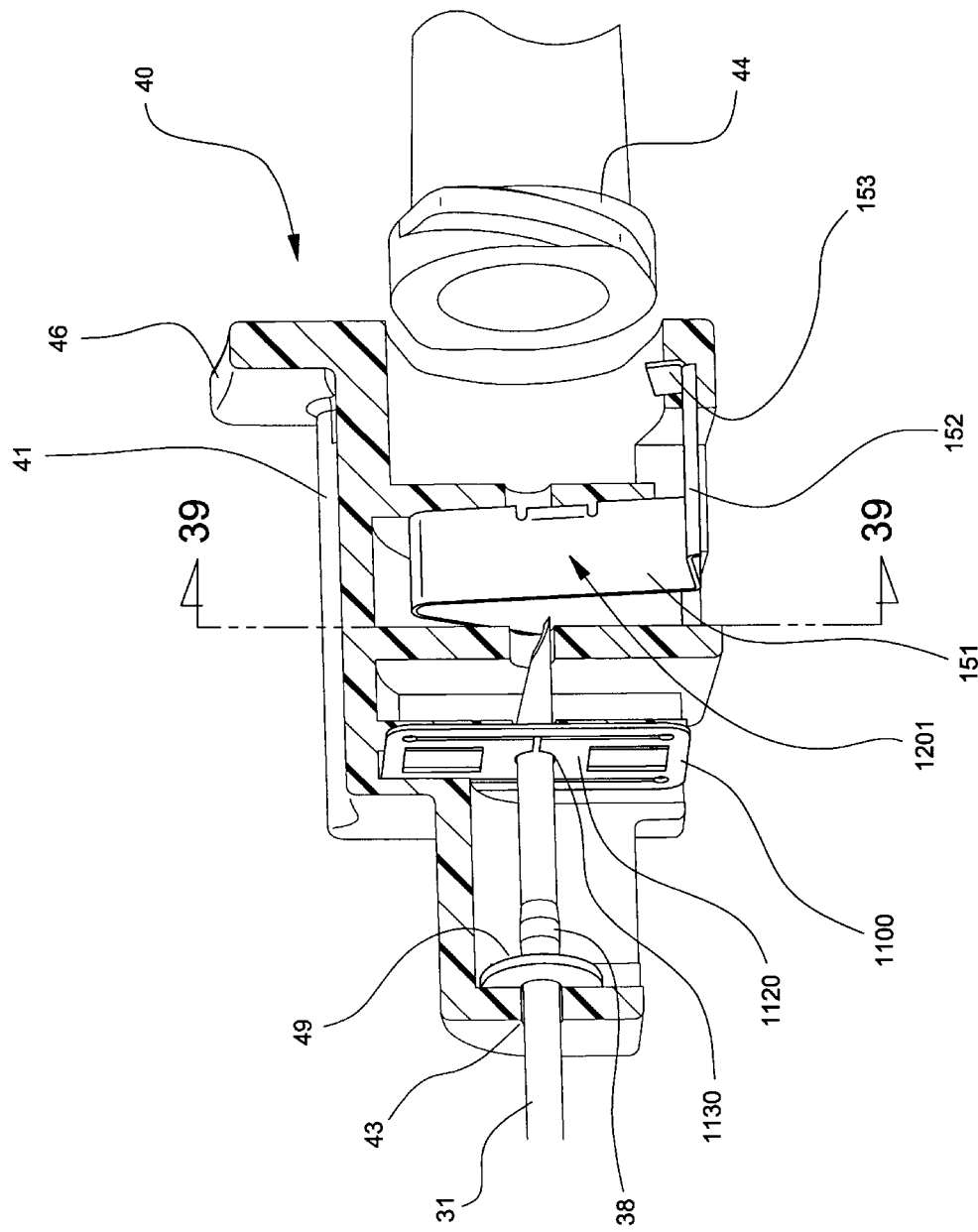
FIG. 35 is a partial cross-sectional view of the needle shield with the eleventh embodiment of the lock that prevents unwanted distal movement of the introducer needle, the first embodiment of the spring clip that connects the needle shield to the catheter hub until the sharp distal tip of the introducer needle is locked in the needle shield, the distal portion of the introducer needle and the proximal portion of the catheter hub with the sharp distal tip of the introducer needle locked in the needle shield and the needle shield disconnected from the catheter hub.

As shown in FIG. 31, the discontinuous portion of introducer needle 31 can be in the form of a notch 39 such as shown in FIGS. 3E, 3F and 3G. When introducer needle 31, and thus notch 39, is withdrawn through speed nut 1000, at least one tab 1020 will drop into notch 39. Any subsequent distal movement of introducer needle 31 will be prevented by the engagement of tab 1020 with the distally facing portion, i.e. the proximal edge, of notch 39. The use of a plurality of tabs 1020 formed around main body portion 1030 ensures that at least one tab 1020 will engage notch 39. Alternatively, a plurality of longitudinally displace notches 39 located about the circumference of introducer needle 31 could be used to catch tabs 1020.

When a notch 39 is used as the discontinuous portion on introducer needle 31, such as shown in FIG. 3D, instead of an enlarged diameter portion 38, a tether 50 connecting needle shield 40 to needle hub 34 may be used to prevent unwanted proximal movement of introducer needle 31 with respect to needle shield 40. Also, as described herein, tether 50 is a mechanism to prevent introducer needle 31 from being withdrawn proximally out of the proximal portion of needle shield 40 instead of the engagement of enlarged diameter portion 38 with proximal opening 43 or washer 49.

An eleventh embodiment of the lock that prevents unwanted distal movement of introducer needle 31 is shown in FIGS. 33 through 35, 37A, 37B and 37C. In this embodiment, the lock is a retention plate 1100, which includes tabs 1120 that do not extend proximally from the main portion of retention plate 1100. See specifically FIG. 37A. However, tabs 1120 are still connected to the main portion of retention plate 1100 via any appropriate mechanism, such as a living hinge, so that tabs 1120 are movable with respect to the main portion of retention plate 1100. Tabs 1120 define a through hole 1130 between the ends of each tab 1120 that has a diameter slightly greater than the diameter of the main portion of introducer needle 31 but is smaller than the diameter of enlarged diameter portion 38. Retention plate 1100 is located adjacent to the proximal face of a medial wall 1140 formed in cavity 42 of housing 41. Medial wall 1140 defines an opening 1145 therethrough that has a diameter greater than the diameter of enlarged diameter portion 38.

As introducer needle 31 is moved proximally into needle shield 40, enlarged diameter portion 38 can pass through opening 1145. In addition, enlarged diameter portion 38 can move past tabs 1120 since tabs 1120 will move proximally out of the way of enlarged diameter portion 38. However, once enlarged diameter portion 38 is moved proximal of retention plate 1100, any subsequent distal movement of introducer needle 31 with respect to needle shield 40 is prevented. This is because enlarged diameter portion 38 can not extend back through hole 1130 but instead engages the surface of tabs 1120 adjacent to hole 1130. In addition, tabs 1120 cannot move distally out of the way of enlarged diameter portion 38 because medial wall 1140 prevents any such distal movement of tabs 1120. Any further proximal movement of introducer needle 31 is prevented by proximal opening 43, washer 49 or tether 50.

Figure 37A:
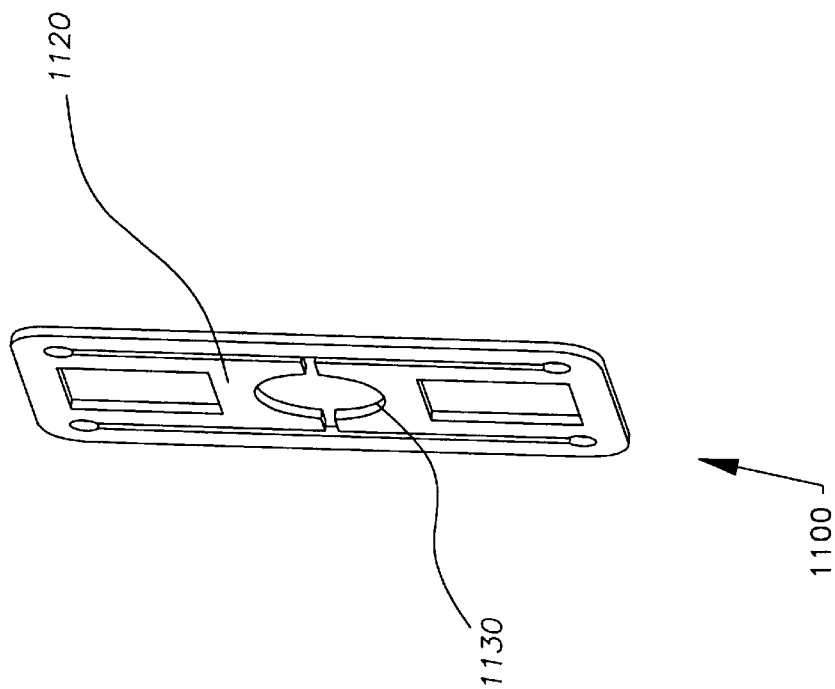
FIG. 37A is a perspective view of the retention plate that is the eleventh embodiment of the lock shown in FIGS. 33 through 35 that prevents unwanted distal movement of the introducer needle.
Figure 37B:
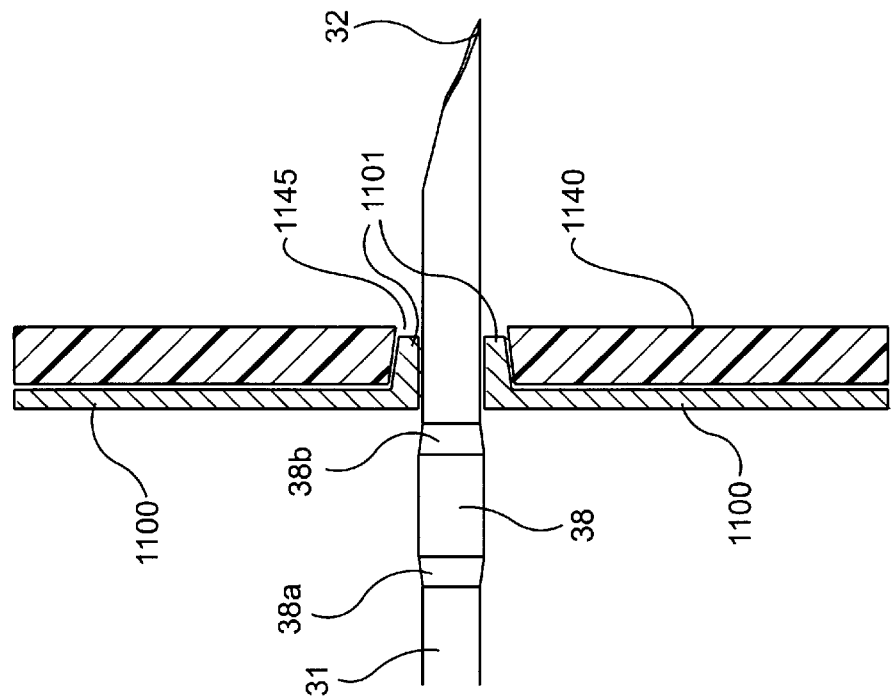
FIG. 37B is a schematic view, in partial cross-section, of a variation of the retention plate shown in FIG. 37A abutting the proximal face of the medial wall of the housing for the needle shield.
Figure 37C:
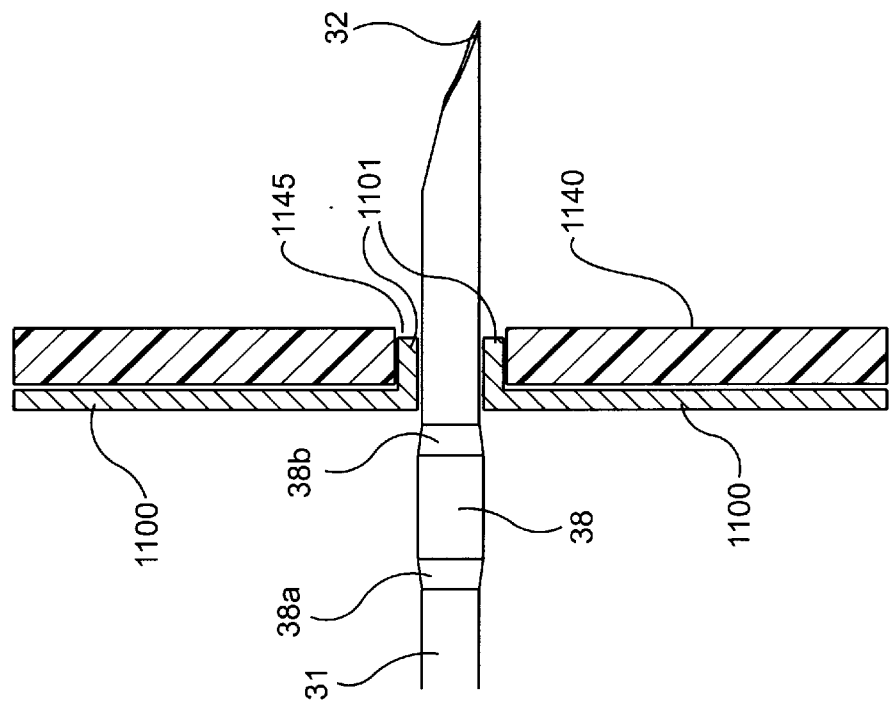
FIG. 37C is a schematic view, in partial cross-section, of still another variation of the retention plate shown in FIG. 37A abutting the proximal face of the medial wall of the housing for the needle shield.
Figure 38:
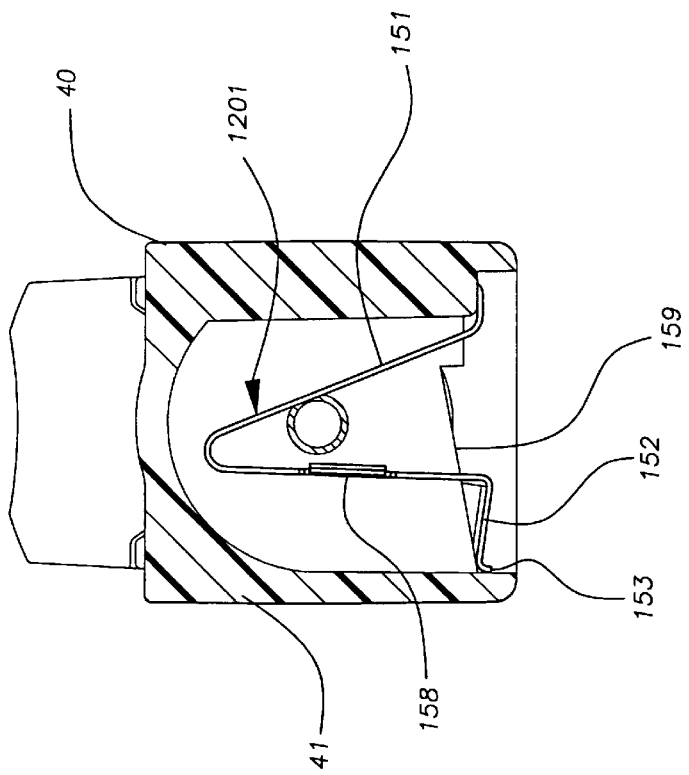
FIG. 38 is a cross-sectional view of the needle shield shown in FIG. 34 taken along line 38—38 showing how the clip arm of the spring clip would move along a ramp formed in the housing.
Figure 39:
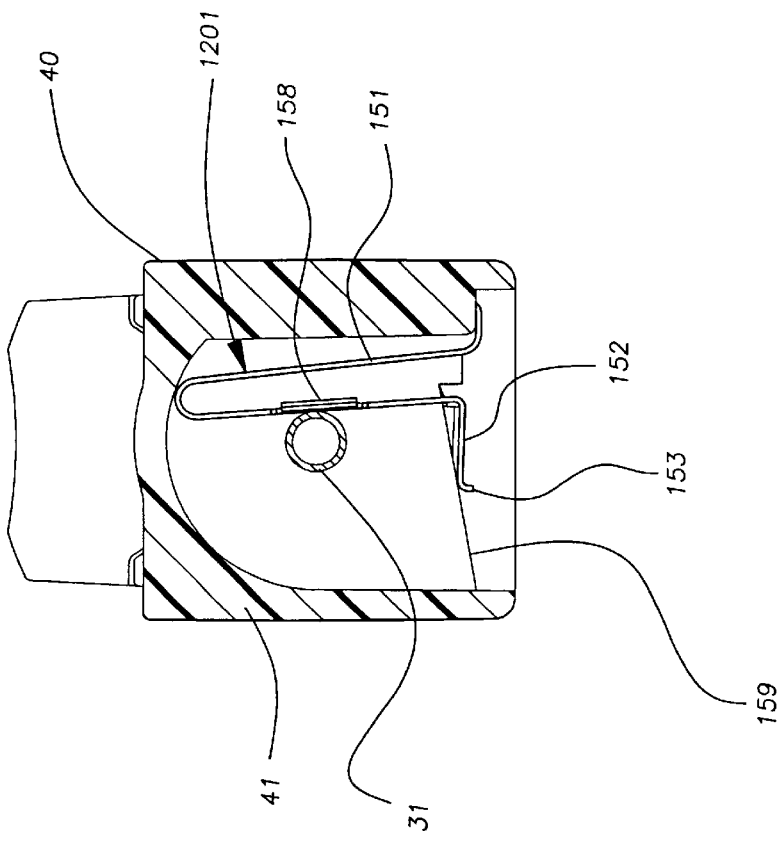
FIG. 39 is a cross-sectional view of the needle shield shown in FIG. 35 taken along line 39—39 showing how the clip arm of the spring clip would move along a ramp formed in the housing.

FIGS. 37B and 37C show variations of the retention plate shown in FIG. 37A. In both of these variations, tabs 1120 include distally extending fingers adjacent to hole 1130 such as to define the diameter of hole 1130. Fingers 1101 are shown in FIG. 37B and fingers 1101' are shown in FIG. 37C. In FIG. 37C, the outer portions of fingers 1101' are tapered so they slope toward introducer needle 31 in the distal direction and the inner walls defining opening 1145 have a complementary slope. Fingers 1101 and 1101' fill any excess space in opening 1145 in medial wall 1140 and ensure that unwanted distal movement of introducer needle 31. In the case of the variation shown in FIG. 37C, fingers 1101' provide a greater holding force to introducer needle 31 to prevent unwanted distal movement of introducer needle 31. This is because as introducer needle 31 is moved distally after enlarged diameter portion 38 has been moved proximal of retention platel 100, fingers 1101' will wedge into opening 1145 making it significantly more difficult to move introducer needle 31 distally.

FIGS. 33 through 36C, 38 and 39 show a first embodiment of a resilient spring clip 1201 that is used to connect needle shield 40 to catheter hub 24 until sharp distal tip 32 of introducer needle 31 has been withdrawn into needle shield 40. A spring arm 151 that is formed in a V-shaped configuration defines the spring clip. Spring arm 151 is disposed in housing 41 such that the apex of the V is pointed up toward the top of housing 41 and the legs defining the V straddle the longitudinal axis of introducer needle 31 when spring arm 151 is in its unbiased position. In this orientation, spring arm 151 is adapted for motion transverse to the longitudinal axis of introducer needle 31. This motion is along a defined path provided by a ramped surface 159 in housing 41. See FIGS. 38 and 39.

Of course spring arm 151 could be disposed in housing 41 such that the apex is oriented in other positions on a circle concentric to the longitudinal axis of introducer needle 31. All that is required is that spring arm 151 be adapted for motion transverse to the longitudinal axis of introducer needle 31. The apex of the V shape facilitates the flexing of spring arm 151 to and from a biased condition. In addition, the apex of the V shape could be in the form of a living hinge.

When sharp distal tip 32 of introducer needle 31 is distal of needle shield 40, introducer needle 31 abuts spring arm 151 so as to hold spring arm 151 in the biased, unactivated, clipped position. Spring arm 151 includes a clip arm 152 which extends generally parallel to the longitudinal axis of introducer needle 31. Clip arm 152 preferably has a finger 153 formed thereon, which is adapted to engage thread 44 or a corresponding detent 26 formed on catheter hub 24 when spring arm 151 is in the clipped position. Detent 26 can be the flange or luer locking ears 44 shown on the proximal end of catheter hub 24. Alternatively, detent 26 can take the form of a notch or slot, or an upstanding peg. Although the use of finger 153 and detent 26 is preferred because it provides positive mechanical engagement therebetween, these elements are not necessary. Without any detents the engagement force between clip arm 152 and catheter hub 24 is limited to frictional force which may be easier to overcome than with mechanical engagement. However, in certain situations, this frictional force may be sufficient.

When sharp distal tip 32 of introducer needle 31 is moved proximally into needle shield 40 so that introducer needle 31 no longer abuts spring arm 151, spring arm 151 can flex to its unbiased, activated non-clipped position out of engagement with catheter hub 24. This allows catheter hub 24 to be disconnected from needle shield 40. Spring arm 151 may include a longitudinally extending flag 158 that minimizes drag on introducer needle 31, and enlarged diameter portion 38 if any, as introducer needle 31 is being moved proximally into needle shield 40. In addition, spring arm 151 may include an arm 53 extending therefrom and which defines an opening therein. In one embodiment, arm 53 also includes a longitudinally extending guide rail 51 that guides introducer needle 31 toward opening 52. See FIG. 36B. The diameter of opening 52 is slightly greater than the diameter of the main portion of introducer needle 31 but is smaller than the diameter of enlarged diameter portion 38. Thus spring clip 151 can work to prevent unwanted distal movement of introducer needle 31 in a similar manner to the leaf spring 700 shown in FIGS. 19–21. In an alternative embodiment, a tapered opening 54 can be used instead. See FIG. 36. All that is required is for opening 54 to define a portion that allows the main portion of introducer needle 31 to extend therethrough and to define a portion that does not allow the enlarged diameter portion 38 to extend therethrough.

It is to be understood that the various embodiments of the resilient spring clips discussed hereinafter can be used in conjunction with any of the previous embodiments of the lock that prevents unwanted distal movement of sharp distal tip 32 of introducer needle 31 out of the distal end of needle shield 40 once sharp distal tip 32 has been proximally withdrawn into needle shield 40. Preferably, the resilient spring clips are formed from stainless steel. However, it is to be understood that other flexible, strong materials could also be used to form the resilient spring clips.

As previously mentioned, the V-shaped configuration of spring arm 151 ensures that it can flex between a clipped, i.e. a biased and an unactivated, position and a non-clipped, i.e. an unbiased and an activated, position. In the unactivated position, finger 153 is positioned into engagement with catheter hub 24. See FIG. 34. In the activated position, finger 153 is not in engagement with catheter hub 24. See FIG. 35. Preferably, housing 41 defines a ramp 159 extending transversely to the longitudinal axis of introducer needle 31. See FIGS. 38 and 39. Ramp 159 is located in housing 41 such that it engages clip arm 152. Ramp 159 acts as a guide for clip arm 152 to ensure clip arm 152 and finger 153 do not rotate around catheter hub 24 but instead move transversely to the longitudinal axis of introducer needle 31 once sharp distal tip 31 is withdrawn proximally of spring arm 151 out of engagement with catheter hub 24.

Although this V-shaped configuration for spring clip 1201 is preferred, many different configurations may be used. All that is required is that the orientation allows spring arm 151 to flex so clip arm 152 and finger 153 can be moved into engagement with catheter hub 24 and can move to an activated position out of engagement with catheter hub 24.

Figure 40:
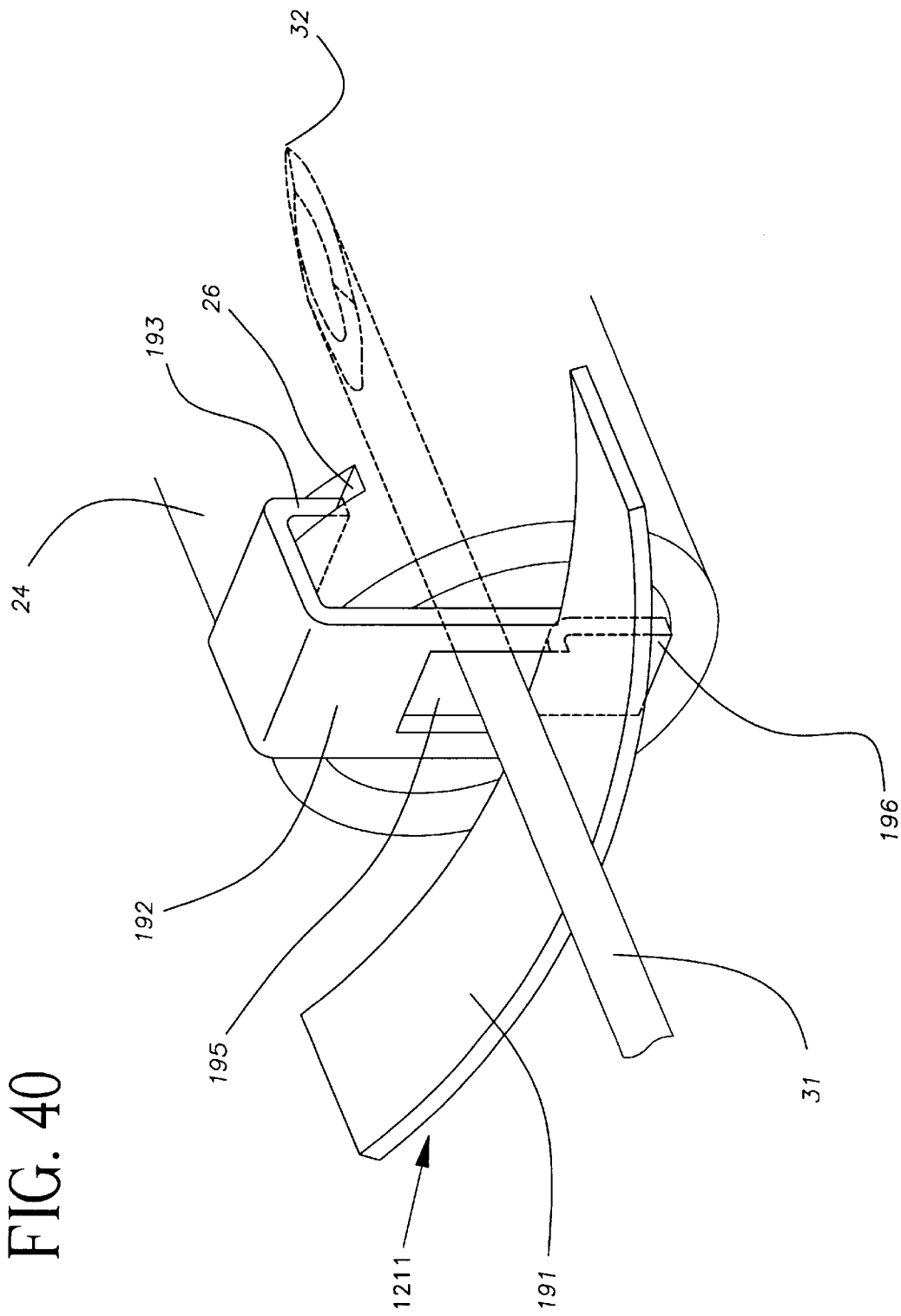
FIG. 40 is a schematic perspective view of a first embodiment of the spring clip with a transverse barrier that connects the needle shield to the catheter hub until the sharp distal tip of the introducer needle is locked in the needle shield and a portion of the introducer needle and a portion of the catheter hub where the sharp distal tip of the introducer needle would be extending from the distal end of the needle shield and the needle shield would be connected to the catheter hub.
Figure 41:
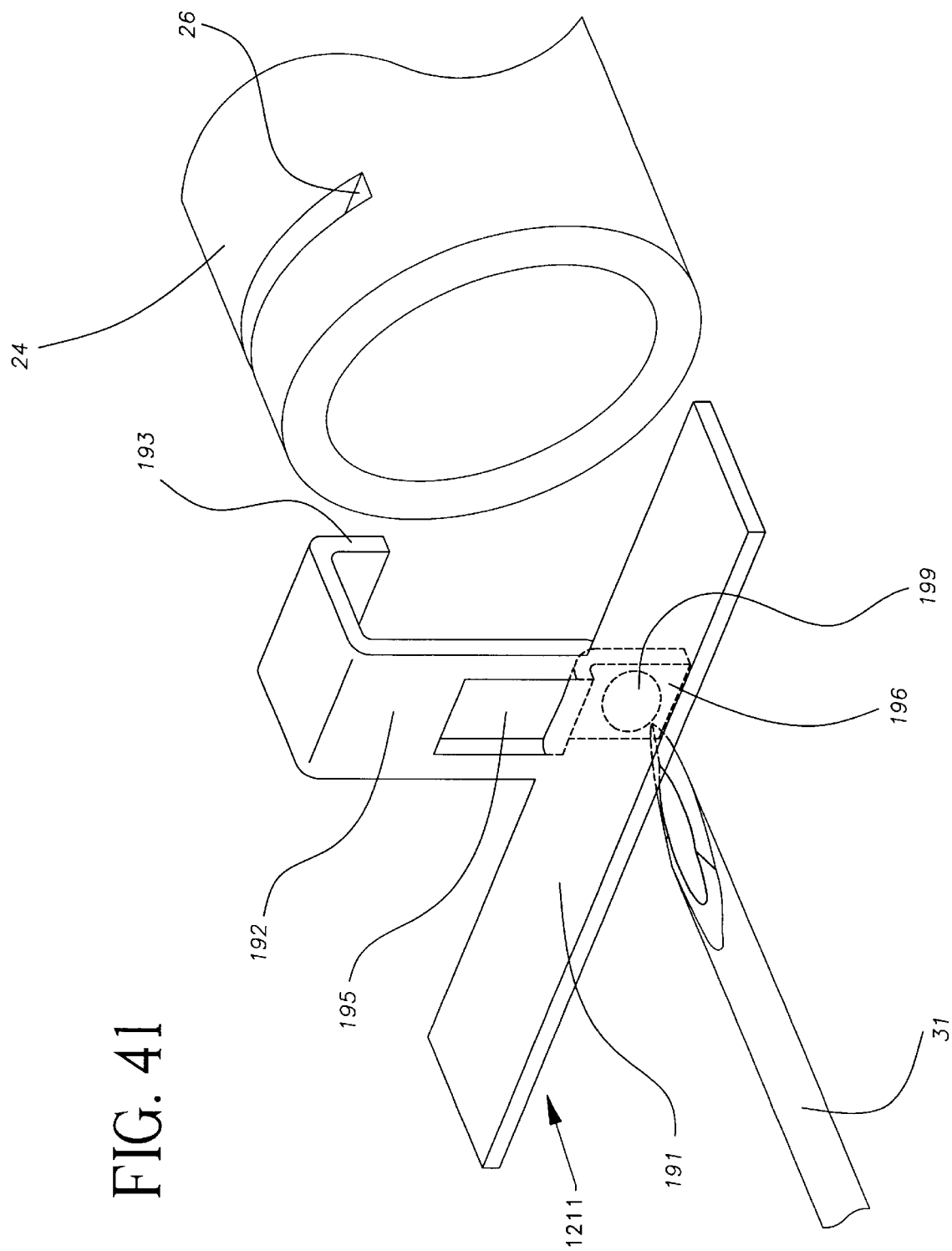
FIG. 41 is a schematic perspective view of the spring clip shown in FIG. 40 where the sharp distal tip of the introducer needle would be locked in the needle shield and the needle shield would be disconnected from the catheter hub.

A first embodiment of a spring clip 1211 with a transverse barrier can be seen in FIGS. 40 and 41. Spring clip 1211 is formed from spring arm 191 and clip arm 192. In this embodiment, spring arm 191 is a resilient, substantially straight and unbent member. Clip arm 192 defines a hole 195 through which introducer needle 31 extends. Spring arm 191 is oriented generally perpendicular to introducer needle 31 such that the ends of spring arm 191 are fixed to housing 41. Thus, in the unbiased, i.e. activated non-clipped position, hole 195 is not longitudinally aligned with introducer needle 31. See FIG. 41. Although the FIGS. show introducer needle 31 above spring arm 191, it is to be understood that introducer needle 31 could be below spring arm 191 and spring arm 191 could be located within housing 41 such that it extends across the diameter, in any orientation, of a circle concentric to the longitudinal axis of introducer needle 31.

When introducer needle 31 extends through hole 195 and past the distal end of needle shield 40 and into catheter hub 24, spring arm 191 abuts introducer needle 31 and is prevented from moving out of engagement with catheter hub 24. See FIG. 40. Clip arm 192 preferably extends perpendicular to spring arm 191 and includes a finger 193 formed thereon. In addition, catheter hub 24 also includes a detent 26 thereon for engagement with finger 193. As discussed above, detent 26 can be a flange or luer locking ears on the proximal end of catheter hub 24. Alternatively, detent 26 can take the form of a notch or slot, or an upstanding peg. When introducer needle 31 extends past spring arm 191, finger 193 engages a detent 26 on catheter hub 24 to maximize the retention force between clip arm 192 and catheter hub 24. Thus, as long as introducer needle 31 extends distally past spring arm 191, clip arm 192 and detent 26 remain engaged so catheter hub 24 stays connected with needle shield 40. Once sharp distal tip 32 of introducer needle 31 is withdrawn proximally past spring arm 191, clip arm 192 returns to its activated, unbiased, non-clipped position so that finger 193 can move out of engagement with detent 26. This allows catheter hub 24 to be separated from needle shield 40.

Spring clip 1211 of this embodiment also includes a transverse barrier 196, which extends perpendicular to an below spring arm 191 to prevent unwanted distal movement of introducer needle 31. Thus when sharp distal tip 32 is moved proximally past spring arm 191, transverse barrier 196 acts as a positive barrier to engage sharp distal tip 32 of introducer needle 31 to prevent unwanted distal movement of introducer needle 31. With this embodiment, no discontinuous portion 38 is needed on introducer needle 31 and a tether 50 may be used to prevent unwanted proximal movement of introducer needle 31.

However, if desired, discontinuous portion 38 could be used on introducer needle to prevent unwanted distal movement of introducer needle 31. In that case, transverse barrier 196 could be formed with an opening 199 therein having a diameter smaller than the diameter of enlarged diameter portion 38. Opening 199 thus would prevent unwanted distal movement of introducer needle 31 similar to leaf spring 700 shown in FIGS. 19–21. Indeed, all of the transverse barriers discussed herein could be modified if desired to include an opening therein that would not allow enlarged diameter portion 38 to pass therethrough.

Although the foregoing embodiments of the spring clips engage the outside of catheter hub 24, it is to be understood that the spring clips and introducer needle 31 could be arranged such that the spring clips engage the inside of catheter hub 24. For example, the spring clips could be arranged with respect to introducer needle 31 so that introducer needle 31 pushes the locking arms radially outwardly. Once sharp distal tip 32 of introducer needle 31 is moved proximally past the spring arms, they return to their unbiased position and move the locking arms inwardly toward the longitudinal axis of needle shield 40.

FIGS. 42 through 45 show a second embodiment of a spring clip 1212 with a transverse barrier that connects catheter hub 24 to needle shield 40 until sharp distal tip 32 has been locked in needle shield 40. Spring clip 1212 of this embodiment is substantially the same as the embodiment for the spring clip shown in FIGS. 33 through 36C, 38 and 39 except for the addition of transverse barrier 296. Thus this embodiment of spring clip 1212 functions to connect catheter hub 24 to needle shield 40 until sharp distal tip 32 has been locked in needle shield 40 in substantially the same way as the embodiment shown in FIGS. 33 through 36C, 38 and 39.

Figure 36A:
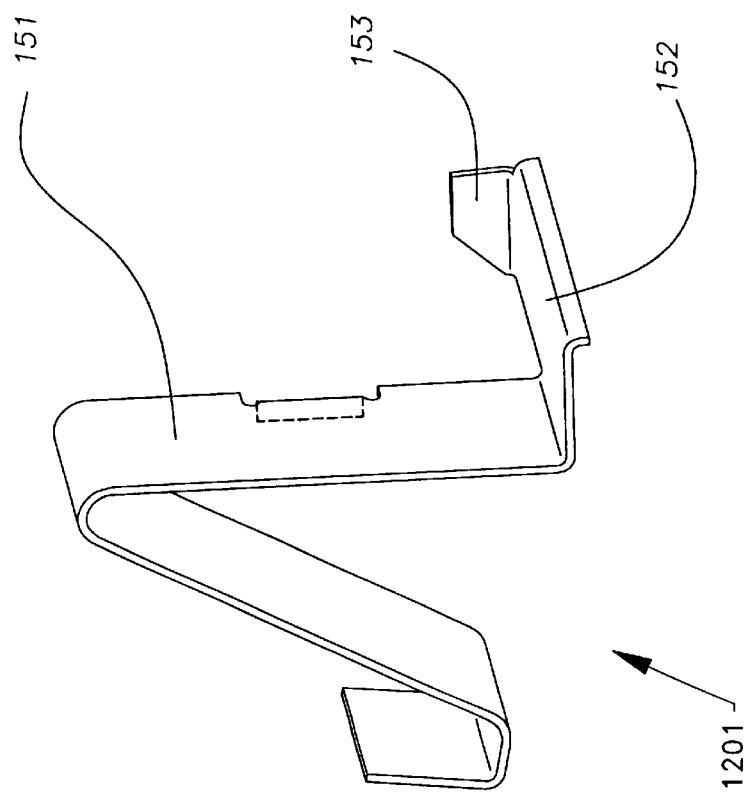
FIG. 36A is a perspective view of the first embodiment of the spring clip shown in FIGS. 33 through 35 that connects the needle shield to the catheter hub until the sharp distal tip of the introducer needle is locked in the needle shield.

When introducer needle 31 extends through needle shield 40 so that sharp distal tip 32 is distal of distal opening 45, spring arm 291 abuts the shaft of introducer needle 31 and is biased to move transverse barrier 296 in front of sharp distal tip 32. Once sharp distal tip 32 is moved proximally past spring arm 291, spring arm 291 moves to its activated, unbiased, non-clipped position so that transverse barrier 296 is in front of sharp distal tip 32. This prevents any unwanted distal movement of introducer needle 31.

Where transverse barrier 296 is used, preferably a tether 50 is used to connect needle shield 40 to needle hub 34. Tether 50 prevents unwanted proximal movement of introducer needle 31 with respect to needle shield 40. Tether 50 can take many different forms such as a string, a pleated element, a sleeve member surrounding introducer needle 31 or a plurality of telescoping members surrounding introducer needle 31. Alternatively, where transverse barrier 296 is used, unwanted proximal movement of introducer needle 31 can be prevented in the same manner as the embodiments previously discussed. As such, introducer needle 31 can be formed with enlarged diameter portion 38, which would abut proximal opening 43 or washer 49.

Where enlarged diameter portion 38 is used on introducer needle 31, spring clip 1212 could be formed as shown in FIG. 36B or 36C. As discussed above, in those embodiments, the spring clip is formed with an arm 53 extending therefrom similarly to transverse barrier 296. However, arm 53 defines an opening 52 or 54 therein. Opening 54 is tapered from a larger diameter portion to a smaller diameter portion. In both cases, opening 52 and 54 define a portion that has a diameter that is smaller than the diameter of enlarged diameter portion 38. Thus, after spring clip 1212 moves to the non-clipped position, opening 52 and 54 will be substantially aligned with introducer needle 31. However, unwanted distal movement of introducer needle 31 will be prevented because the smaller diameter portion of opening 52 and 54 will prevent the passage of enlarged diameter portion 38 therethrough. Similarly, opening 199 shown in the embodiment of FIG. 45 can cooperate with enlarged diameter portion 38 to prevent unwanted distal movement of introducer needle 31.

A first embodiment of an integrated clip lock 1221 that connects needle shield 40 to catheter hub 24 and that prevents unwanted distal movement of sharp distal tip 32 of introducer needle 31 is shown in FIGS. 46 through 49. In this embodiment, integrated clip lock 1221 is formed with a spring arm 2191 having a substantially U-shaped configuration with two legs 2192 wherein the base of legs 2192 is formed as the retention plate shown in FIG. 37A. Spring arm 2191 is configured such that it is biased outwardly and can flex into and out of engagement with catheter hub 24. Preferably, spring arm 2191 is oriented in housing 41 such that the base of the U is oriented toward the proximal portion of needle shield 40 and legs 2192 are oriented generally parallel to the longitudinal axis of introducer needle 31. As discussed in connection with other embodiments, integrated clip lock 1221 could have a single leg and a substantially L-shaped configuration. See for example FIGS. 55 through 57. Extending radially inwardly from each leg 2192 is a biasing arm 2193. A hole 2194 is defined in each biasing arm 2193 to allow introducer needle 31 to extend therethrough. If desired, a flap 2199 is located adjacent to each hole 2194 extending generally parallel to introducer needle 31. These flaps 2199 could take the form of turned ends on the biasing arms 2193 or the cut out flap portion of biasing arms 2193 that are cut to form holes 2194. Flaps 2199 minimize drag on introducer needle 31 as it is withdrawn proximally into needle shield 40 through holes 2194.

In addition, the distal portion of each leg 2192 defines a hole 2195 therethrough. Holes 2195 are adapted to engage detent 26 formed on the proximal end of catheter hub 24. As discussed above, detent 26 can have any suitable configuration and the distal portion of each leg 2192 could likewise have any complementary configuration so detent 26 and the distal portion of each leg 2192 could be engaged.

When sharp distal tip 32 of introducer needle 31 extends past the distal end of needle shield 40 into catheter hub 24, introducer needle 31 also extends through holes 2194 of biasing arms 2193. This pulls legs 2192 inwardly toward catheter hub 24 so holes 2195 engage detent 26. This maintains needle shield 40 connected to catheter hub 24 as long as sharp distal tip 32 of introducer needle 31 is distal of biasing arms 2193. Once introducer needle 31 is pulled proximal of biasing arms 2193, legs 2192 are free to return to their unbiased, activated, non-clipped position where holes 2195 no longer engage detent 26. Thus, spring arm 2191 can flex into and out of engagement with catheter hub 24.

Discontinuous portion 38 on introducer needle 31 interacts with the proximal wall as discussed above to prevent unwanted proximal movement of introducer needle 31 and with retention plate 1100 to prevent unwanted distal movement of introducer needle 31.

Figure 50:
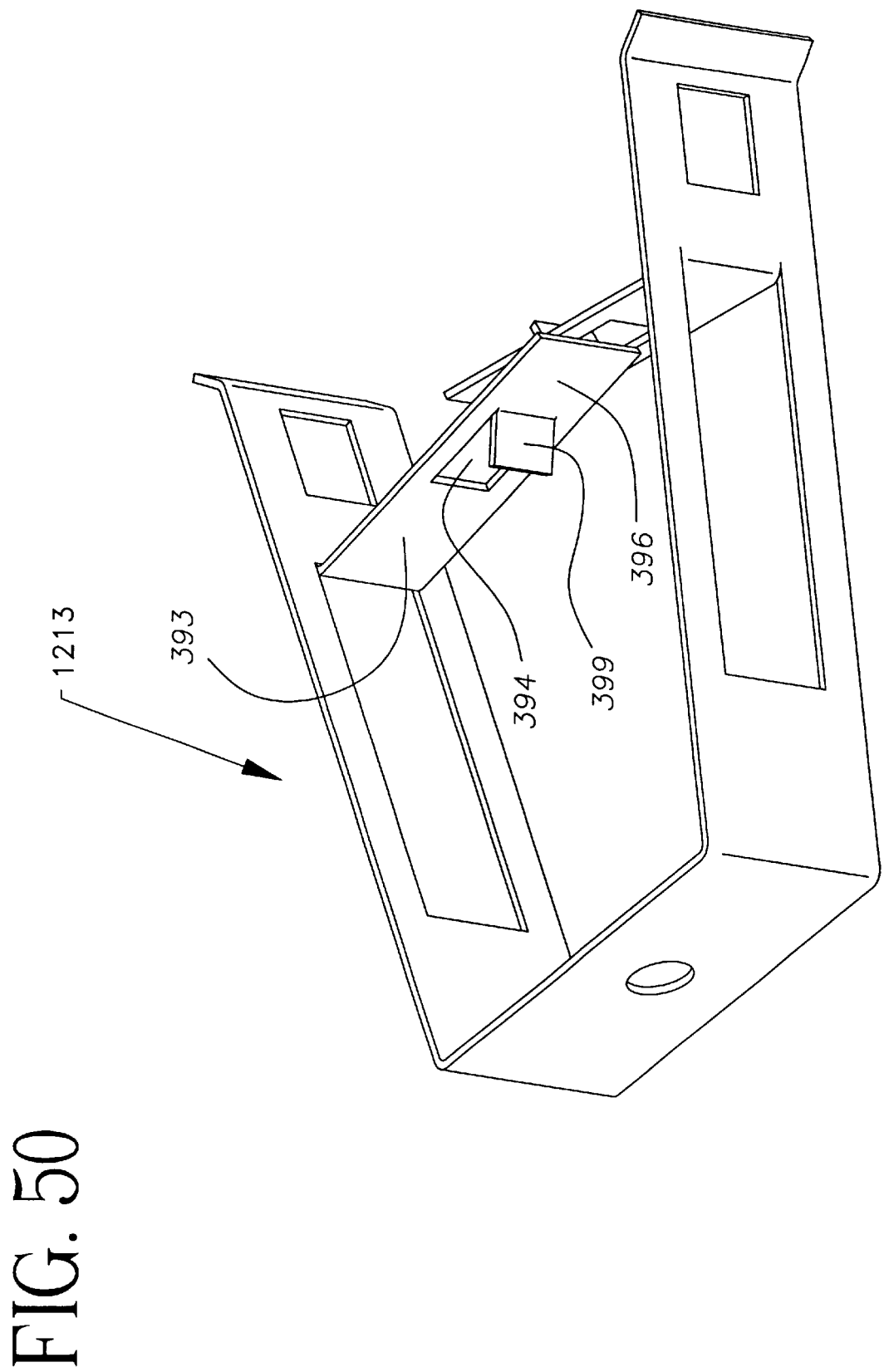
FIG. 50 is a perspective view of a third embodiment of a spring clip with a transverse barrier that connects the needle shield to the catheter hub until the sharp distal tip of the introducer needle is locked in the needle shield.

Alternatively, where it is desired to omit discontinuous portion 38 from introducer needle 31 one of the biasing arms could be formed with an extended portion that acts as a transverse barrier. See FIG. 50. In this third embodiment of the spring clip 1213 having a transverse barrier that connects catheter hub 24 to needle shield 40 until sharp distal tip 32 has been locked in needle shield 40, the transverse barrier 396 prevents subsequent distal movement of introducer needle 31 once sharp distal tip 32 is withdrawn proximally of biasing arms 393. In addition, in this embodiment, a tether 50 would have to be used to connect needle shield 40 and needle hub 34 together to prevent unwanted proximal movement of introducer needle 31 with respect to needle shield 40 once sharp distal tip 32 is withdrawn into needle shield 40. This embodiment of spring clip 1213 operates in substantially the same manner as the spring clip portion of integrated clip lock 1221 shown in the previous embodiment of FIGS. 46–49.

As with the previous embodiment, each biasing arm 393 preferably has a flap 399 located adjacent to holes 394 extending generally parallel to introducer needle 31. Flaps 399 minimize drag on introducer needle 31 as it is withdrawn proximally into needle shield 40 through holes 394.

Figure 51:
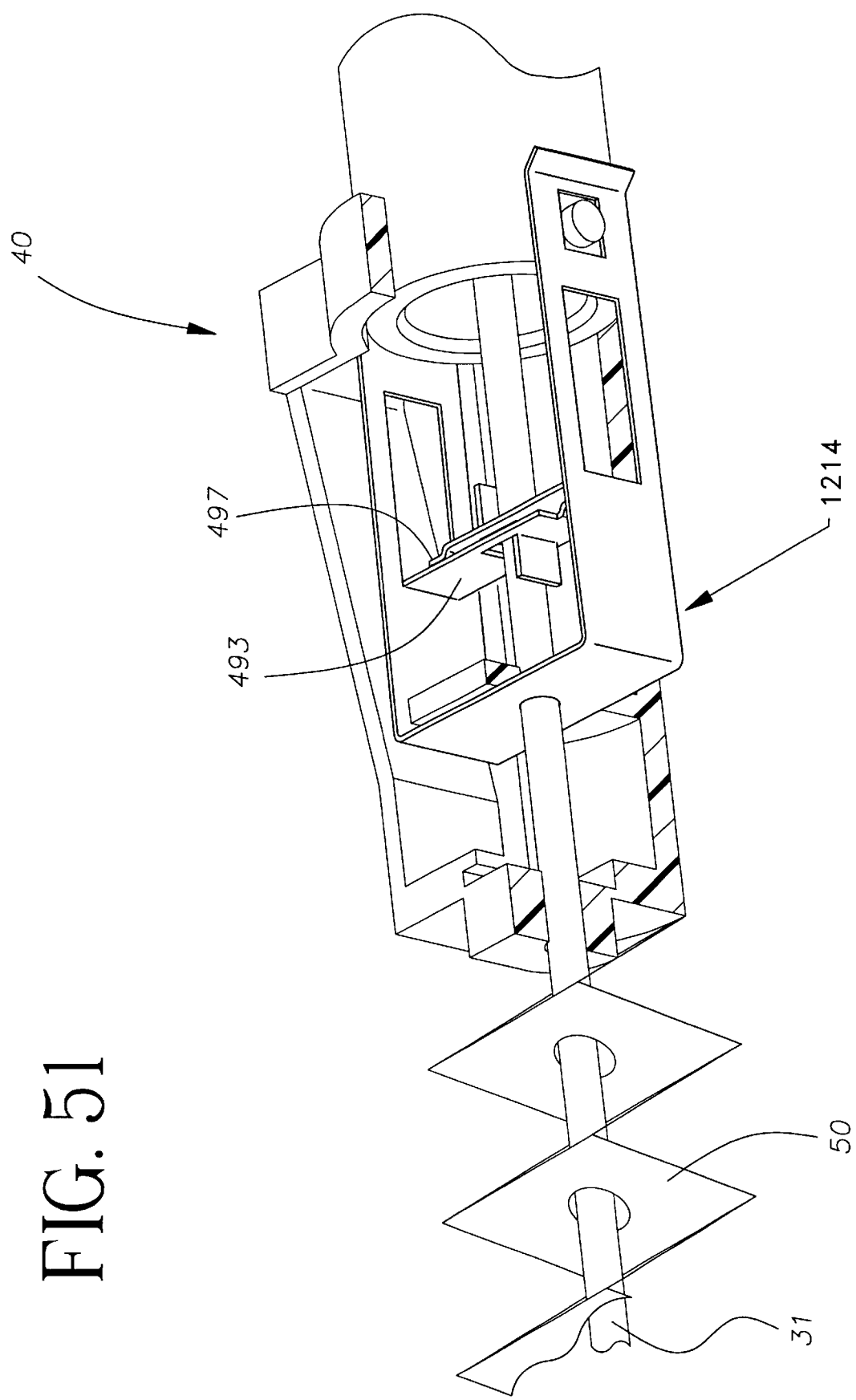
FIG. 51 is a perspective partial cross-sectional view of a fourth embodiment of a spring clip with a transverse barrier that connects the needle shield to the catheter hub until the sharp distal tip of the introducer needle is locked in the needle shield, a portion of the introducer needle, a portion of the tether and the proximal portion of the catheter hub with the sharp distal tip of the introducer needle extending from the distal end of in the needle shield and the needle shield connected to the catheter hub and a first embodiment of an interlock that prevents defeat of the transverse barrier.
Figure 52:
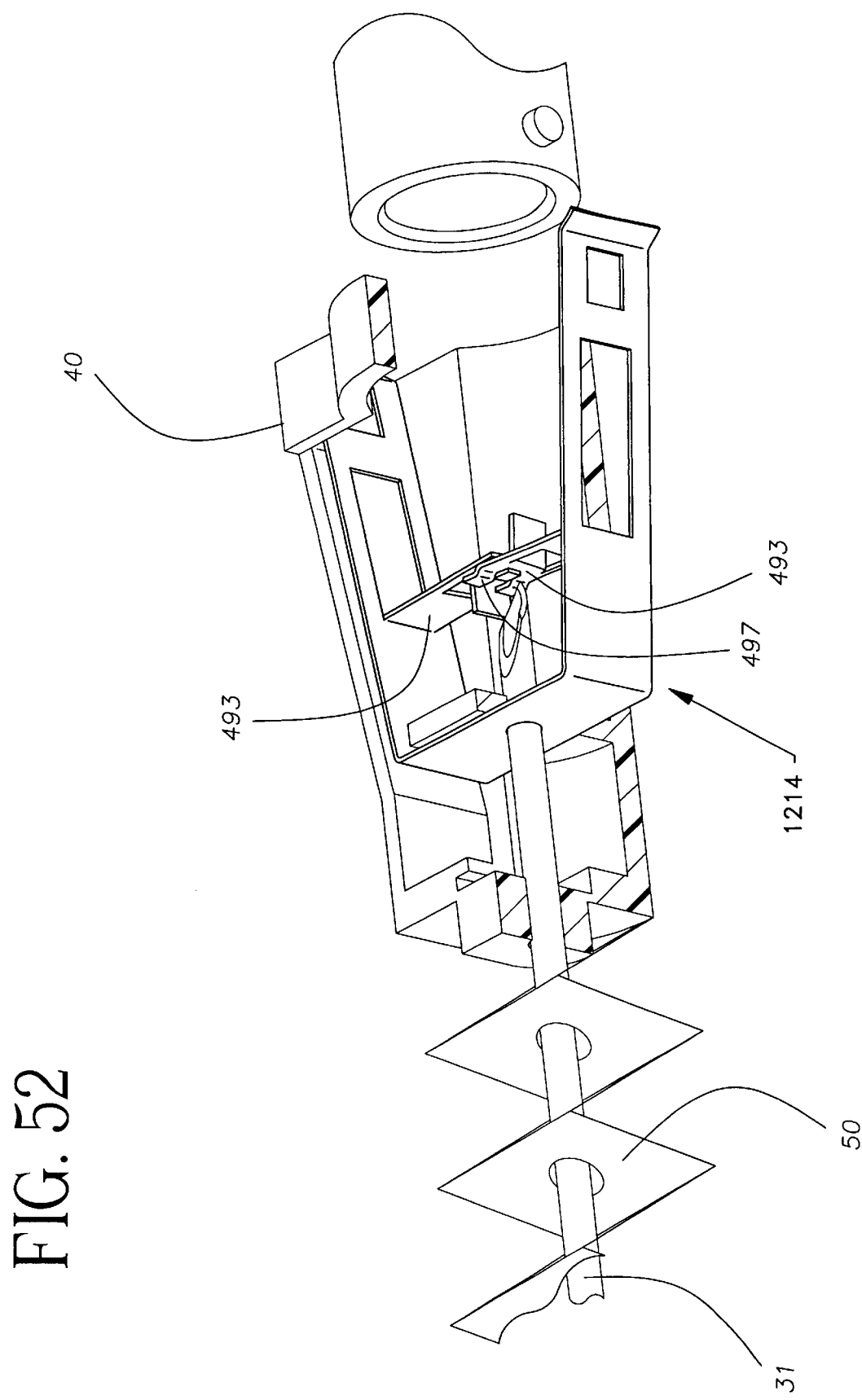
FIG. 52 is a perspective partial cross-sectional view of the needle shield with the fourth embodiment of the spring clip with a transverse barrier that connects the needle shield to the catheter hub until the sharp distal tip of the introducer needle is locked in the needle shield, the distal portion of the introducer needle, the distal portion of the tether and the proximal portion of the catheter hub with the sharp distal tip of the introducer needle locked in the needle shield and the needle shield disconnected from the catheter hub and a first embodiment of an interlock that prevents defeat of the transverse barrier.
Figure 53:
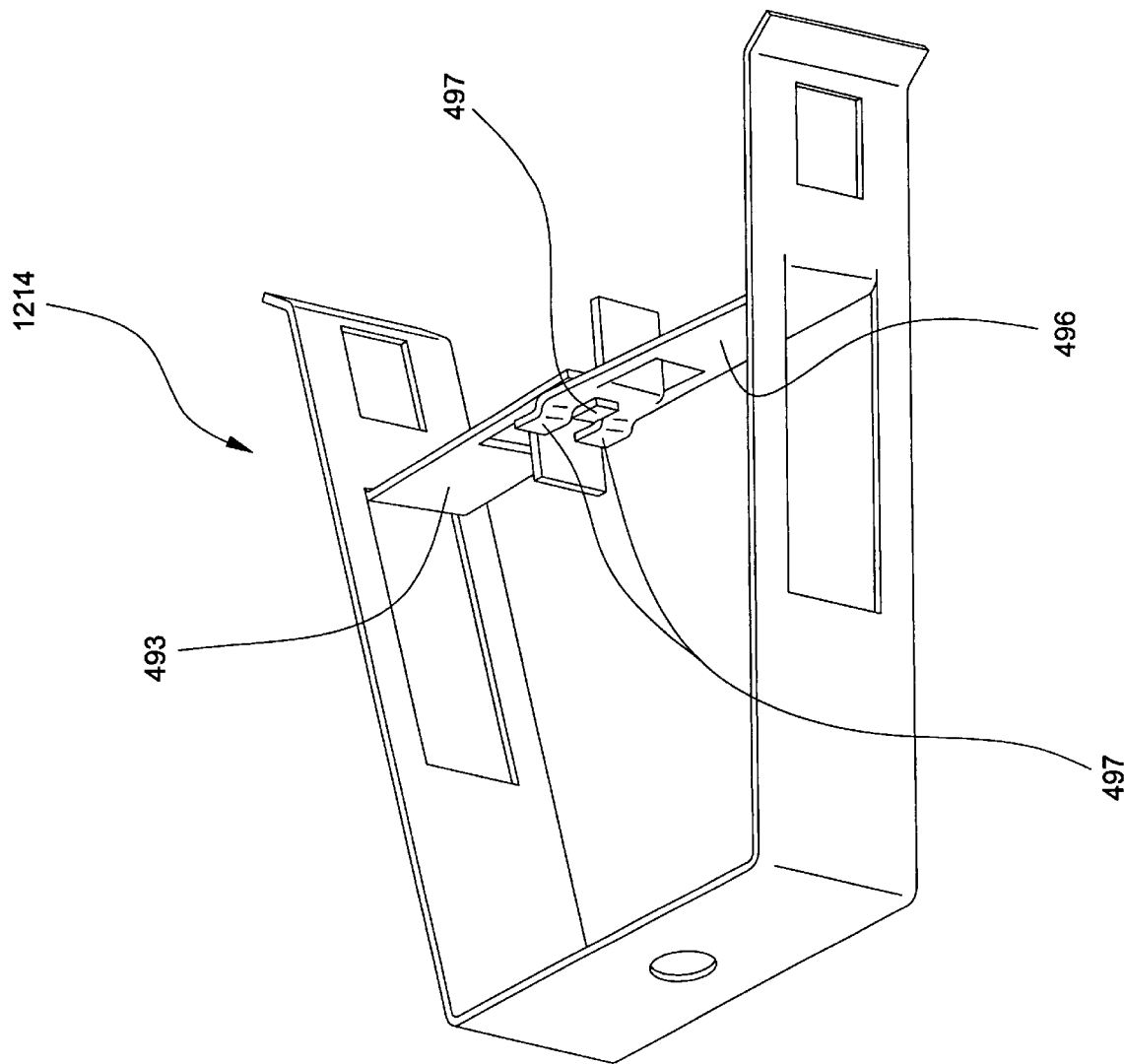
FIG. 53 is a perspective view of the fourth embodiment of the spring clip with a transverse barrier that is used in the needle shield shown in FIGS. 51 and 52 to connect the needle shield to the catheter hub until the sharp distal tip of the introducer needle is locked in the needle shield and a first embodiment of an interlock that prevents defeat of the transverse barrier.

A fourth embodiment of spring clip 1214 having a transverse barrier that connects catheter hub 24 to needle shield 40 until sharp distal tip 32 has been locked in needle shield 40 is shown in FIGS. 51 through 53. This embodiment for spring clip 1214 operates in substantially the same way as the embodiment shown in FIG. 50. The only difference is that the ends of biasing arms 493 are formed with interlocking fingers 497. These fingers 497 facilitate the locking of each biasing arm 493 to one another once sharp distal tip 32 of introducer needle 31 is withdrawn proximally behind biasing arms 493. Preferably, one of biasing arms 493 includes two spaced fingers 497 extending from the end of that biasing arm while the other biasing arm includes one finger 497 extending therefrom. The one finger is adapted to extend through the space created by the two fingers on the first biasing arm and the two fingers extend into the space on either side of the one finger on the second biasing arm. When introducer needle 31 no longer engages biasing arms 493, the ends of biasing arms 493 move apart so that fingers 497 can extend into their respective spaces and overlap with appropriate portions of each other and biasing arms 493. With biasing arms 493 thus locked together via interlocking fingers 497, a transverse barrier is thereby formed by interlocking fingers 497 to prevent unwanted distal movement of introducer needle 31.

Figure 54:
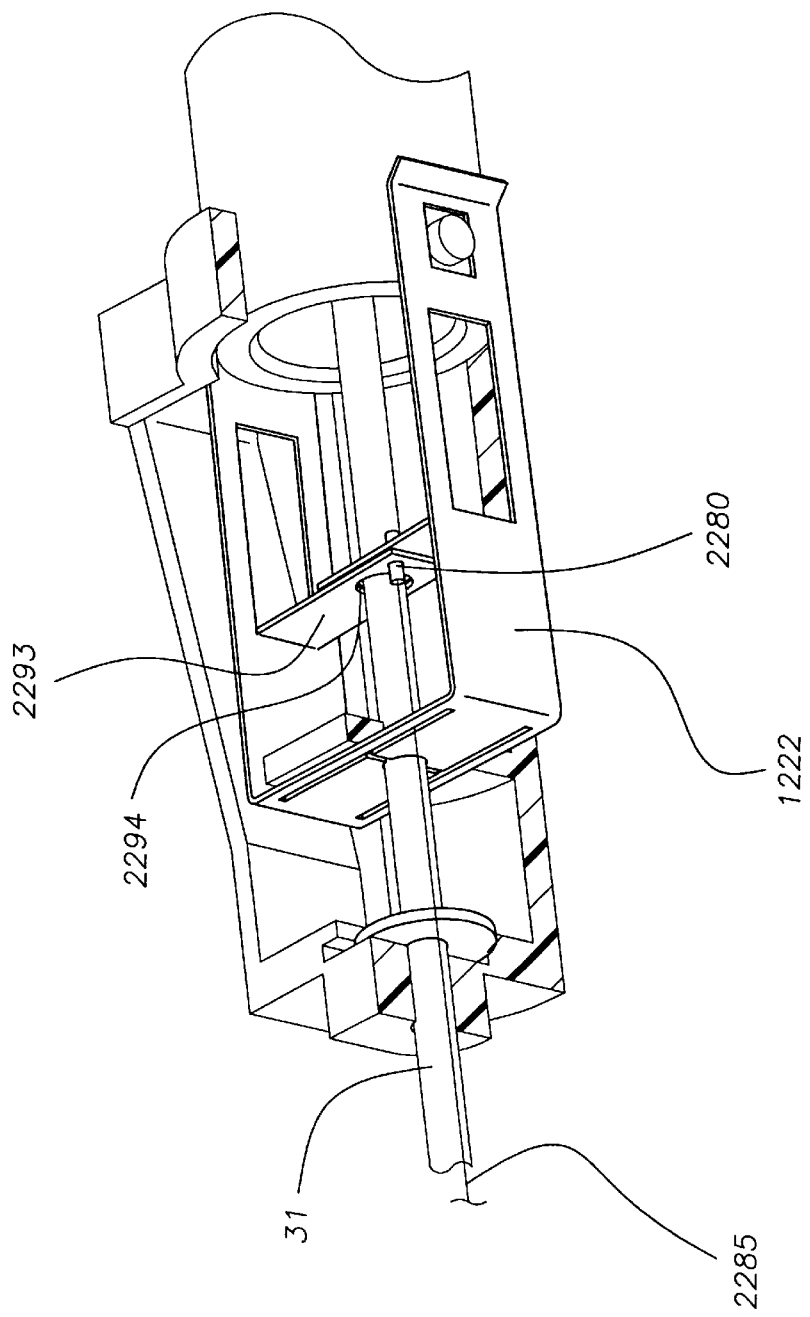
FIG. 54 is a perspective partial cross-sectional view of the needle shield with a first embodiment of the integrated clip lock that connects the needle shield to the catheter hub until the sharp distal tip of the introducer needle is locked in the needle shield and that prevents unwanted distal movement of the introducer needle, a portion of the introducer needle and the proximal portion of the catheter hub with the sharp distal tip of the introducer needle extending from the distal end of the needle shield and the needle shield connected to the catheter hub and a first embodiment of a tethered trigger to disconnect the spring clip from the catheter hub.

A second embodiment of integrated clip lock 1222 that connects needle shield 40 to catheter hub 24 until sharp distal tip 32 of introducer needle 31 is locked in needle shield 40 and that prevents unwanted distal movement of introducer needle 31 is shown in FIG. 54. This embodiment is substantially the same as the embodiment of integrated clip lock 1221 shown in FIGS. 46 through 49 except that in this embodiment a mechanism is provided to minimize drag on introducer needle 31. In this embodiment, holes 2294 are maintained in alignment by a pin 2280 extending through separate holes formed in biasing arms 2293. This pin and hole arrangement maintains holes 2294 in alignment without the edges of holes 2294 contacting the shaft of introducer needle 31. A tether 2285 connects pin 2280 with needle hub 34. Tether 2285 has a length such that when introducer needle 31 has been moved proximally so sharp distal tip 32 of introducer needle 31 is proximal of biasing arms 2293, tether 2285 pulls pin 2280 proximally out of biasing arms 2293. At that point, biasing arms 2293 can move outwardly out of engagement with catheter hub 24.

Figure 55:
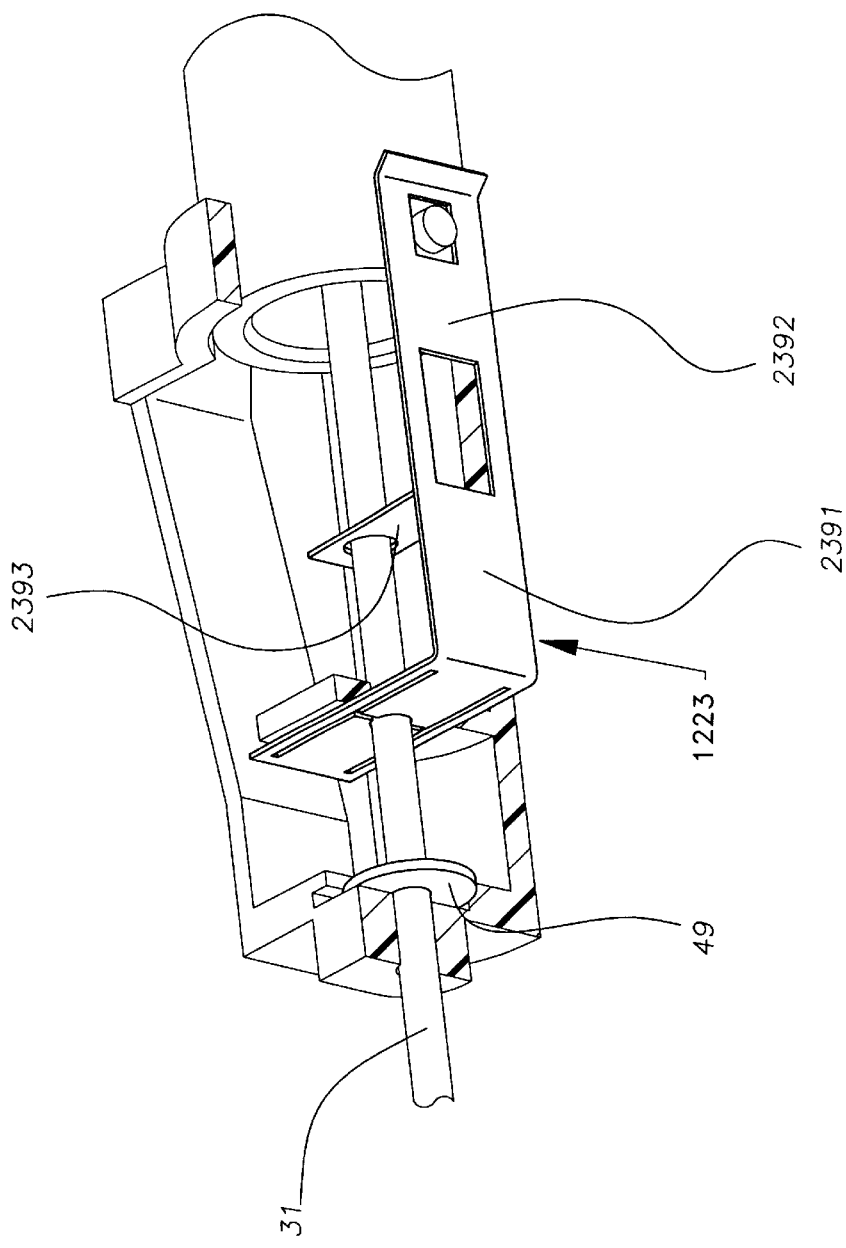
FIG. 55 is a perspective partial cross-sectional view of the needle shield with the second embodiment of the integrated clip lock that connects the needle shield to the catheter hub until the sharp distal tip of the introducer needle is locked in the needle shield and that prevents unwanted distal movement of the introducer needle, a portion of the introducer needle and the proximal portion of the catheter hub with the sharp distal tip of the introducer needle extending from the distal end of the needle shield and the needle shield connected to the catheter hub.
Figure 56:
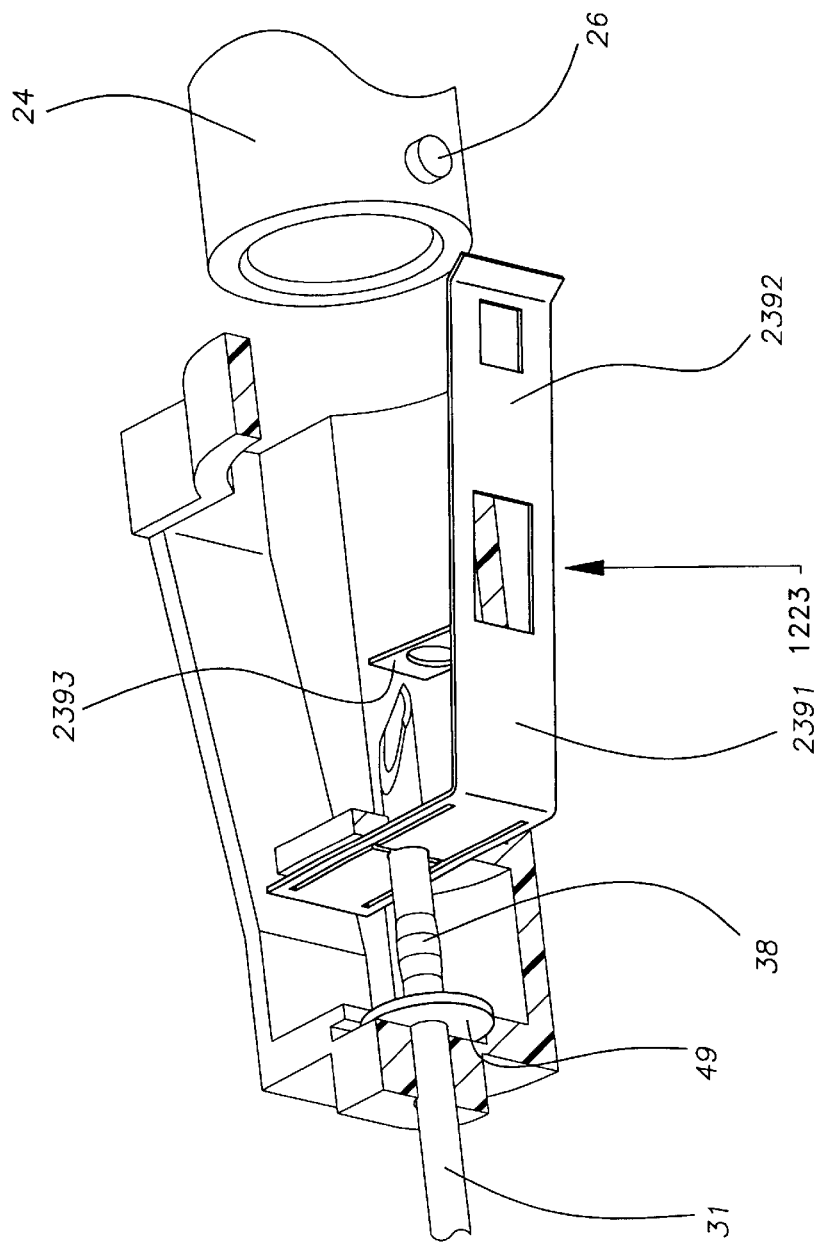
FIG. 56 is a perspective partial cross-sectional view of the needle shield with the second embodiment of the integrated clip lock that connects the needle shield to the catheter hub until the sharp distal tip of the introducer needle is locked in the needle shield and that prevents unwanted distal movement of the introducer needle, the distal portion of the introducer needle and the proximal portion of the catheter hub with the sharp distal tip of the introducer needle locked in the needle shield and the needle shield disconnected from the catheter hub.
Figure 57:
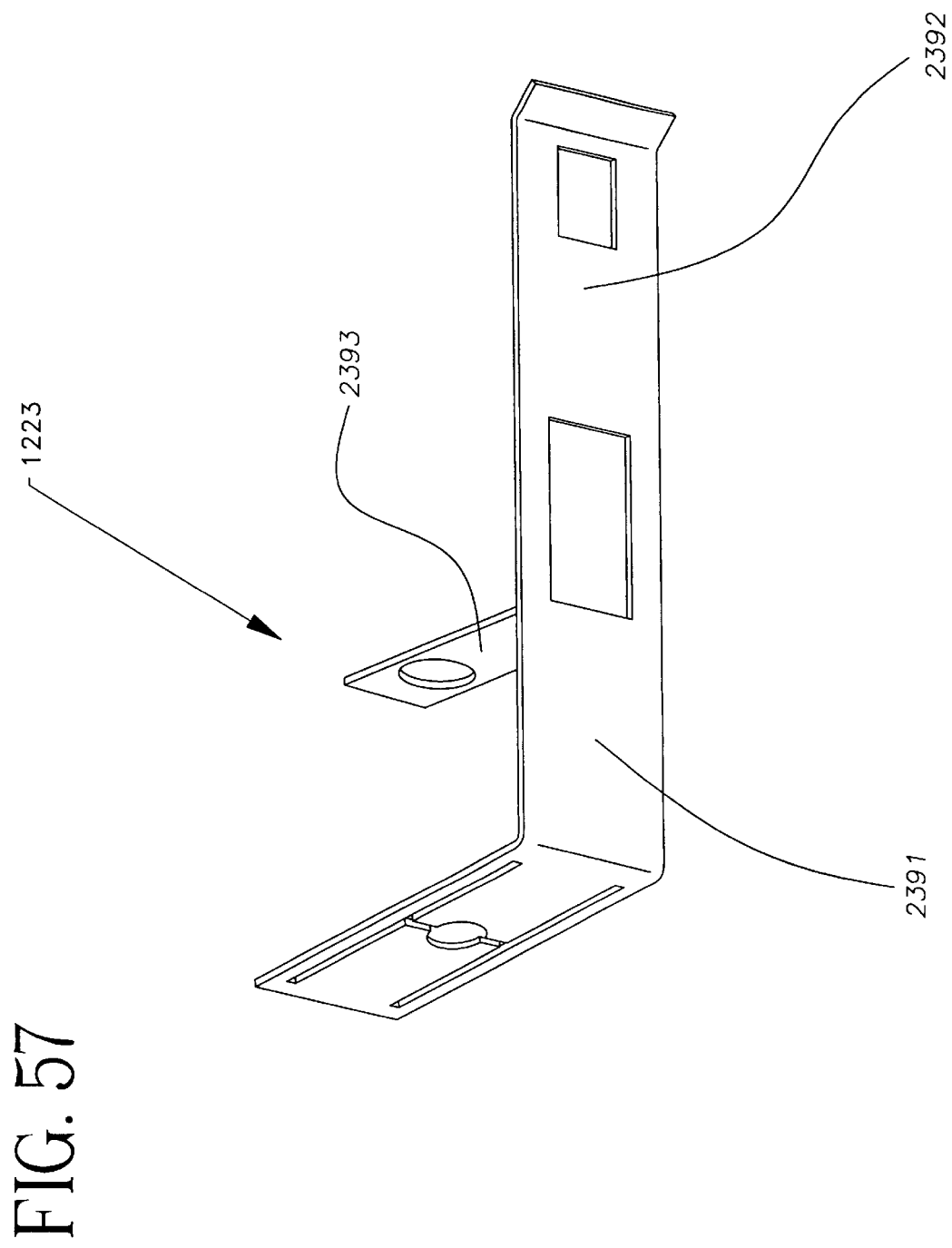
FIG. 57 is a perspective view of the second embodiment of the integrated clip lock shown in FIGS. 55 and 56 to connect the needle shield to the catheter hub until the sharp distal tip of the introducer needle is locked in the needle shield and to prevent unwanted distal movement of the introducer needle.

A third embodiment of an integrated clip lock 1223 is shown in FIGS. 55 through 57. In this embodiment of integrated clip lock 1223, the resilient spring arm 2391 is formed with only one leg 2392 such that it would have a substantially L-shaped configuration. Preferably spring arm 2391 is oriented in housing 41 such that the base is oriented toward the proximal portion of housing 41 and leg 2392 extends generally parallel to the longitudinal axis of introducer needle 31. With only one leg 2392, only one biasing arm 2393 needs to be used. Biasing arm 2393 defines a hole therein through which introducer needle 31 extends. This embodiment for spring arm 2391 operates in a similar manner to the embodiment shown in FIGS. 46 through 49 and the distal portion of leg 2392 can have the same configuration of legs 2192. When introducer needle 31 extends through the hole in biasing arm 2393, leg 2392 is pulled inwardly toward and engages catheter hub 24 as long as sharp distal tip 32 of introducer needle 31 is distal of biasing arm 2393. Once introducer needle 31 is pulled proximal of biasing arms 2393, leg 2392 is free to return to its activated, unbiased, non-clipped position. Thus spring arm 2391 can flex into and out of engagement with catheter hub 24.

Figure 58:
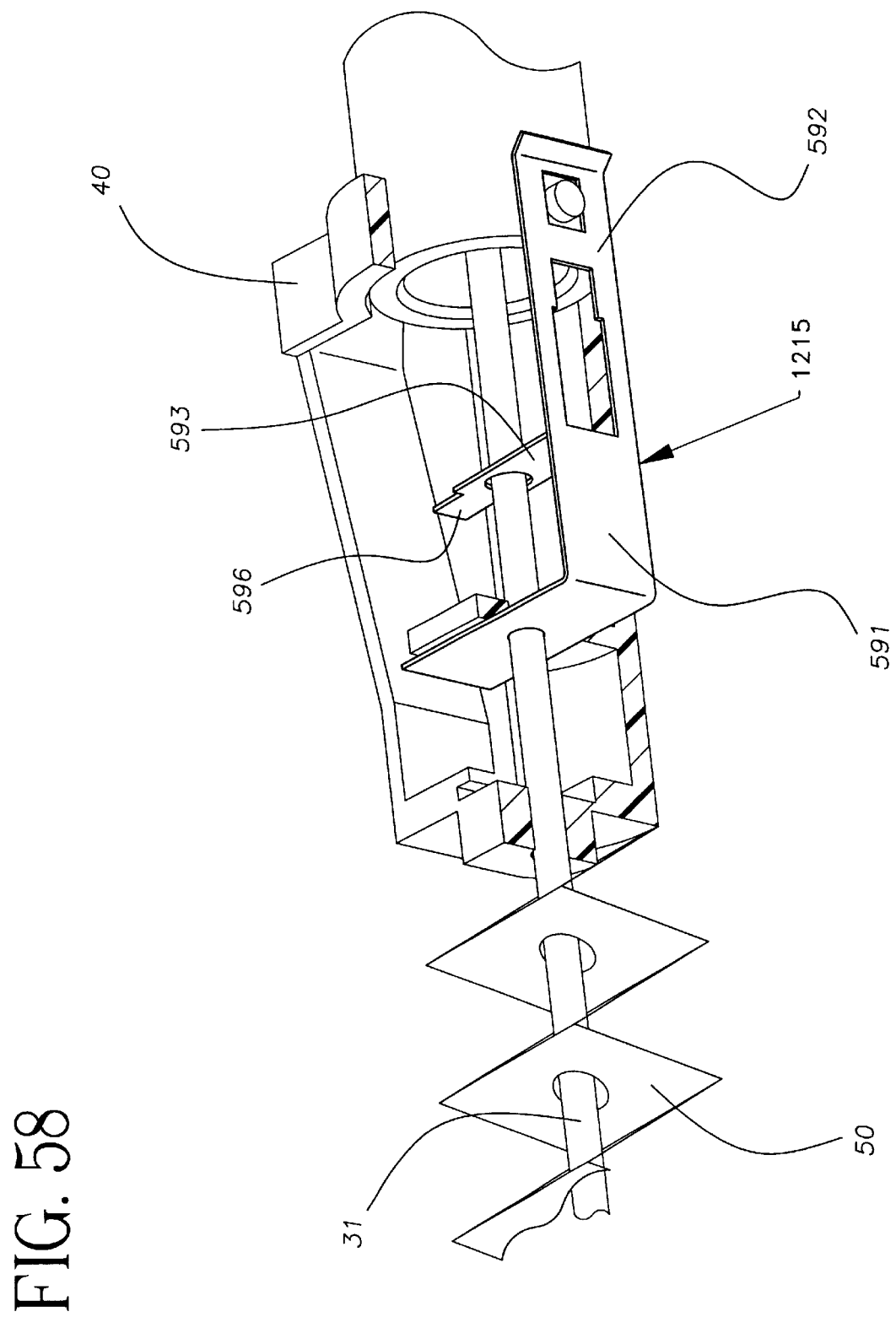
FIG. 58 is a perspective partial cross-sectional view of the needle shield with a fifth embodiment of a spring clip with a transverse barrier that connects the needle shield to the catheter hub until the sharp distal tip of the introducer needle is locked in the needle shield, a portion of the introducer needle, a portion of the tether and the proximal portion of the catheter hub with the sharp distal tip of the introducer needle extending from the distal end of the needle shield and the needle shield connected to the catheter hub.

A fifth embodiment of spring clip 1215 with a transverse barrier 596 is shown in FIG. 58. In this embodiment, the spring arm 591 is formed with only one leg 592 such that it has a substantially L-shaped configuration. With only one leg 592, only a single biasing arm 593 is used. This single biasing arm 593 is formed with an extended portion that acts as a transverse barrier 596 to prevent subsequent distal movement of introducer needle 31 once sharp distal tip 32 is withdrawn proximally of biasing arms 593. This embodiment of spring clip 1215 operates in substantially the same manner as the spring clip portion of integrated clip lock 1223 shown in FIGS. 55–57.

Figure 59:
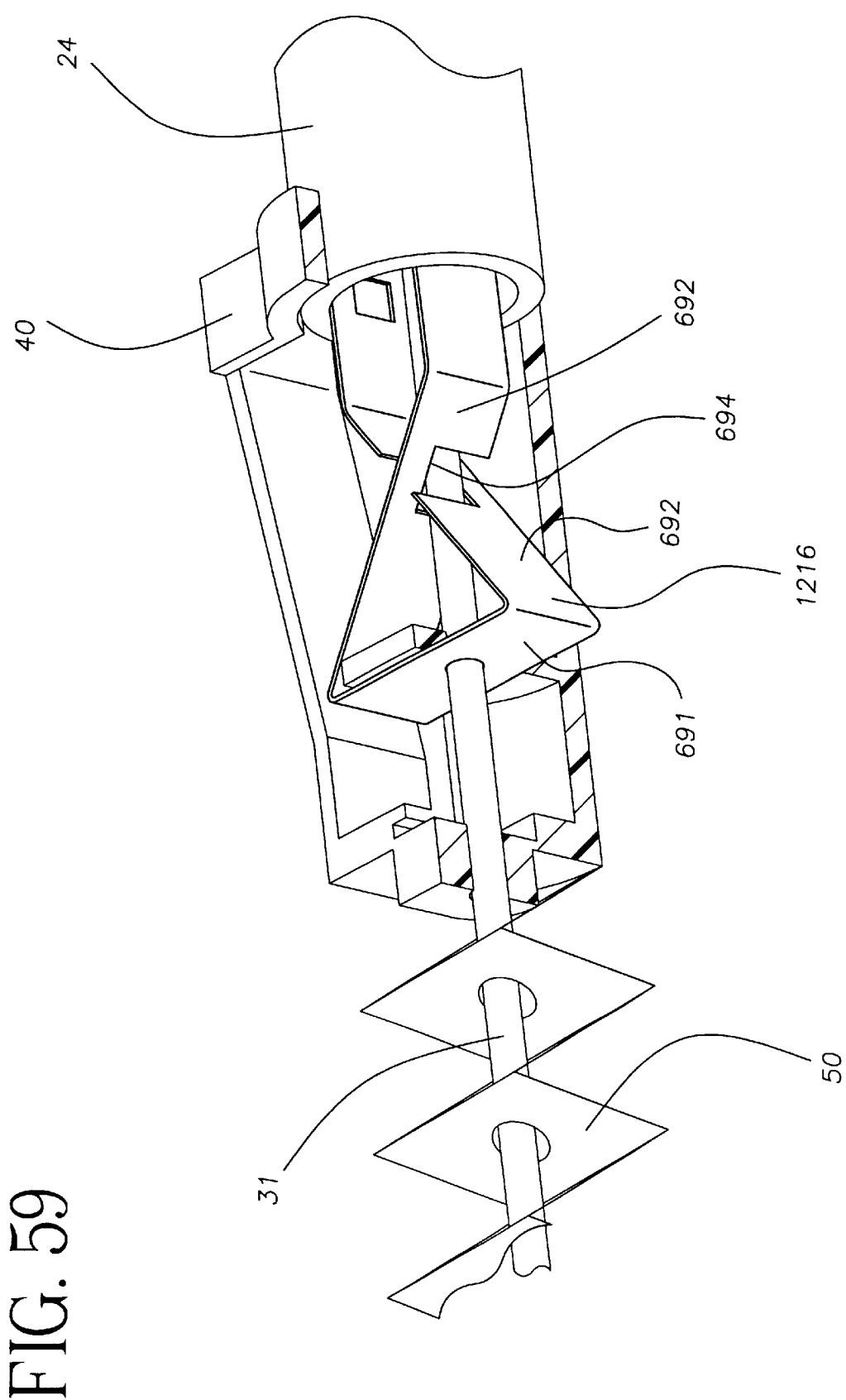
FIG. 59 is a perspective partial cross-sectional view of the needle shield with a sixth embodiment of the spring clip with a transverse barrier that connects the needle shield to the catheter hub until the sharp distal tip of the introducer needle is locked in the needle shield, a portion of the introducer needle, a portion of the tether and the proximal portion of the catheter hub with the sharp distal tip of the introducer needle extending from the distal end of in the needle shield with the needle shield connected to the catheter hub.
Figure 60:
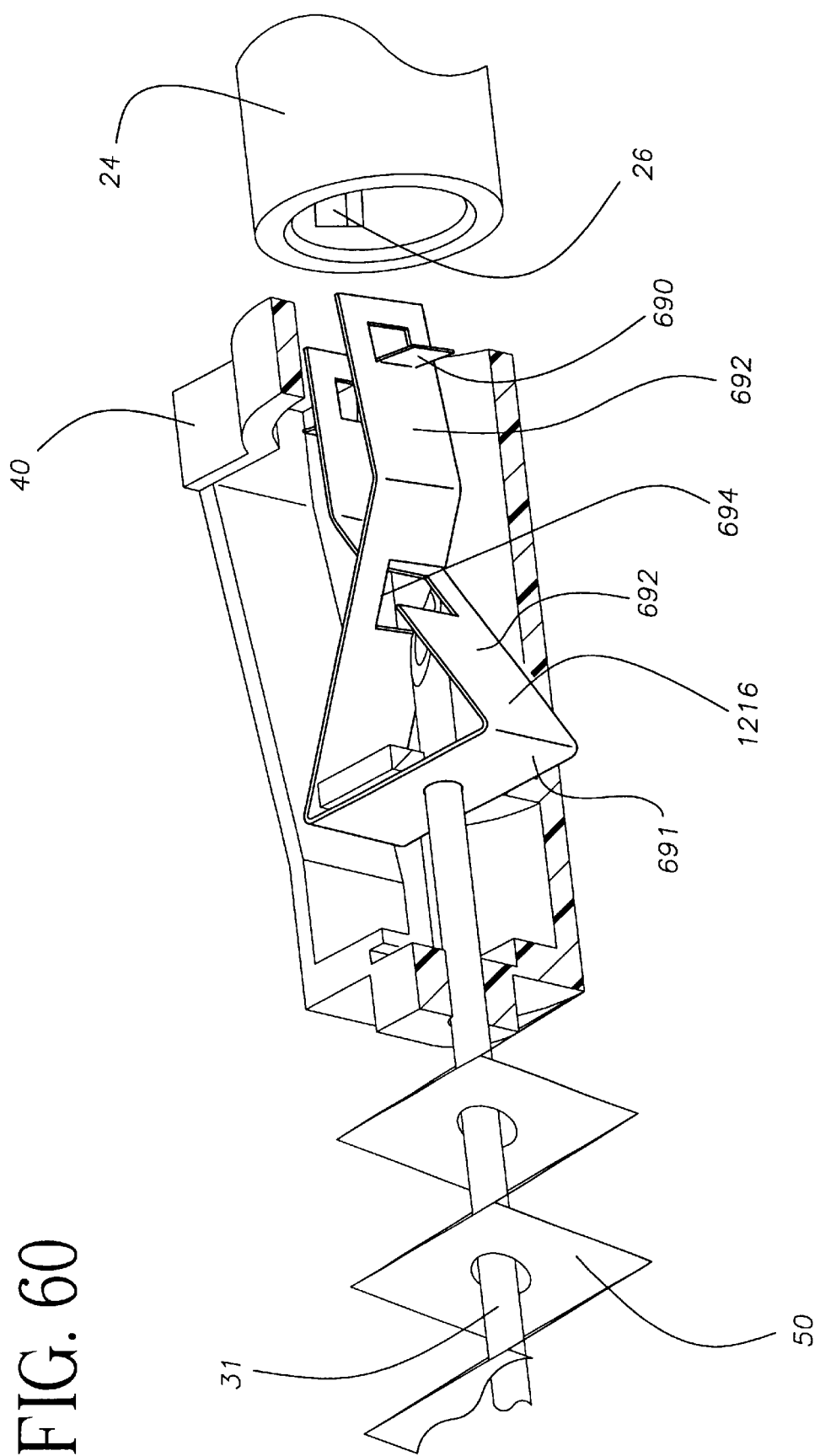
FIG. 60 is a perspective partial cross-sectional view of the needle shield with the sixth embodiment of the spring clip with a transverse barrier that connects the needle shield to the catheter hub until the sharp distal tip of the introducer needle is locked in the needle shield, the distal portion of the introducer needle, the distal portion of the tether and the proximal portion of the catheter hub with the sharp distal tip of the introducer needle locked in the needle shield and the needle shield disconnected from the catheter hub.
Figure 61:
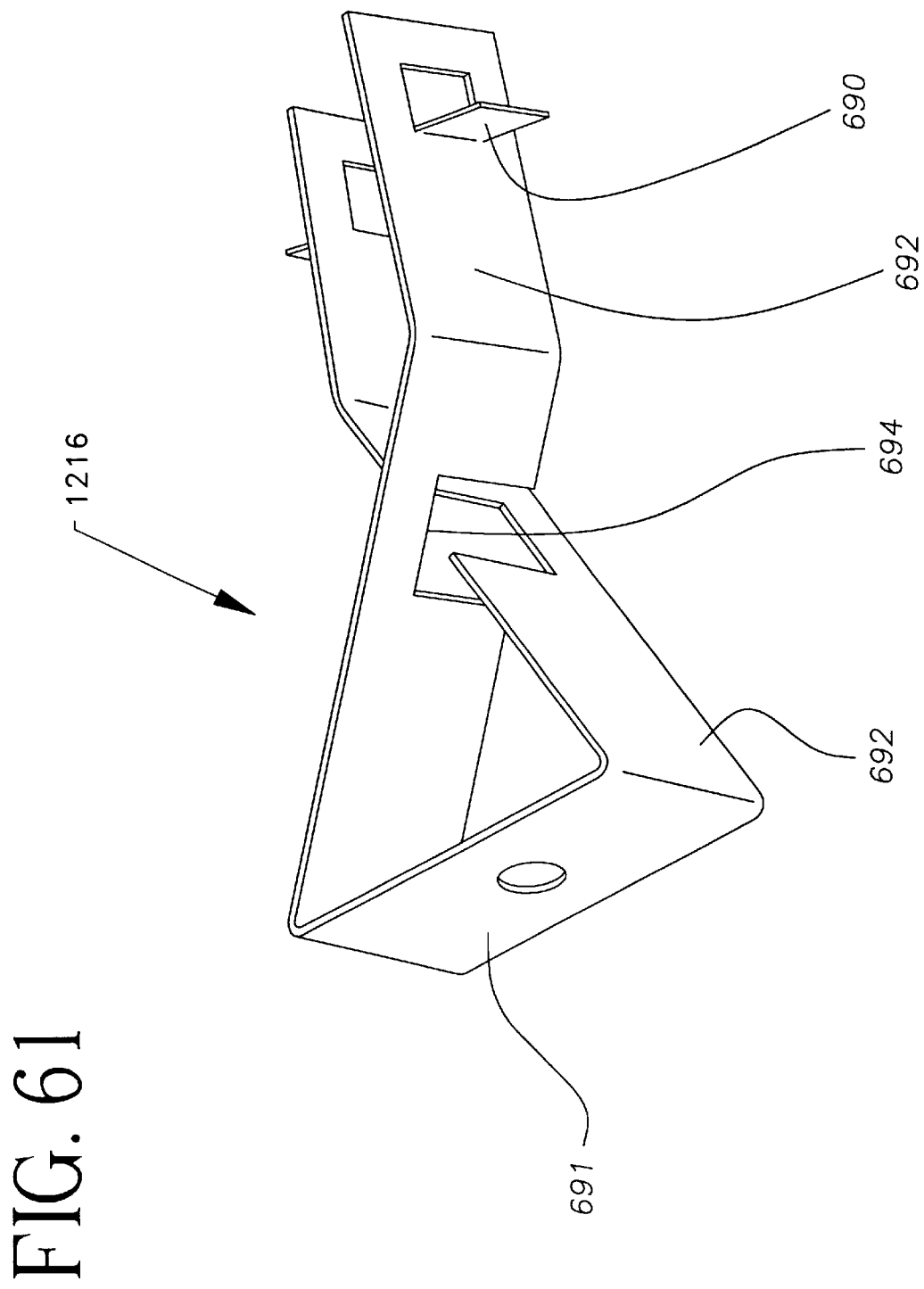
FIG. 61 is a perspective view of the sixth embodiment of the spring clip with a transverse barrier shown in FIGS. 59 and 60 that connects the needle shield to the catheter hub until the sharp distal tip of the introducer needle is locked in the needle shield.

A sixth embodiment of spring clip 1216 having a transverse barrier is shown in FIGS. 59 through 61. In this embodiment, spring clip 1216 is formed with a pair of crossed legs 692 to provide a substantially X-shaped configuration. Spring clip 1216 is preferably oriented in housing 41 such that base 691 is oriented toward the proximal portion of housing 41. Each leg 692 defines a cut-out portion or opening 694 therein. These cut-out portions 694 allow introducer needle 31 to extend therethrough and provide a mechanism to allow legs 692 to cross each other. The distal portion of each leg 692 is biased inwardly and defines a peg 690 thereon. Pegs 690 are adapted to engage a detents 26 formed on the inside of catheter hub 24. When introducer needle 31 extends past the distal end of needle shield 40 into catheter hub 24, introducer needle 31 also extends through cut-out portions 694. This pushes legs 692 outwardly toward catheter hub 24 so pegs 690 engage detents 26. This maintains needle shield 40 connected to catheter hub 24. Once introducer needle 31 is pulled proximal of cut-out portions 694, legs 692 are free to return to their inward unbiased, non-clipped position where pegs 690 no longer engage detent 26. Thus spring clip 1216 can flex into and out of engagement with catheter hub 24.

A tether 50 could be used in conjunction with spring clip 1216 to prevent unwanted proximal movement of introducer needle 31. Alternatively, the proximal wall 691 of spring clip 1216 could be formed as the retention plate shown in FIG. 37A. Thus, introducer needle 31 could be formed with enlarged diameter portion 38 and would cooperate with the retention plate in the manner previously discussed to prevent unwanted distal movement of introducer needle 31.

Figure 62:
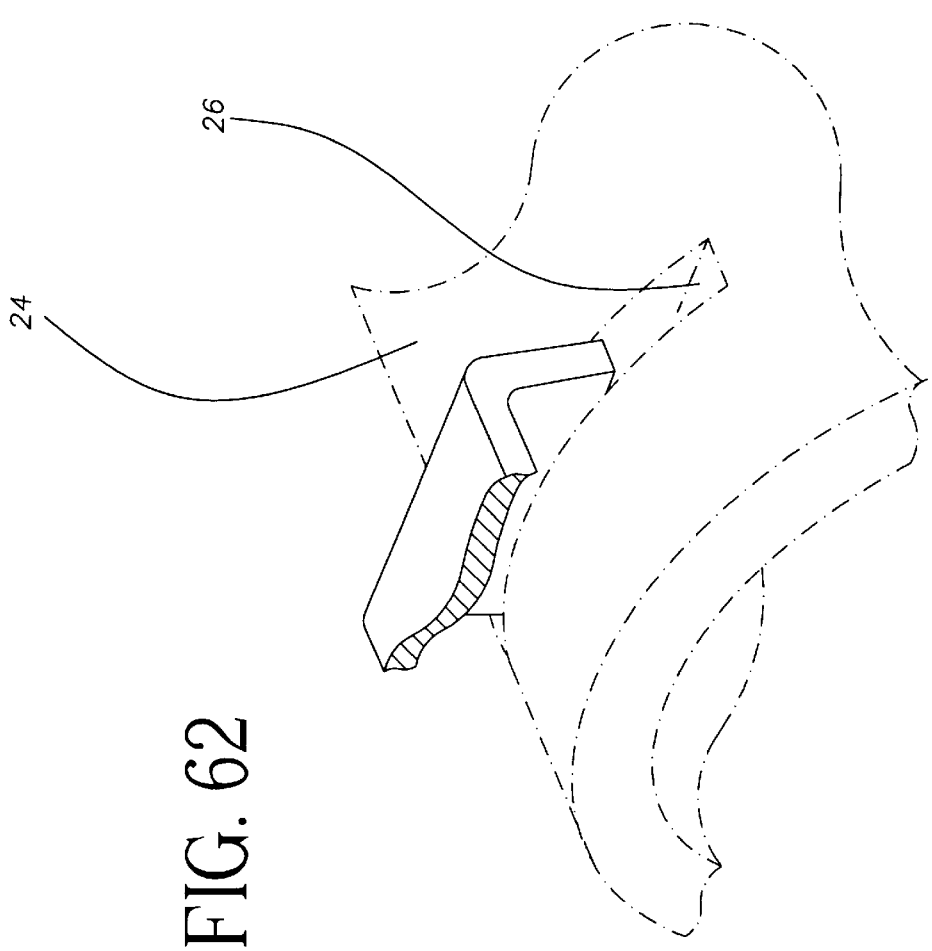
FIG. 62 is a schematic view of a portion of the clip arm showing an alternative embodiment for the engagement mechanism between the needle shield and the catheter hub.
Figure 63:
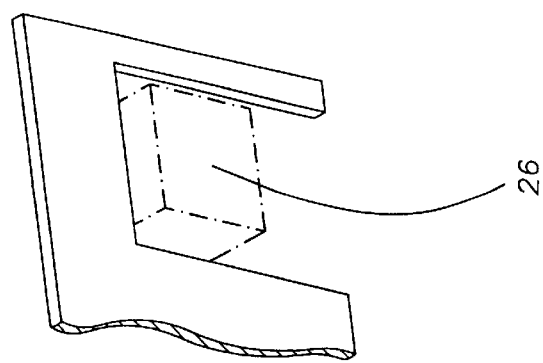
FIG. 63 is a schematic view of a portion of the clip arm showing another alternative embodiment for the engagement mechanism between the needle shield and the catheter hub.
Figure 65:
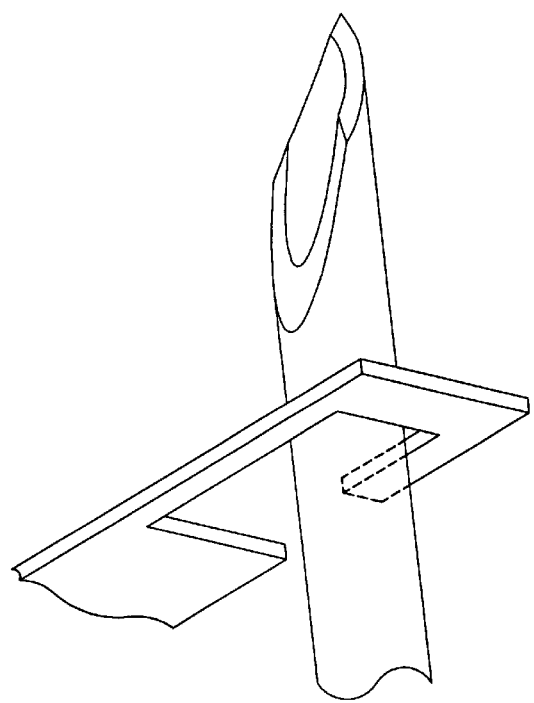
FIG. 65 is a perspective view of a portion of the biasing arm showing another alternative embodiment for the engagement mechanism between the needle and the biasing arm.
Figure 64:
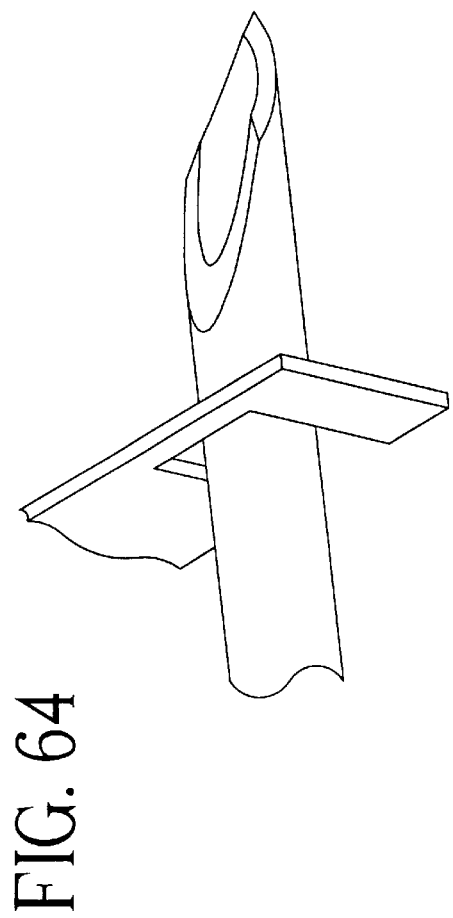
FIG. 64 is a perspective view of a portion of the biasing arm showing an alternative embodiment for the engagement mechanism between the needle and the biasing arm.
Figure 66:
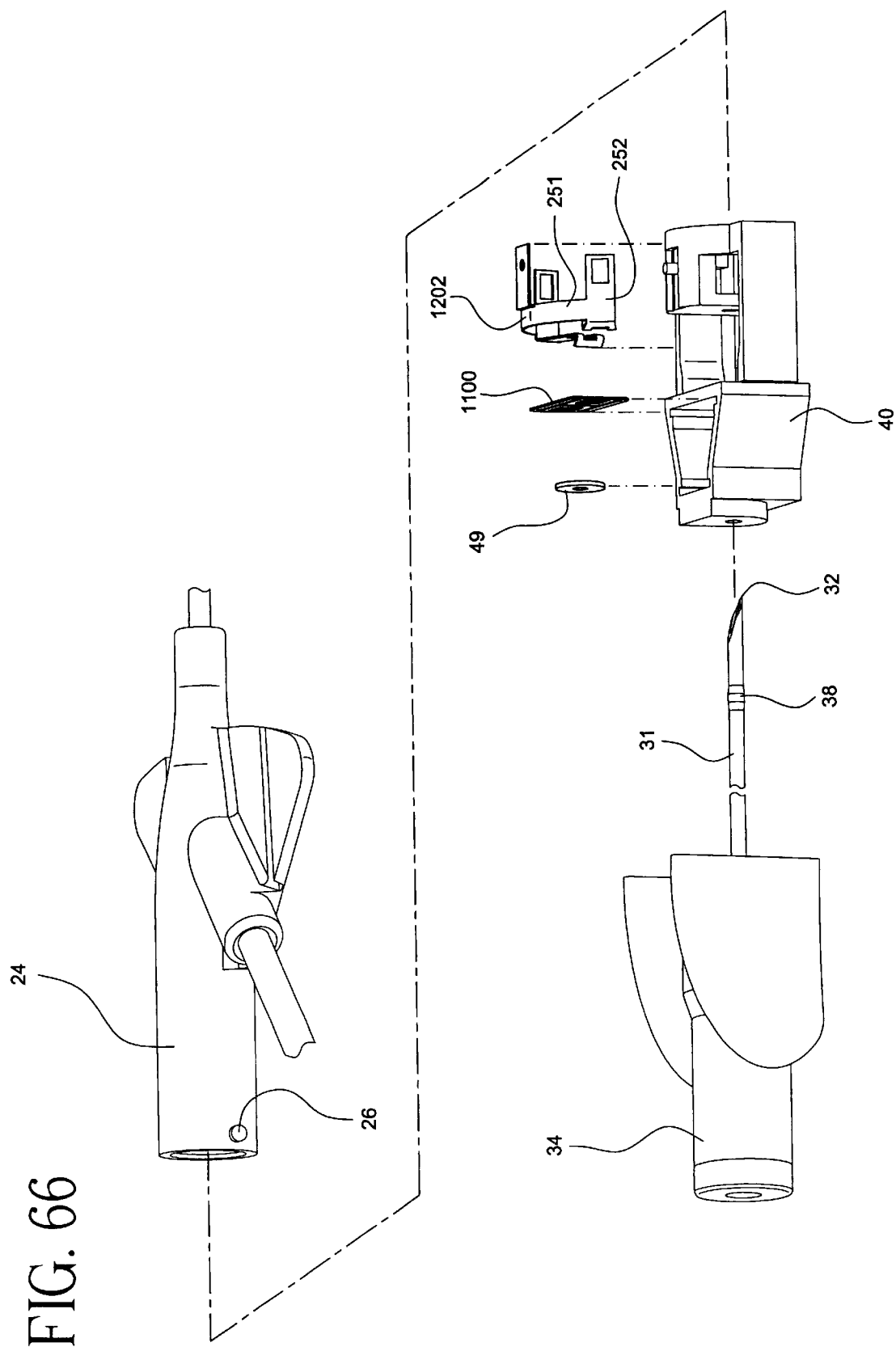
FIG. 66 is an exploded perspective view of an integrated catheter, introducer needle and needle shield with the eleventh embodiment of the lock that prevents unwanted distal movement of the introducer needle and the second embodiment of the spring clip that connects the needle shield to the catheter hub until the sharp distal tip of the introducer needle is shielded in the needle shield.
Figure 67:
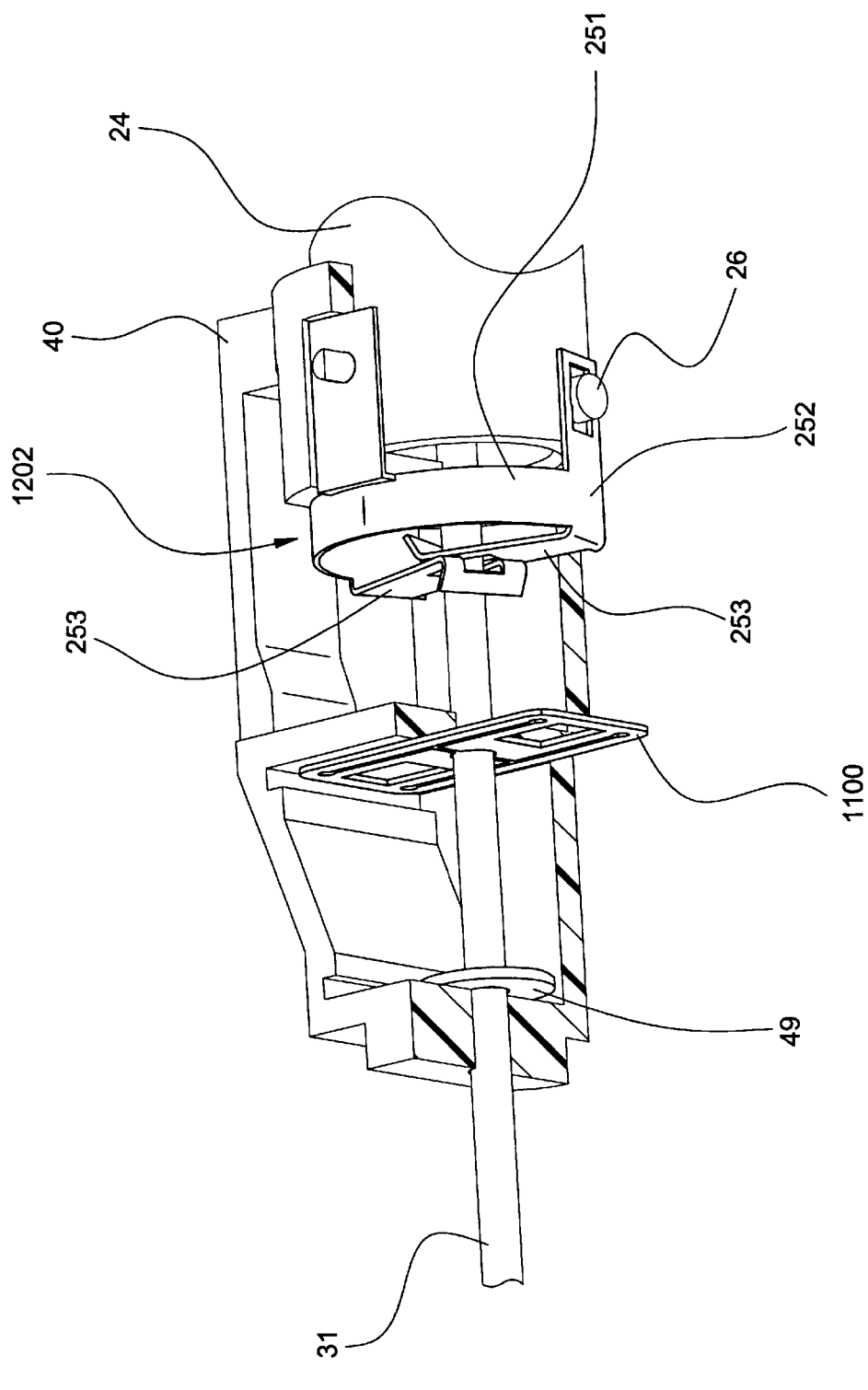
FIG. 67 is a perspective partial cross-sectional view of the needle shield with the eleventh embodiment of the lock that prevents unwanted distal movement of the introducer needle and the second embodiment of the spring clip that connects the needle shield to the catheter hub until the sharp distal tip of the introducer needle is shielded in the needle shield, a portion of the introducer needle and the proximal portion of the catheter hub with the sharp distal tip of the introducer needle extending from the distal end of the needle shield and the needle shield connected to the catheter hub.
Figure 68:
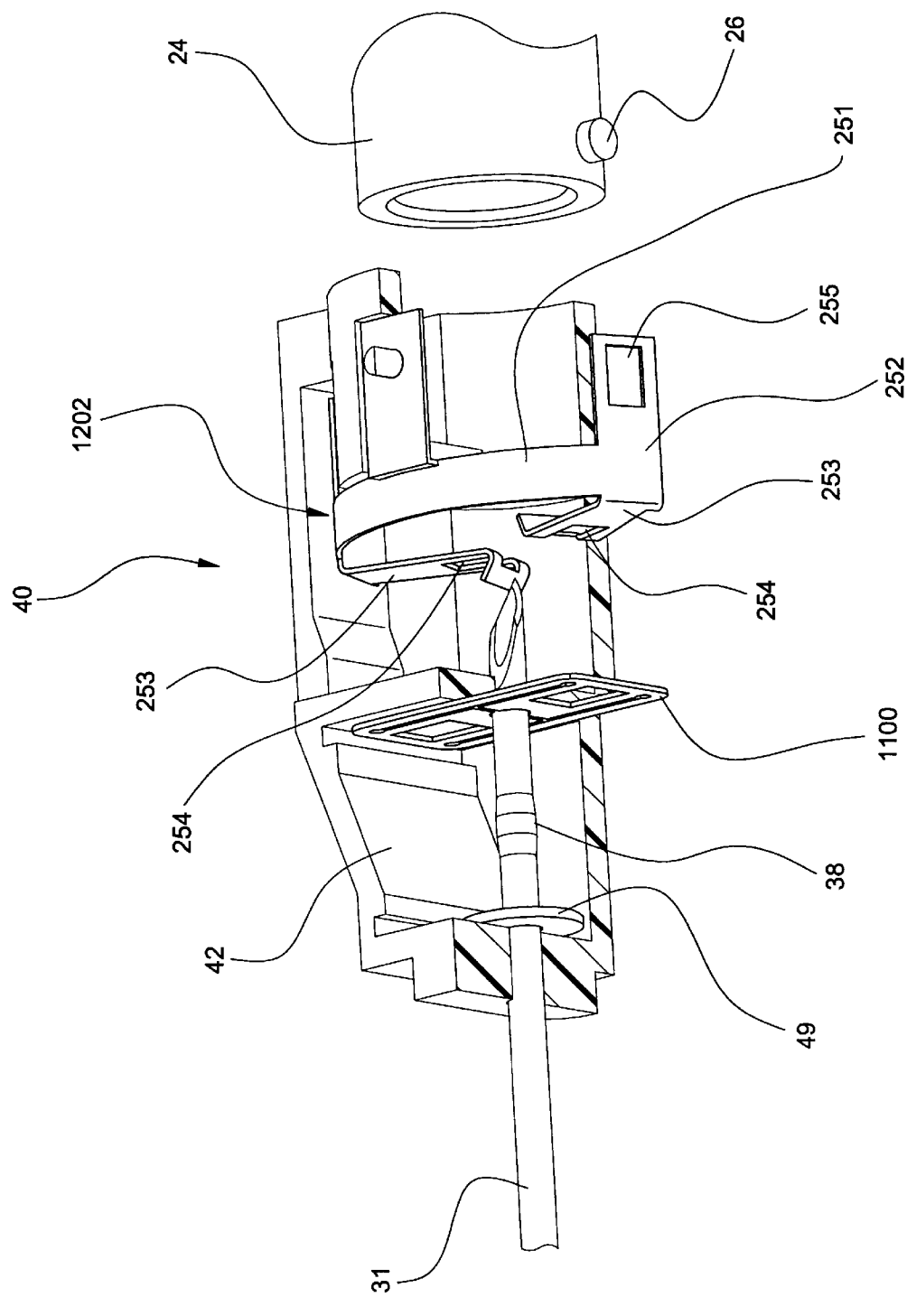
FIG. 68 is a perspective partial cross-sectional view of the needle shield with the eleventh embodiment of the lock that prevents unwanted distal movement of the introducer needle and the second embodiment of the spring clip that connects the needle shield to the catheter hub until the sharp distal tip of the introducer needle is shielded in the needle shield, the distal portion of the introducer needle and the proximal portion of the catheter hub with the sharp distal tip of the introducer needle locked in the needle shield and the needle shield disconnected from the catheter hub.
Figure 69:
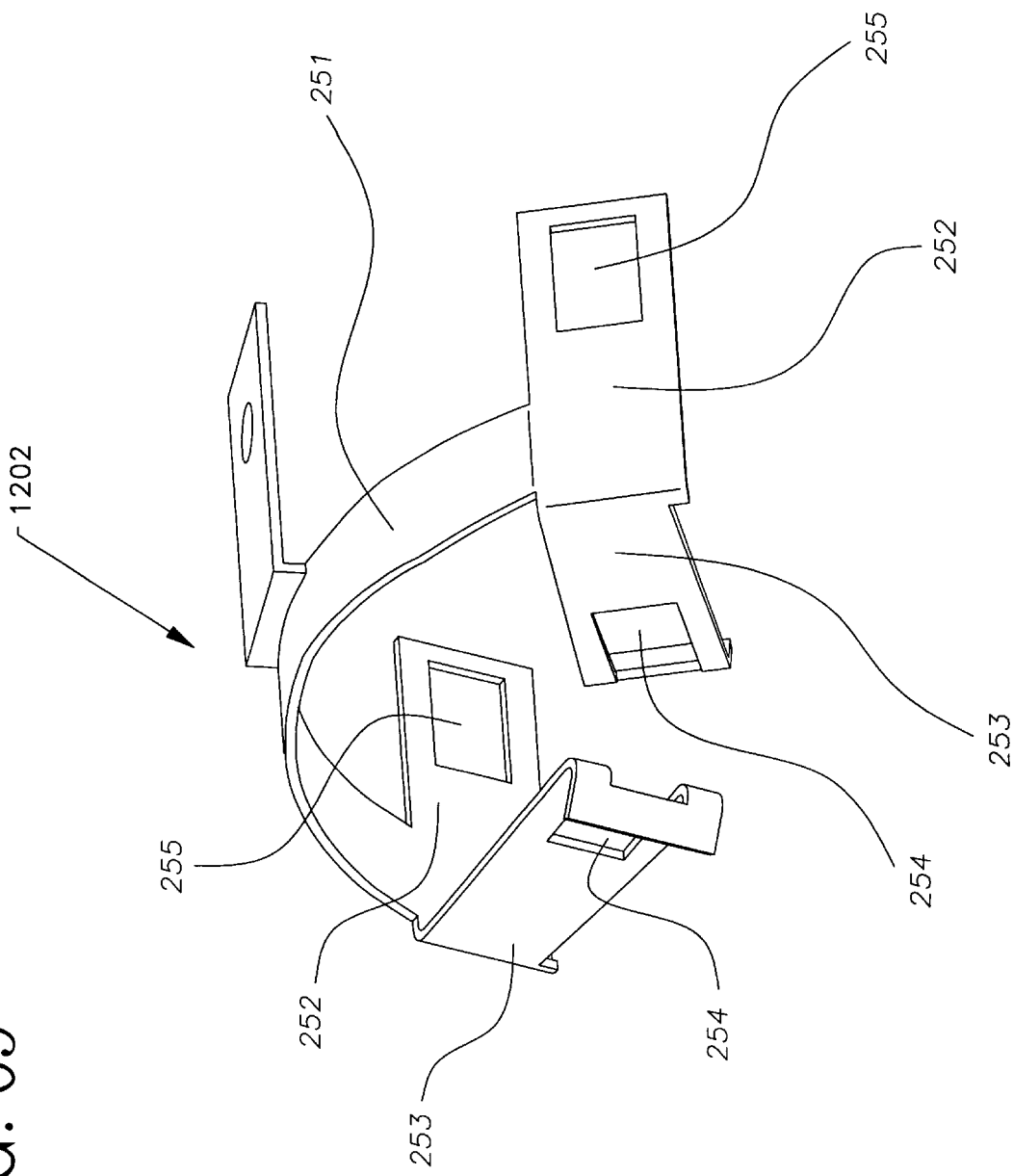
FIG. 69 is a perspective view of the second embodiment of the spring clip shown in FIGS. 66 through 68 that connects the needle shield to the catheter hub until the sharp distal tip of the introducer needle is shielded in the needle shield.
Figure 70:
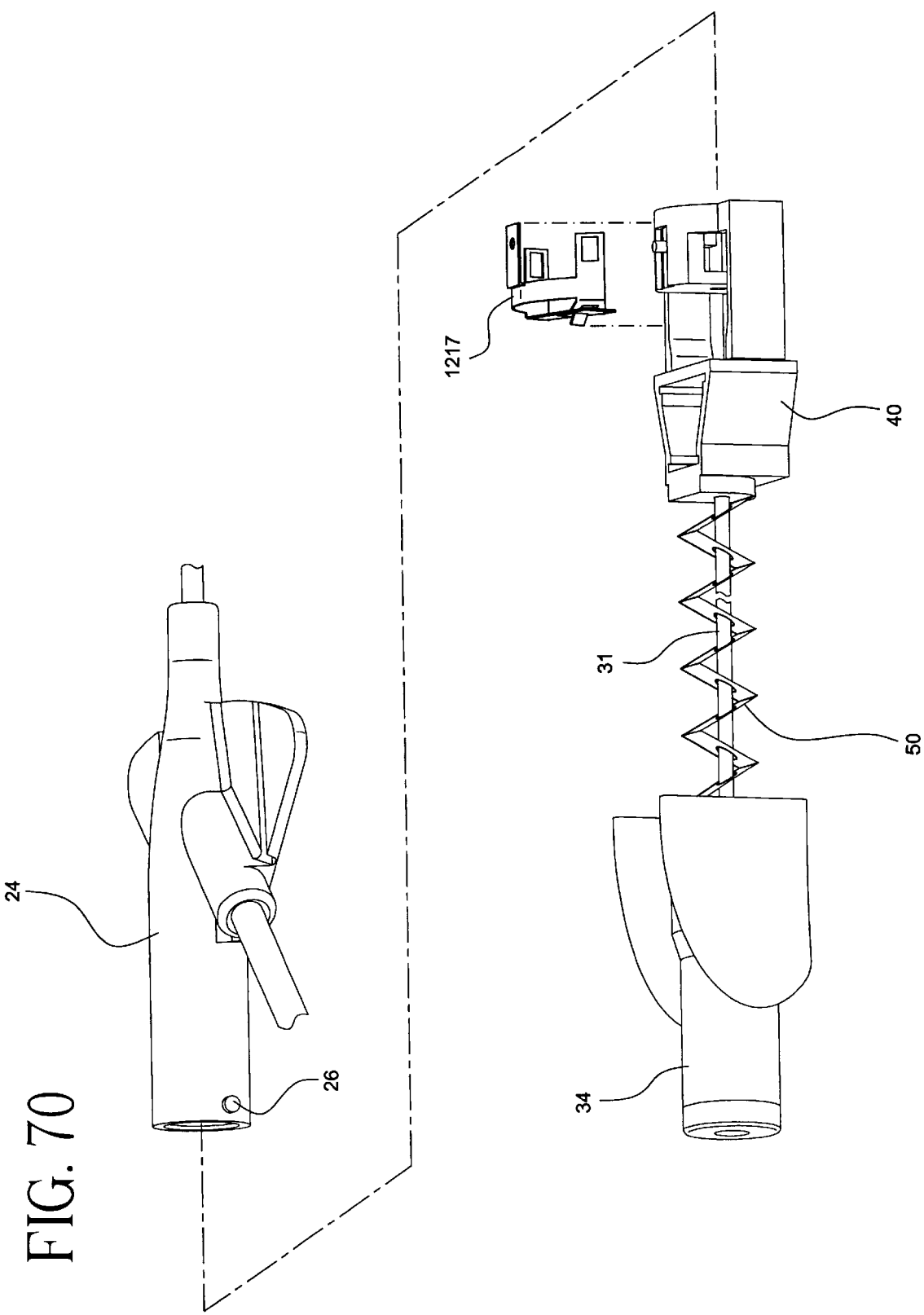
FIG. 70 is an exploded perspective view of an integrated catheter, introducer needle and the needle shield with a seventh embodiment of the spring clip with a transverse barrier that connects the needle shield to the catheter hub until the sharp distal tip of the introducer needle is shielded by the needle shield and a tether.
Figure 71:
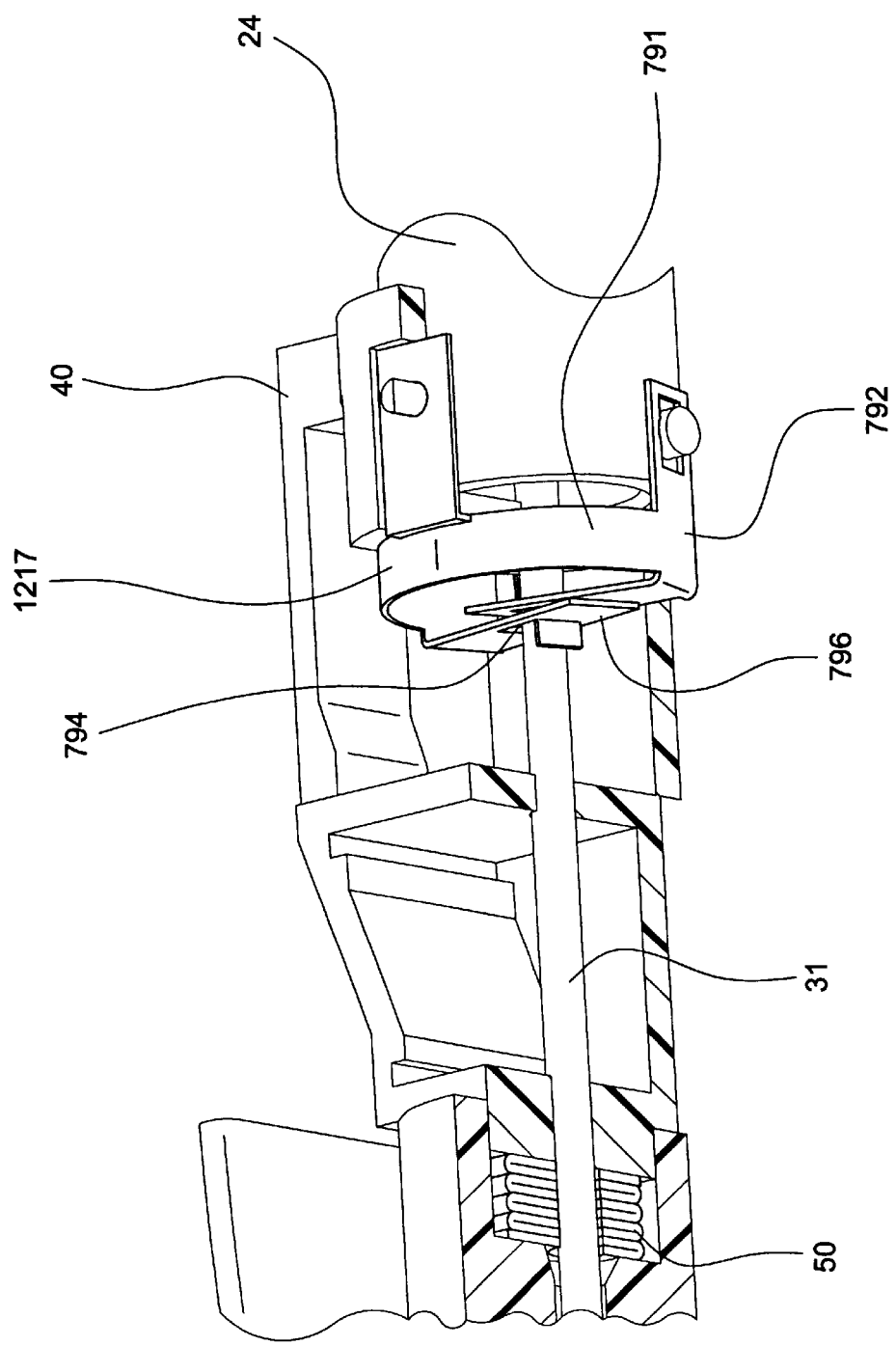
FIG. 71 is a perspective partial cross-sectional view of the needle shield with the seventh embodiment of the spring clip with a transverse barrier that connects the needle shield to the catheter hub until the sharp distal tip of the introducer needle is shielded by the needle shield, a portion of the introducer needle, the tether and the proximal portion of the catheter hub with the sharp distal tip of the introducer needle extending from the distal end of the needle shield and the needle shield connected to the catheter hub.
Figure 72:
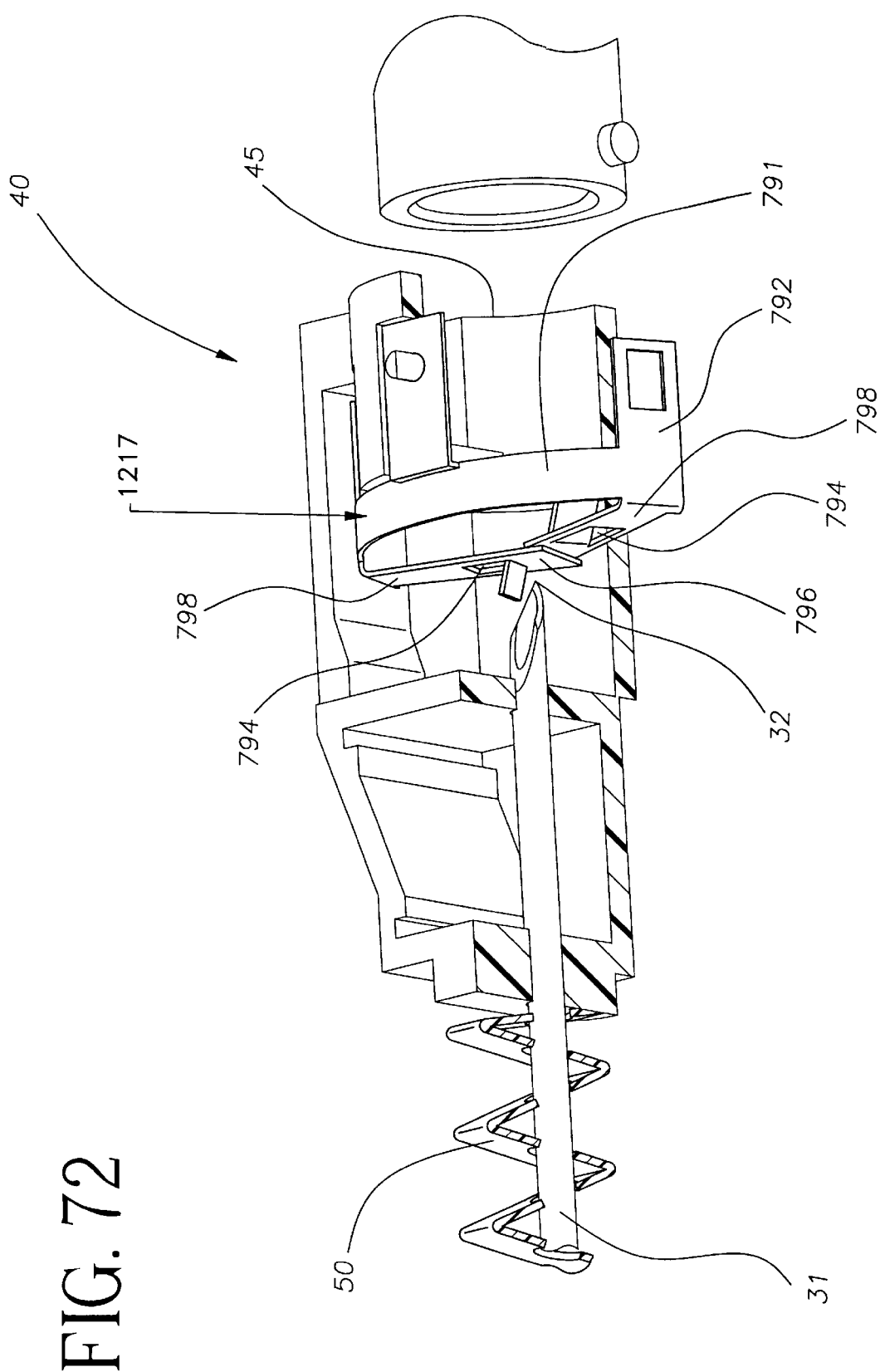
FIG. 72 is a perspective partial cross-sectional view of the needle shield with the seventh embodiment of the spring clip with a transverse barrier that connects the needle shield to the catheter hub until the sharp distal tip of the introducer needle is shielded by the needle shield, the distal portion of the introducer needle, the distal portion of the tether and the proximal portion of the catheter hub with the sharp distal tip of the introducer needle locked in the needle shield and the needle shield disconnected from the catheter hub.
Figure 73:
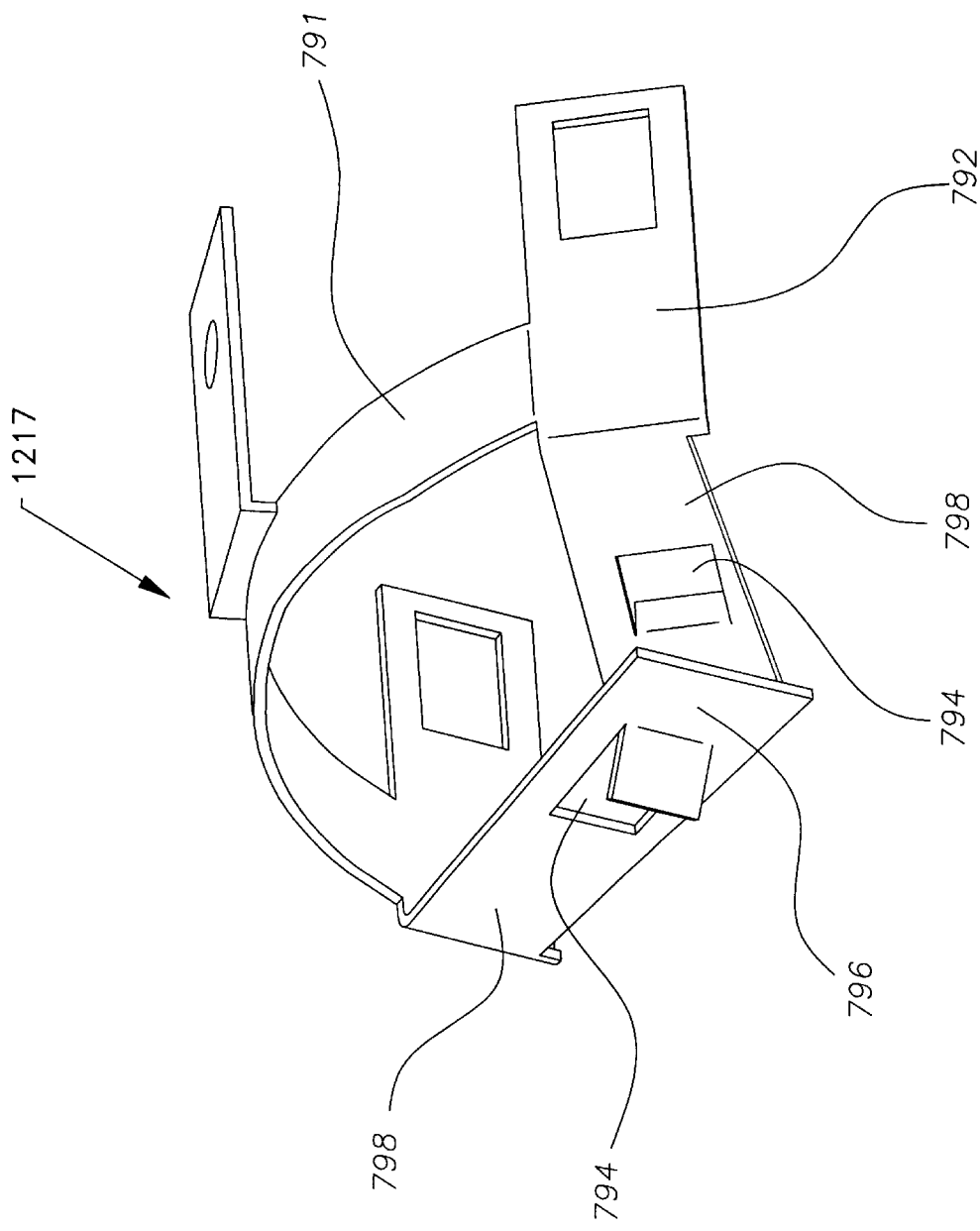
FIG. 73 is a perspective view of the seventh embodiment of the spring clip with a transverse barrier shown in FIGS. 70 through 72, that connects the needle shield to the catheter hub.

As discussed above, the configuration of the portion of the spring clip in all of the previous embodiments that engage catheter hub 24, as well as detent 26, could have a wide variety of configurations. For example, detent 26 could be in the form of a slot and a radially inwardly extending finger could be disposed on the portion of the spring clip that engages detent 26. See FIG. 62. Alternatively, detent 26 could be in the form of a post, which could be rectangular or have some other geometric shape, and holes, which could be open ended, could be formed on the portion of the spring clip that engages detent 26. See FIG. 63. In addition, the configuration of the holes in the biasing arms that engage the introducer needle could be open ended such as shown in FIGS. 64 and 65.

A second embodiment for spring clip 1202 that connects needle shield 40 to catheter hub 24 is shown in FIGS. 66 through 69. In this embodiment, spring clip 1202 is formed as a separate piece from retention plate 1100 shown in FIG. 37. Spring clip 1202 is formed with a spring arm 251 and a pair of outwardly biased clip arms 252. Spring arm 251 is oriented in housing 41 such that the legs of the U straddle the longitudinal axis of introducer needle 31. Preferably the closed portion of the U is oriented toward the top of housing 41. However, it is to be understood that spring arm 251 could be in any rotational orientation in the same plane as a circle concentric to the longitudinal axis of introducer needle 31. Each clip arm 252 extends generally parallel to the longitudinal axis of introducer needle 31. Of course it is to be understood that only one clip arm 252 need be used. A biasing arm 253 extends from each end of spring arm 251. Biasing arms 253 are generally perpendicular to the spring arm 251 and the longitudinal axis of introducer needle 31. Each biasing arm 253 defines a hole 254 therethrough to allow introducer needle 31 to extend therethrough. Each clip arm 252 defines a hole 255 adjacent to their distal end. Holes 255 are adapted to engage detent 26 formed on the proximal end of catheter hub 24. When introducer needle 31 extends past the distal end of needle shield 40 into catheter hub 24, introducer needle 31 also extends through holes 254. This pulls biasing arms 253 together and thus pulls clip arms 252 inwardly toward catheter hub 24 so holes 255 engage detents 26. This maintains needle shield 40 connected to catheter hub 24. Once introducer needle 31 is pulled proximal of biasing arms 253, spring arm 251 returns to its unbiased non-clipped position where clip arms 252 are released from catheter hub 24 so that holes 255 no longer engage detent 26. Of course as discussed above, the configuration of the distal ends of clip arms 252 and detent 26 could be changed. For example, detent 26 could be rectangular or have some other geometric shape. Alternatively, detent 26 could be a slot and a radially inwardly extending finger could be disposed on the distal end of clip arms 252 to mechanically engage detent 26. The operation of retention plate 1100 is the same as discussed above with the embodiment of FIG. 37.

A seventh embodiment for the spring clip 1217 with a transverse barrier that prevents unwanted distal movement of introducer needle 31 once sharp distal tip 32 of introducer needle 31 has been proximally withdrawn into needle shield 40 is shown in FIGS. 70 through 73. In this embodiment, no enlarged diameter portion 38 is needed on introducer needle 31. Instead, spring clip 1217 includes a transverse barrier 796 that engages sharp distal tip 32 of introducer needle 31 to prevent unwanted distal movement of introducer needle 31. When introducer needle 31 extends through needle shield 40 so that sharp distal tip 32 is distal of distal opening 45, introducer needle 31 also extends through holes 794. This pulls biasing arms 798 together and thus pulls clip arms 792 adjacent to catheter hub 24. Once sharp distal tip 32 is moved proximally behind holes 794, spring arm 791 moves to its unbiased, non-clipped position so that transverse barrier 796 is in front of sharp distal tip 32. This prevents any subsequent unwanted distal movement of introducer needle. Of course, biasing arms 798 could be formed with interlocking fingers as disclosed in the embodiment of FIGS. 51 through 53.

Using tether 50 to connect needle shield 40 with needle hub 34 prevents unwanted proximal movement of introducer needle 31 with respect to needle shield 40. As discussed above, tether 50 can take many different forms such as a string, a pleated element, a sleeve member surrounding introducer needle 31 or a plurality of telescoping members surrounding introducer needle 31.

Figure 74:
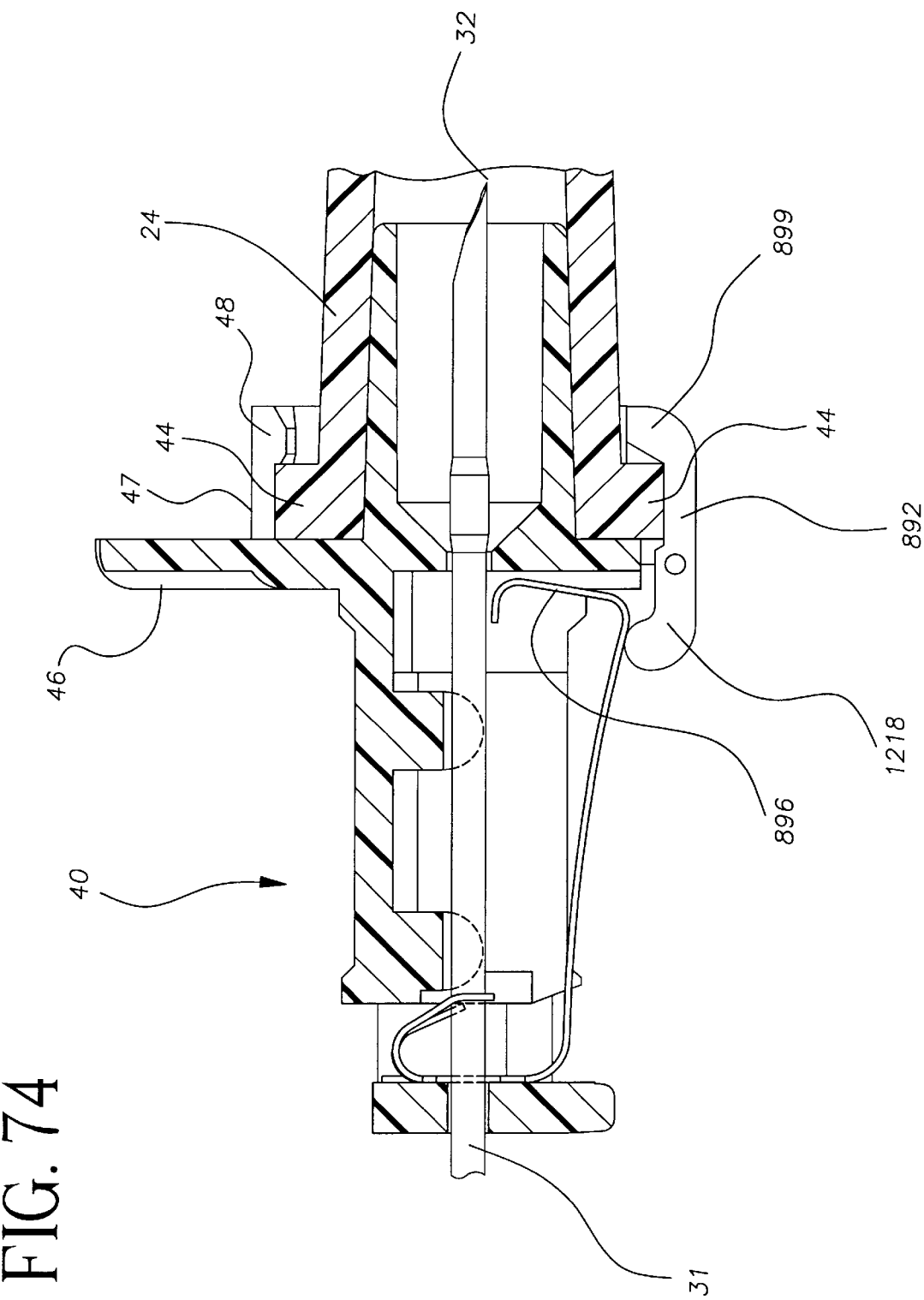
FIG. 74 is a partial cross-sectional view of the needle shield with an eighth embodiment of the spring clip with a transverse barrier that connects the needle shield to the catheter hub until the sharp distal tip of the introducer needle is shielded by the needle shield and the distal portion of the introducer needle and the proximal portion of the catheter hub with the sharp distal tip of the introducer needle extending from the distal end of the needle shield with the needle shield connected to the catheter hub.
Figure 75:
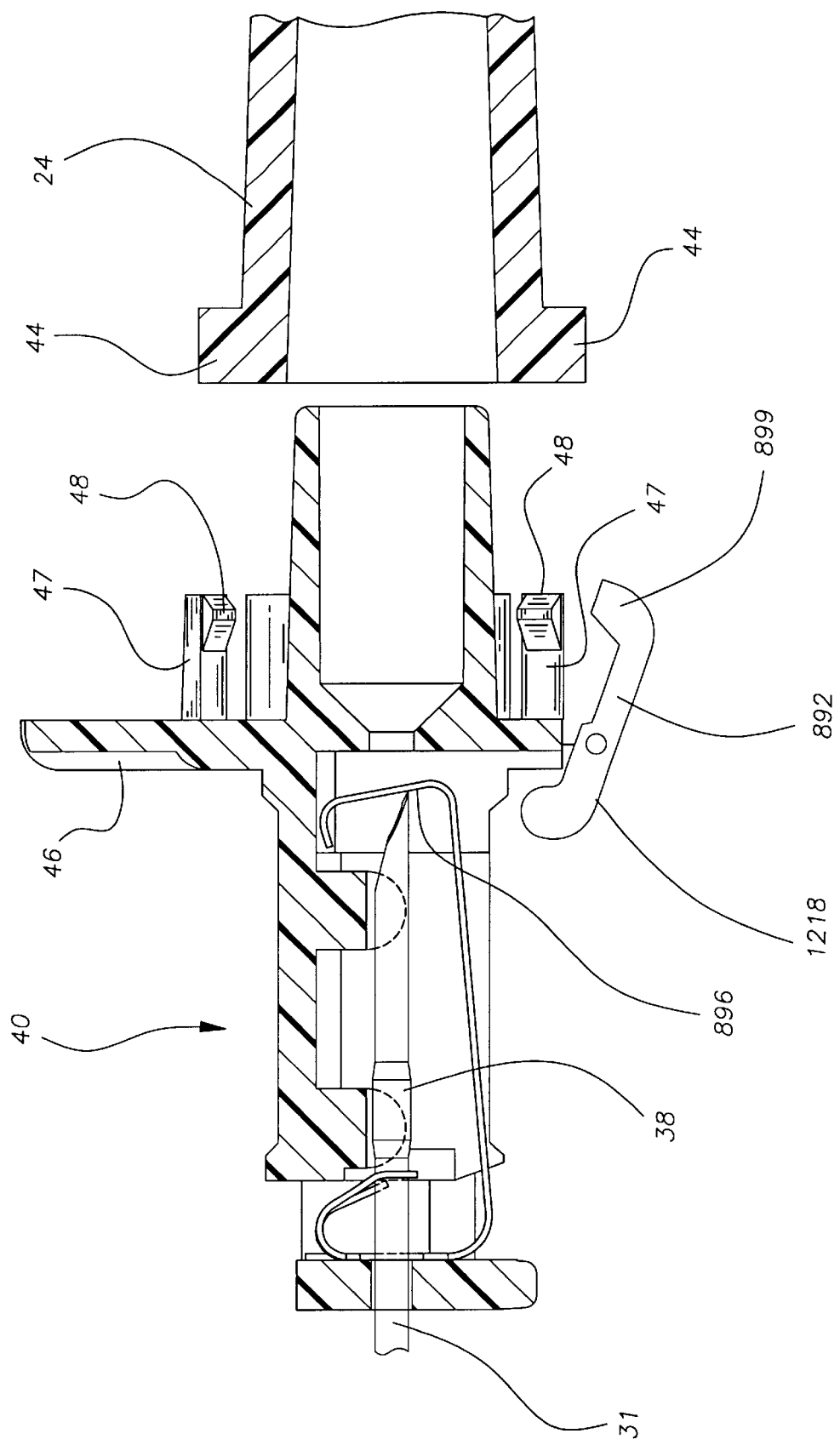
FIG. 75 is a partial cross-sectional view of the needle shield with the eighth embodiment spring clip with a transverse barrier that connects the needle shield to the catheter hub until the sharp distal tip of the introducer needle is shielded by the needle shield, and the distal portion of the introducer needle and the proximal portion of the catheter hub with the sharp distal tip of the introducer needle locked in the needle shield with the needle shield disconnected from the catheter hub.

An eighth embodiment for spring clip 1218 having a transverse barrier that connects needle shield 40 to catheter hub 24 until sharp distal tip 32 is shielded in needle shield 40 is shown in FIGS. 74 and 75. In this embodiment, spring clip 1218 includes a clip arm 892 that is pivotally connected to needle shield 40. Clip arm 892 includes a finger 899 for mechanically engaging flange 44 of catheter hub 24. With this eighth embodiment of spring clip 1218, a leaf spring with a transverse barrier 896 to engage sharp distal tip 32 of introducer needle 31 is used to prevent unwanted distal movement of introducer needle 31. In the position shown in FIG. 74, transverse barrier 896 is held in its outward position by the engagement of the end of transverse barrier 896 with the shaft of introducer needle 31. This holds spring clip 1218 in the clipped position. When introducer needle 31 is retracted, transverse barrier 896 is no longer constrained by the shaft of introducer needle 31 and thus moves inward. In this position, transverse barrier 896 is distal of sharp distal tip 32 and thus locks introducer needle 31 in needle shield 40. Since transverse barrier 896 is no longer holding clip arm 892 in position, it can rotate out of engagement with catheter hub 24. See FIG. 75. Thus, catheter hub 24 can be removed from needle shield 40. Of course it is to be understood that spring clip 1218 of this embodiment also may be used in conjunction with the leaf spring disclosed in FIGS. 19 through 21. All that is required is a mechanism to rotate clip arm 892 into and out of position with respect to catheter hub 24.

Figure 76:
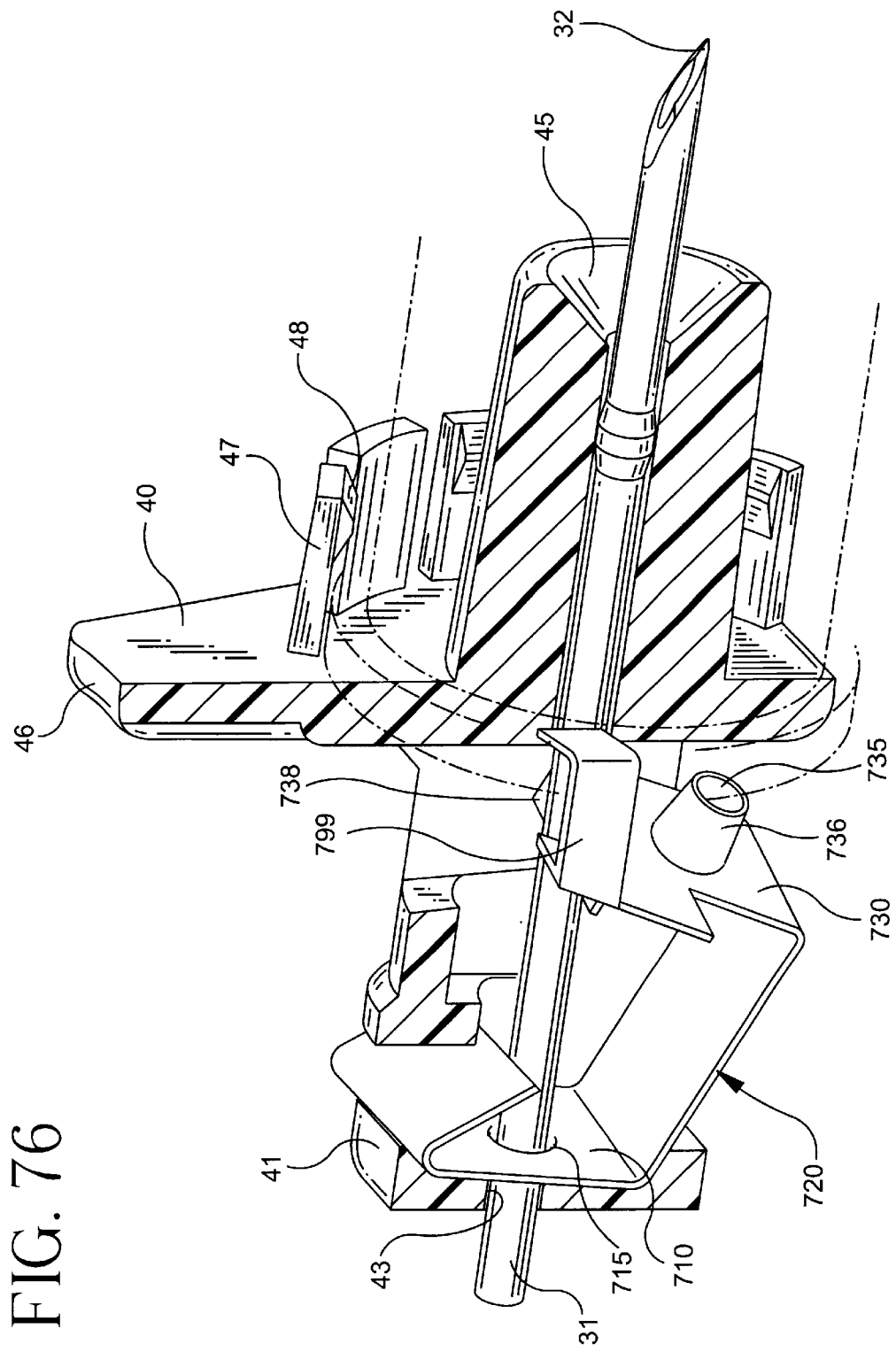
FIG. 76 is a perspective partial cross-sectional view of the needle shield with a modified version of the seventh embodiment of the lock that prevents unwanted distal movement of the introducer needle and the distal portion of the introducer needle with the sharp distal tip of the introducer needle extending from the distal end of in the- needle shield wherein the needle shield has a clip that connects the needle shield to the catheter hub until the sharp distal tip of the introducer needle is shielded by the needle shield.
Figure 77:
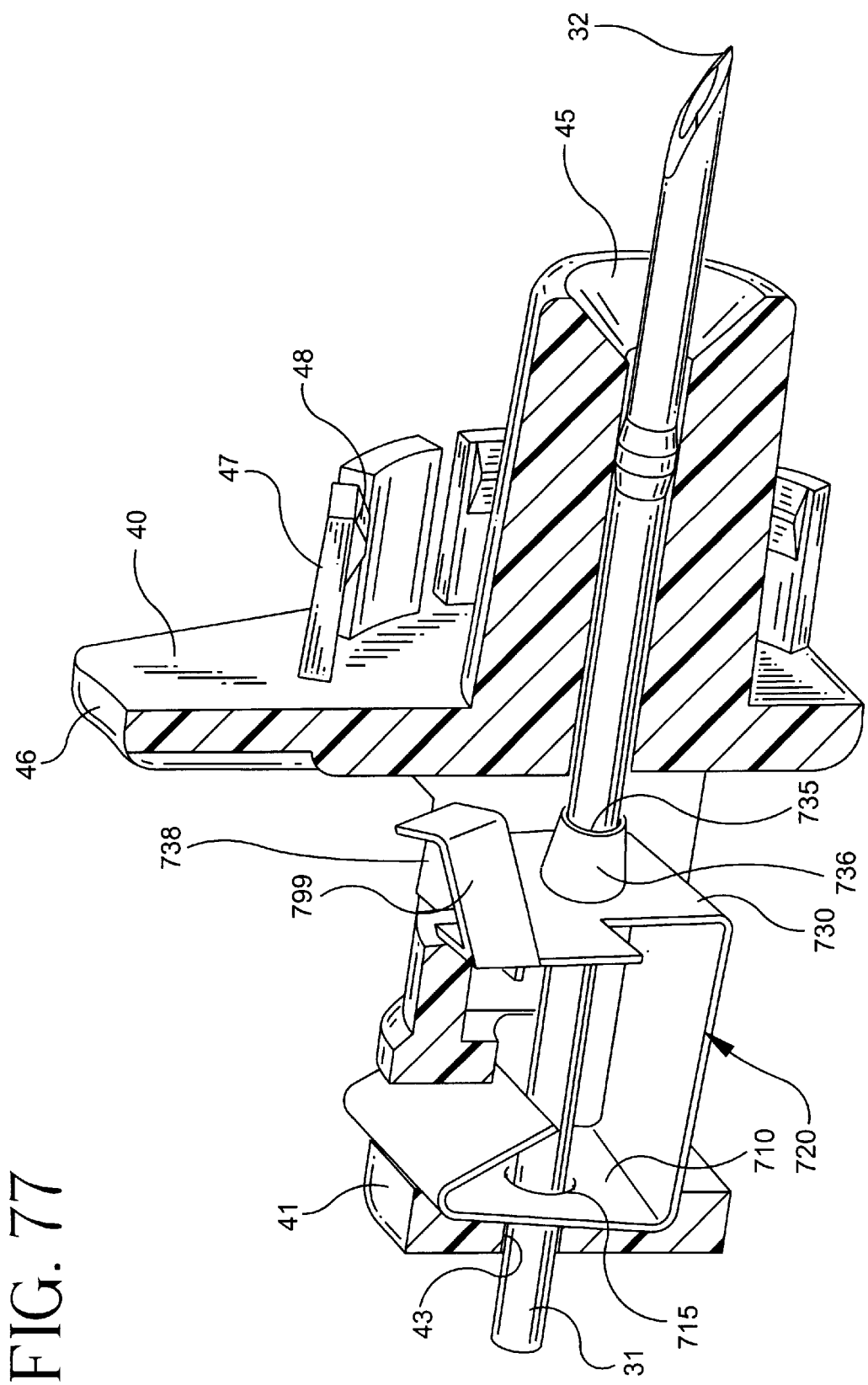
FIG. 77 is a perspective partial cross-sectional view of the needle shield with the modified version of the seventh embodiment of the lock that prevents unwanted distal movement of the introducer needle and the distal portion of the introducer needle with the sharp distal tip of the introducer needle locked in the needle shield wherein the needle shield has a clip that connects the needle shield to the catheter hub until the sharp distal tip of the introducer needle is shielded by the needle shield.

Another embodiment for spring clip 799 that connects needle shield 40 to catheter hub 24 until sharp distal tip 32 is shielded in needle shield 40 is shown in FIGS. 76 and 77. The lock for preventing unwanted distal movement of introducer needle 31 can be the embodiment shown in FIGS. 19 through 21. When sharp distal tip 32 of introducer needle 31 is distal of the distal end of needle shield 40, locking leg 730 contacts and is biased toward introducer needle 31 and spring clip 799, which acts as a hook, engages flange 44 of catheter hub 24. See FIG. 76. As introducer needle 31 is withdrawn proximally into needle shield 40 locking leg 730 rides over the surface of introducer needle 31. Locking leg 730 can include a proximally or distally directed tab 738 that contacts introducer needle 31 to minimize drag on introducer needle 31. Once sharp distal tip 32 of introducer needle 31 is moved proximal of locking leg 730, leaf spring 700 returns to its unbiased, i.e. activated, non-clipped position such that opening 735 is substantially aligned with the longitudinal axis of introducer needle 31. In this position, spring clip 799 no longer engages flange 44 of catheter hub 24 so that the catheter can be disconnected from needle shield 40. See FIG. 77. If introducer needle 31 is thereafter moved distally with respect to needle shield 40, sharp distal tip 32 of introducer needle 31 extends through opening 735 until enlarged diameter portion 38 engages opening 735. Unwanted distal movement of introducer needle 31 is thus prevented so that sharp distal tip 32 cannot be re-exposed outside needle shield 40.

Locking leg 730 can have a funnel configuration 736 adjacent to opening 735. This funnel configuration 736 acts as a guide for introducer needle 31 to ensure that it passes through opening 735 if introducer needle 31 is moved distally after it has been withdrawn into needle shield 40. Funnel configuration 736 can be configured so that it is complementary to the shape of the tapered distal portion 38b of enlarged diameter portion 38 shown in FIG. 3C. Alternatively, locking leg 730 can be replaced with a transverse barrier arrangement, such as shown in FIGS. 74 and 75.

In order to place catheter 21 into a patient's blood vessel, the clinician substantially longitudinally aligns introducer needle 31 and catheter 21 with the target blood vessel. The bevel of sharp distal tip 32 should be facing substantially away from the skin surface during venipuncture. The clinician inserts introducer needle 31 and catheter 21 at a shallow angle, preferably less than about 35 degrees, into the skin so that sharp distal tip 32 enters the target blood vessel. The clinician then preferably observes a blood flashback in the flashback chamber of needle hub 34.

After confirming placement of introducer needle 31 and catheter 21 in the target blood vessel, the clinician advances catheter 21 distally axially along introducer needle 31 into position in the blood vessel. In certain techniques, introducer needle 31 may be partially withdrawn into catheter 21 before catheter 21 is completely advanced into position in the blood vessel. After proper placement of catheter 21 is achieved, the clinician places a finger from her other hand on the patient's skin over the blood vessel approximately over the distal end of catheter 21. By placing her finger on the patient's skin and applying sufficient pressure on the skin, the clinican thereby substantially occludes or at least minimizes blood flow through catheter 21. The clinican then withdraws introducer needle 31 completely from catheter 21 by moving needle hub 34 proximally. This movement causes introducer needle 31 to move proximally into needle shield 40.

Where one of the embodiments of the spring clip disclosed herein to connect needle shield 40 to catheter hub 24 until sharp distal tip 32 of introducer needle 31 has been withdrawn into needle shield 40 is used, needle shield 40 remains engaged with catheter hub 24 during this proximal movement of introducer needle 31. Once sharp distal tip 32 of introducer needle 31 has been withdrawn into needle shield 40 so that the lock engages introducer needle 31 to prevent unwanted distal movement of sharp distal tip 32 of introducer needle 31 out of the distal end of needle shield 40, needle shield 40 can be disconnected from catheter hub 24. After introducer needle 31 and needle shield 40 have been removed from catheter hub 24, the clinician may then attach a fluid delivery device, a PRN, a deadender cap or some other blood monitoring device to catheter hub 24 and commence the planned treatment. Introducer needle 31 and needle shield 40 may then be disposed of according to the facility's disposal protocol.

Thus, it is seen that a catheter and introducer needle assembly with needle shield is provided that is compact, simple and easy to use, that requires no special features or technique to be operative, that automatically shields the sharp distal tip of the introducer needle upon withdrawal of the introducer needle from the catheter and where the needle shield remains connected to the catheter until the needle shield covers the sharp distal tip of the introducer needle.

We claim:

1. A catheter and introducer needle assembly, comprising:
   a catheter having a proximal end and a distal end;
   a catheter hub in fluid communication with the catheter and having a proximal end and a distal end connected to the proximal end of the catheter;
   an introducer needle disposed in the catheter and having a proximal end and a distal end, and an axis extending from the proximal end to the distal end; and
   a needle shield having a proximal portion and a distal portion and including a resilient clip that is adapted to flex between a biased position and an unbiased position in a plane substantially perpendicular to the axis on the introducer needle;
   wherein, in the biased position, the clip engages the catheter hub and, in the unbiased condition, the clip disengages the catheter hub; and
   wherein, when the distal end of the introducer needle extends from the distal portion of the needle shield, the clip is held to one side of the introducer needle so it is flexed into the biased position and, when the sharp distal end of the introducer needle is withdrawn into the needle shield, the clip flexes to the unbiased position out of engagement with the catheter hub.

2. The catheter and introducer needle assembly of claim 1 wherein the clip includes a spring arm and at least one clip arm that extends from the spring arm.

3. The catheter and introducer needle assembly of claim 2 wherein the clip arm includes a finger thereon.

4. The catheter and introducer needle assembly of claim 3 wherein the finger mechanically engages the catheter hub to hold the catheter hub to the needle shield when the introducer needle contacts the clip.

5. The catheter and introducer needle assembly of claim 4 wherein the finger has a proximal face and a distal face and wherein at least a portion of the finger proximal face engages the catheter hub and at least a portion of the finger distal face engages the shield when the clip is in the biased condition.

6. The catheter and introducer needle assembly of claim 5 wherein, when the clip is In the biased position, the shield engages the distal face of the finger to resist axial movement of the finger.

7. The catheter and introducer needle assembly of claim 5 wherein the catheter hub includes an engagement member which is mechanically engaged by the finger when the introducer needle contacts the clip so the catheter hub is connected to the needle shield until the distal end of the introducer needle is withdrawn into the needle shield.

8. The catheter and introducer needle assembly of claim 7 wherein the engagement member is a thread or detent.

9. A catheter and introducer needle assembly, comprising:
a catheter having a proximal end and a distal end;
a catheter hub in fluid communication with the catheter and having a proximal end and a distal end connected to the proximal end of the catheter;
an introducer needle disposed in the catheter and having a proximal end and a distal end; and
a needle shield having a proximal portion and a distal portion and including a resilient clip having a generally V-shaped configuration including a pair of legs, which clip is adapted to flex into and out of engagement with the catheter hub;
wherein when the distal end of the introducer needle extends from the distal portion of the needle shield, the introducer needle contacts the clip so that the pair of legs is retained to one side of the introducer needle and flexed into a biased position into engagement with the catheter hub and, when the sharp distal end of the introducer needle is withdrawn into the needle shield, the introducer needle no longer contacts the clip so it can flex to its unbiased position out of engagement with the catheter hub.

10. The catheter and introducer needle assembly of claim 9 wherein the pair of legs straddles the longitudinal axis of the assembly when the clip is in its unbiased position.

11. The catheter and introducer needle assembly of claim 10 wherein the V-shaped clip includes a clip arm extending generally parallel to the longitudinal axis of the assembly.

12. The catheter and introducer needle assembly of claim 11 wherein the clip arm engages the catheter hub.

13. The catheter and introducer needle assembly of claim 12 wherein the needle shield includes a ramp inclining transversely to a longitudinal axis of the assembly and wherein the clip arm engages the ramp as the clip flexes to an unbiased position, which guides the movement of the clip arm out of engagement with the catheter hub.

14. A catheter and introducer needle assembly, comprising:
a catheter having a proximal end and a distal end;
a catheter hub in fluid communication with the catheter and having a proximal end and a distal end, wherein the distal end of the catheter hub is connected to the proximal end of the catheter;
an introducer needle disposed in the catheter and having a proximal end, a distal end and an axis; and
a needle shield having a proximal portion and a distal portion and including a means for engaging the catheter hub when the distal end of the introducer needle extends from the distal portion of the needle shield and for becoming disengaged from the catheter hub when the sharp distal end of the introducer needle is withdrawn into the needle shield.

15. The catheter and introducer needle assembly of claim 14 wherein the means for engaging the catheter is adapted to move solely through a plane perpendicular to the axis of the introducer needle.

16. The catheter and introducer needle assembly of claim 14 wherein the means for engaging the catheter hub comprises a resilient clip having a generally V-shaped configuration.

17. The catheter and introducer needle assembly of claim 16 wherein the resilient clip includes a clip arm.

18. The catheter and introducer needle assembly of claim 17 wherein the clip arm includes a finger thereon.

19. The catheter and introducer needle assembly of claim 18 wherein the finger mechanically engages the catheter hub to hold the catheter hub to the needle shield when the introducer needle contacts the clip.

20. A catheter and introducer needle assembly, comprising:
a catheter having a proximal end and a distal end;
a catheter hub in fluid communication with the catheter and having a proximal end and a distal end connected to the proximal end of the catheter and having a thread or detent at the proximal end,
an introducer needle disposed in the catheter and having a proximal end and a sharp distal end; and
a needle shield having a proximal portion and a distal portion and including a resilient clip having a generally V-shaped configuration and having a spring arm and a clip arm having a finger thereon wherein clip arm and the finger are adapted to flex into and out of engagement with the thread or detent of the catheter hub and having a ramp generally inclining transverse to the axis of the introducer needle, wherein when the distal end of the introducer needle extends from the distal portion of the needle shield, the introducer needle retains the clip in a biased position to one side of the introducer needle so that the clip arm and finger are flexed into a biased position into engagement with the catheter hub and when the distal end of the introducer needle is withdrawn into the needle shield, the introducer needle no longer retains the clip and the clip flexes perpendicularly to the needle axis to its unbiased position wherein the clip arm engages the ramp as the clip moves to its unbiased position causing the clip arm and finger to move out of engagement with the catheter hub.

* * * * *